(12) United States Patent
Short et al.

(10) Patent No.: US 7,078,035 B2
(45) Date of Patent: Jul. 18, 2006

(54) PHYTASES, NUCLEIC ACIDS ENCODING THEM AND METHODS FOR MAKING AND USING THEM

(75) Inventors: Jay M. Short, Del Mar, CA (US); Kevin A. Gray, San Diego, CA (US); Nelson R. Barton, San Diego, CA (US); James B. Garrett, San Diego, CA (US); Eileen O'Donoghue, San Diego, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 10/156,660

(22) Filed: May 24, 2002

(65) Prior Publication Data

US 2003/0103958 A1 Jun. 5, 2003

Related U.S. Application Data

(60) Continuation-in-part of application No. 09/866,379, filed on May 24, 2001, now Pat. No. 6,855,365, which is a continuation-in-part of application No. 09/580,515, filed on May 25, 2000, now Pat. No. 6,720,014, which is a continuation-in-part of application No. 09/318,528, filed on May 25, 1999, now Pat. No. 6,183,740, which is a continuation-in-part of application No. 09/291,931, filed on Apr. 13, 1999, now Pat. No. 6,190,897, which is a continuation of application No. 09/259,214, filed on Mar. 1, 1999, now Pat. No. 6,110,719, which is a division of application No. 08/910,798, filed on Aug. 13, 1997, now Pat. No. 5,876,997.

(51) Int. Cl.
| | |
|---|---|
| *C12N 9/06* | (2006.01) |
| *C07K 1/00* | (2006.01) |
| *C07H 21/04* | (2006.01) |
| *A23J 1/00* | (2006.01) |
| *A61K 38/46* | (2006.01) |

(52) U.S. Cl. .................. 424/94.6; 435/195; 435/69.1; 435/196; 435/19; 435/174; 435/176; 435/180; 530/350; 536/23.2; 426/656

(58) Field of Classification Search ............... 435/195, 435/196, 69.1, 19, 174, 176, 180; 536/23.2; 530/350; 424/94.6; 426/656
See application file for complete search history.

(56) References Cited

U.S. PATENT DOCUMENTS

| 5,284,933 A | 2/1994 | Döbeli et al. |
| 5,366,736 A | 11/1994 | Edwards, Jr. |
| 5,436,156 A | 7/1995 | Van Gorcom et al. |
| 5,593,963 A | 1/1997 | Van Ooijen et al. |
| 5,750,135 A * | 5/1998 | Schleicher et al. ......... 424/442 |
| 5,830,696 A | 11/1998 | Short |
| 5,830,732 A | 11/1998 | Mochizuki et al. |
| 5,939,303 A | 8/1999 | Cheng et al. |
| 6,039,942 A * | 3/2000 | Lassen et al. ............ 435/252.3 |
| 6,190,897 B1 | 2/2001 | Kretz |

FOREIGN PATENT DOCUMENTS

| EP | 0 282 042 B1 | 6/1994 |
| EP | 0 897 985 A2 | 2/1999 |
| GB | 2316082 | 2/1996 |
| KR | 99066028 | 12/1999 |
| WO | WO 99/08539 | 2/1999 |
| WO | WO-00/58481 | 10/2000 |
| WO | WO 00/64247 | 11/2000 |
| WO | WO-00/71728 | 11/2000 |

OTHER PUBLICATIONS

Witkowski et al., Biochemistry 38:11643-11650, 1999.*
Ostanin et al., J. Biol. Chem. 267(32):22830-22836, 1992.*
Stephen F. Altschul, Warren Gish, Webb Miller, Eugene W. Myers and David J. Lipman, "Basic Local Alignment Search Tool", 1990, Academic Press Limited, J. Mol. Bio. vol. 215, pp. 403-410.
Henrik Brinch-Pedersen, Annette Olesen, Soren K. Rasmussen & Preben B. Holm, "Generation of Transgenic Wheat (*Triticum aestivum* L.) for Constitutive Accumulation of an *Aspergillus* Phytase", 2000, Molecular Breeding, pp. 195-206.
Janie Dassa, Christian Marck, and Paul L. Boquet, "The Complete Nucleotide Sequence of the *Escherichia coli* Gene *appA* Reveals Significant Homology between pH 2.5 Acid Phosphatase and Glucose-1-Phosphatase", Sep., 1990, Journal of Bacteriology, vol. 172, No. 9, pp. 5497-5500.
J. Dvorakova, "Phytase: Sources, Preparation and Exploitation", 1998, Folia Microbiol, vol. 434(4), pp. 323-338.
R. Greiner, U. Konietzny, and KI..-D. Jany, "Purification and Characterization of Two Phytases from *Escherichia coli*", May 15, 1993, Archives of Biochemistry and Biophysics, vol. 303, No. 1, pp. 107-113.
William R. Pearson and David J. Lipman, "Improved Tools for Biological Sequence Comparison", Apr. 1988, National Academy of Sciences, vol. 85, pp. 2444-2448.

(Continued)

*Primary Examiner*—Rebecca E. Prouty
*Assistant Examiner*—Delia M. Ramirez
(74) *Attorney, Agent, or Firm*—Morrison & Foerster LLP

(57) ABSTRACT

The invention provides isolated and recombinant phytase enzymes. In one aspect, the phytases are produced by modification of the wild type appA of *E. coli*. The enzyme can be produced from recombinant host cells. The phytases of the invention can be used to aid in the digestion of phytate where desired. In particular, the phytases of the invention can be used in foodstuffs to improve the feeding value of phytate rich ingredients. The phytases of the invention can be thermotolerant and/or thermostable. Also provided are methods for obtaining a variant polynucleotide encoding a phytase and for obtaining a phytase with thermostability or thermotolerant at high or low temperatures.

54 Claims, 22 Drawing Sheets

OTHER PUBLICATIONS

Jan Pen, Theo C. Verwoerd, Peter A. vanParidon, Rob F. Beudeker, Peter J.M. van den Elzen, Kees Geerse, Jan D. van der Klis, Hans A. J. Versteegh, Albert J.J. van Ooyen and Andre' Hoekema, "Phytase-containing Transgenic Seeds as a Novel Feed Additive for Improved Phosphorus Utilization", Jul., 1993, Bio/Technology vol. 11, pp. 79-82.

Eric Rodriguez, Yanming Han, and Xin Gen Lei, "Cloning, Sequencing, and Expression of an *Escherichia coli* Acid Phosphatase/Phytase Gene (appA2) Isolated from Pig Colon", 1999, Biochemical and Biophysical Research Communications, vol. 257, pp. 117-123.

J. Rozas and R. Rozas, "DnaSP, DNA Sequence Polymorphism: An Interactive Program for Estimating Population Genetics Parameters from DNA Sequence Data", 1995, Cabios, vol. 11 No. 6, pp. 61-625.

T. C. Verwoerd, A. Hoekema, P.A. van Paridon, A.J.J. van Ooyen, & J. Pen, "Phytase-enriched Transgenic Seeds as a Novel Feed Additive", 1993, Med. Fac. Landbouww. Univ. Gent. No. 58/4a, pp. 1719-1721.

Database accession No. AR130956, Genbank, May 16, 2001.

Database accession No. P07102, Swiss Prot, Sep. 15, 2003.

Golovan et al., Characterization and overproduction of the *Escherichia coli* appA encoded bifunctional enzyme that exhibits both phytase and acid phosphatase activities, *Canadian Journal of Microbiology*, vol. 46, No. 1, pp. 59-71, Jan., 2000.

Arnold, "Enzyme engineering reaches the boiling point", *Proc. Natl. Acad. Sci.*, pp. 2035-2036, Mar. 1998.

Lehmann, et al., "Exchanging the active site between phytases for altering the funcitonal properties of the enzyme", *Protein Science*, pp. 1866-1872, 2000.

Lehmann, et al., "From DNA sequence to improved functionality: using protein sequence comparisons to rapidly design a thermostable consensus phytase", *Protein Engineering*, vol. 13, No. 1, pp. 49-57, 2000.

Bork, et al., "Powers and Pitfalls in Sequence Analysis: the 70% Hurdle", *Genome Research*, pp. 398-400, vol. 10, 2000.

Broun, et al., "Catalytic Plasticity of Fatty Acid Modification Enzymes Underlying Chemical Diversity of Plant Lipids", *Science*, vol. 282, pp. 1315-1317, Nov. 13, 1998.

Van de Loo, et al., "An oleate 12-hydroxylase from *Ricinus communis* L. is a fatty acyl desaturase homolog", *Proc. Natl. Acad. Sci.*, vol. 2, pp. 6743-6747, 1995.

Seffernick, et al., "Melamine Deaminase and Atrazine Chlorohydrolase: 98 percent Identical but Functionally Different", *Journal of Bacteriology*, vol. 183, No. 8; pp. 2405-1410, Apr., 2001.

Database accession No. A02249, EMBL, Jan. 18, 1994.

Giver, et al., *Directed evolution of a thermostable esterase*, Proc. Natl. Acad. Sci., USA vol. 95, pp. 12809-12813, Oct. 1998 Biochemistry.

Lehmann, et al., *The consensus concept for thermostability engineering of proteins*, Biochimica et Biophysica Acta 1543 (2000) 408-415.

Jermutus, et al., *Structure-based chimeric enzymes as an alternative to directed enzyme evolution: Phytase as a test case* Journal of Biotechnology 85 (2001) 15-24.

Tomschy, et al., *Optimization of the catalytic properties of Aspergillus fumigatus phytase bsed on the three-dimensional structure* Protein Science (2000) 9:1304-1311.

Vetriani, et al., *Protein thermostability above 100° C: A key role for ionic interactions* Proc. Natl. Acad. Sci USA vol. 95 pp. 12300-12305, Oct. 1998.

Wyss, et al. *Biochemical Characterization of Fungal Phytases (myo-Inositol Hexakisphosphate Phosphohydrolases): Catalytic Properties* Applied and Environmental Microbiology, Feb. 1999, pp. 367-373.

Database accession No. AAX 26540, May 27, 1999, 1 page.

Bae et al., Geneseq accession No. ABK12514, Dec. 15, 1999.

Forsberg et al., Geneseq accession No. AAC68296, Nov. 2, 2000.

Forsberg et al., Geneseq accession No. AAC68299, Nov. 2, 2000.

International Search Report mailed on Jul. 27, 2004, for PCT patent application No. PCT/US02/16482 filed on May 24, 2002, 9 pages.

Ostanin et al., GenBank accession No. L03371 (1992).

Altschul et al., "Basic Local Alignment Search Tool," *J. Mol. Biol.* 215:403-410 (1990).

Dassa et al., "The Complete Nucleotide Sequence of the *Escherichia coli* Gene *app*A Reveals Significant Homology between pH 2.5 Acid Phosphatase and Glucose-1-Phosphatase," *Journal of Bacteriology* 172(9):5497-5500 (1990).

Pearson and Lipman, "Improved tools for biological sequence comparison," *Proc. Natl. Acad. Sci. USA* 85:2442-2448 (1988).

Pen et al., "Phytase-containing Transgenic Seeds as a Novel Feed Additive for Improved Phosphorus Utilization," *Bio/Technology* 11(7):811-814 (1993).

Rodriguez et al., "Cloning, Sequencing, and Expression of an *Escherichia coli* Acid Phosphatase/Phytase Gene (*appA2*) Isolated from Pig Colon," *Biochemical and Biophysical Research Communications* 257:117-123 (1999).

J. Rozas and R. Rozas, "DnaSP, DNA sequence polymorphism: an interactive program for estimating population genetics parameters from DNA sequence data," *CABIOS* 11(6):621-625 (1995).

Verwoerd et al., "Phytase-Enriched Transgenic Seeds as a Novel Feed Additive," *Med. Fac. Landbouww. Univ. Gent.*, 58(4A):1719-1721 (1993).

G. von Heijne, "A new method for predicting signal sequence cleavage sites," *Nucleic Acids Research* 14(11):4683-4690 (1986).

Berka et al., Applied and Environ. Biol. (1998) 64:4423-4427.

Boquet et al., J. of Bacteriology (1987) 169:1663-1669.

Casey and Walsh, J. Biotechnol. (2004) 110:313-322.

Delagrave et al., Protein Eng. (1993) 6:327-331.

Delagrave et al., Nature Biotech. (1993) 11:1548-1552.

Greiner et al., Archives of Biochemistry and Biophysics (1997) 341:201-206.

Institute of Applied Environmental Economics (TME) of the Netherlands, "Use of Phytase in Pig and Poultry Feed to Reduce Phosphorus Excretion," (1995).

Kerovuo et al., Applied and Environ. Biol. (1998) 64:2079-2085.

Lim et al., Nature Structural Biology (2000) 7:108-113.

NCBI GenBank entry AAB96873 phytase.

NCBI GenBank entry AAA16898 phytase.

NCBI GenBank entry AAB26466 phytase.

NCBI GenBank entry AAB96871 phytase.

Oh et al., Abstracts of the General Meeting of the American Society for Microbiology (2000) 100:499-500.

Rodriguez et al., Archives of Biochemistry and Biophysics (1999) 365:262-267.
Rodriguez et al., Archives of Biochemistry and Biophysics (2000) 382:105-112.
Van Hartingsveldt et al., Gene (1993) 127:87-94.

Wodzinski and Ullah, "Phytase," in Advantages in Applied Microbiology, Academic Press Inc., vol. 42, (1996) pp. 263-302.

* cited by examiner

FIGURE 1A

DNA Sequence (SEQ ID NO:1)

ATGAAAGCGATCTTAATCCCATTTTTATCTCTTCTGATTCCGTTAACCCCGCAATCTGCATT
CGCTCAGAGTGAGCCGGAGCTGAAGCTGGAAAGTGTGGTGATTGTCAGTCGTCATGGTG
TGCGTGCTCCAACCAAGGCCACGCAACTGATGCAGGATGTCACCCCAGACGCATGGCCA
ACCTGGCCGGTAAAACTGGGTGAGCTGACACCGCGCGGTGGTGAGCTAATCGCCTATCT
CGGACATTACTGGCGTCAGCGTCTGGTAGCCGACGGATTGCTGCCTAAATGTGGCTGCC
CGCAGTCTGGTCAGGTCGCGATTATTGCTGATGTCGACGAGCGTACCCGTAAAACAGGCG
AAGCCTTCGCCGCCGGGCTGGCACCTGACTGTGCAATAACCGTACATACCCAGGCAGATA
CGTCCAGTCCCGATCCGTTATTTAATCCTCTAAAAACTGGCGTTTGCCAACTGGATAACGC
GAACGTGACTGACGCGATCCTCGAGAGGGCAGGAGGGTCAATTGCTGACTTTACCGGGC
ATTATCAAACGGCGTTTCGCGAACTGGAACGGGTGCTTAATTTTCCGCAATCAAACTTGTG
CCTTAAACGTGAGAAACAGGACGAAAGCTGTTCATTAACGCAGGCATTACCATCGGAACT
CAAGGTGAGCGCCGACTGTGTCTCATTAACCGGTGCGGTAAGCCTCGCATCAATGCTGAC
GGAGATATTTCTCCTGCAACAAGCACAGGGAATGCCGGAGCCGGGGTGGGGAAGGATCA
CCGATTCACACCAGTGGAACACCTTGCTAAGTTTGCATAACGCGCAATTTGATTTGCTACA
ACGCACGCCAGAGGTTGCCCGCAGCCGCGCCACCCCGTTATTAGATTTGATCAAGACAG
CGTTGACGCCCCATCCACCGCAAAAACAGGCGTATGGTGTGACATTACCCACTTCAGTGC
TGTTTATCGCCGGACACGATACTAATCTGGCAAATCTCGGCGGCGCACTGGAGCTCAACT
GGACGCTTCCCGGTCAGCCGGATAACACGCCGCCAGGTGGTGAACTGGTGTTTGAACGC
TGGCGTCGGCTAAGCGATAACAGCCAGTGGATTCAGGTTTCGCTGGTCTTCCAGACTTTA
CAGCAGATGCGTGATAAAACGCCGCTGTCATTAAATACGCCGCCCGGAGAGGTGAAACTG
ACCCTGGCAGGATGTGAAGAGCGAAATGCGCAGGGCATGTGTTCGTTGGCAGGTTTTAC
GCAAATCGTGAATGAAGCACGCATACCGGCGTGCAGTTTGAGATCTCATCTA

FIGURE 1B

Protein Sequence (SEQ ID NO:2)

MKAILIPFLSLLIPLTPQSAFAQSEPELKLESVVIVSRHGVRAPTKATQLMQDV
TPDAWPTWPVKLGELTPRGGELIAYLGHYWRQRLVADGLLPKCGCPQSGQV
AIIADVDERTRKTGEAFAAGLAPDCAITVHTQADTSSPDPLFNPLKTGVCQLD
NANVTDAILERAGGSIADFTGHYQTAFRELERVLNFPQSNLCLKREKQDESCS
LTQALPSELKVSADCVSLTGAVSLASMLTEIFLLQQAQGMPEPGWGRITDSHQ
WNTLLSLHNAQFDLLQRTPEVARSRATPLLDLIKTALTPHPPQKQAYGVTLPT
SVLFIAGHDTNLANLGGALELNWTLPGQPDNTPPGGELVFERWRRLSDNSQW
IQVSLVFQTLQQMRDKTPLSLNTPPGEVKLTLAGCEERNAQGMCSLAGFTQIV
NEARIPACSLRSHL pH/Temperature Profile and Stability pH/Temperature Profile and Stability

FIGURE 5

T $_{1/2}$ of phytase in pepsin digestion

| Host | T ½ (min) |
|---|---|
| E. Coli | ~8 |
| Pichia | ~10 |
| S. Cerevisiae | ~25 |

FIGURE 6

Predicted glycosylation sites

QSEPELKLES VVIVSRHGVR APTKATQLMQ DVT̲PDAWPT̲W PVKLGELTPR GGELIAYLGH

YWRQRLVADG LLPKCGCPQS GQVAIIADVD ERTRKTGEAF AAGLAPDCAI TVHT̲QADT̲S̲

PDPLFNPLKT GVCQLDNAN̲v TDAILERAGG SIADFTGHYQ TAFRELERVL NFPQSNLCLK

REKQDESCSL TQALPSELKV SADCVSLTGA VSLASMLTEI FLLQQAGMP EPGWGRITDS

HQWNTLLSLH NAQFDLLQRT PEVARSRATP LLDLIKT̲ALT PHPPQKQAYG VTLPTSVLFI

AGHDTNLANL GGALELN̲WTL PGQPDNTPPG GELVFERWRR LSDNSQWIQV SLVFQTLQQM

RDKTPLSLNT PPGEVKLTLA GCEERNAQGM CSLAGFTQIV NEARIPACSL

FIGURE 7

Conclusion from SDS Page

| | Pichia | S. Cerevisiae |
|---|---|---|
| O-glycosylation | no | no |
| N-glycosylation | yes | yes |
| N-glycosylated form | 1 dominates | 2 |

Maximum peptide mapping

FIGURE 9A

Identified glycosylation sites for Phytase from Pichia

```
QSEPEPLKLES VVIVSRHGVR APTKATQLMQ DVTPDAWPTW PVKLGELTPR GGELIAYLGH
YWRQRLVADG LLPKCGCPQS GQVAIIADVD ERTRKTGEAF AAGLAPDCAI TVHTQADTSS
PDPLFNPLKT GVCQLDNANV TDAILERAGG SIADFTGHYQ TAFRELERVL NFPQSNLCLK
REKQDESCSL TQALPSELKV SADCVSLTGA VSLASMLTEI FLLQQAQGMP EPGWGRITDS
HQWNTLLSLH NAQFDLLQRT PEVARSRATP LLDLIKTALT PHPPQKQAYG VTLPTSVLFI
AGHDTNLANL GGALELNWTL PGQPDNTPPG GELVFERWRR LSDNSQWIQV SLVFQTLQQM
RDKTPLSLNT PPGEVKLTLA GCEERNAQGM CSLAGFTQIV NEARIPACSL
```

FIGURE 9B

Identified glycosylation sites for Phytase from S. Cerevisiae

```
QSEPELKLES  VVIVSRHGVR  APTKATQLMQ  DVTPDAWPTW  PVKLGELTPR  GGELIAYLGH
YWRQRLVADG  LLPKCGCPQS  GQVAIIADVD  ERTRKTGEAF  AAGLAPDCAI  TVHTQADTSS
PDPLFNPLKT  GVCQLDNANV  TDAILERAGG  SIADFTGHYQ  TAFRELERVL  NFPQSNLCLK
REKQDESCSL  TQALPSELKV  SADCVSLTGA  VSLASMLTEI  FLLQQAQGMP  EPGWGRITDS
HQWNTLLSLH  NAQFDLLQRT  PEVARSRATP  LLDLIKTALI  PHPPQKQAYG  VTLPTSVLFI
AGHDTNLANL  GGALELNWTL  PGQPDNTPPG  GELVFERWRR  LSDNSQWIQV  SLVFQTLQQM
RDKTPLSLNT  PPGEVKLTLA  GCEERNAQGM  CSLAGFTQIV  NEARIPACSL
```

FIGURE 10

Summary

- Phytase in Pichia
  - There are three forms of phytase expressed in Pichia. Each of them contains a single glyco-chain linked on amino acid #317, or #344, or #369.

- Phytase in S. Cerevisiae
  - There are three forms of phytase expressed in S. Cerevisiae. The first form has two glyco-chain linked on amino acid #317 and #344. The second and third form carries a single glyco-chain that is linked on amino acid #317 or #344.

FIGURE 13

E. coli appA  (GenBank accession no. M58708 )  (SEQ ID NO:3)

```
   1 taaggagcag aaacaatgtg gtatttactt tggttcgtcg gcattttgtt gatgtgttcg
  61 ctctccaccc ttgtgttggt atggctggac ccgcgtctga aaagttaacg aacgtaggcc
 121 tgatgcggcg cattagcatc gcatcaggca atcaataatg tcagatatga aaagcggaaa
 181 catatcgatg aaagcgatct taatcccatt tttatctctt ctgattccgt taaccccgca
 241 atctgcattc gctcagagtg agccggagct gaagctggaa agtgtggtga ttgtcagtcg
 301 tcatggtgtg cgtgctccaa ccaaggccac gcaactgatg caggatgtca ccccagacgc
 361 atggccaacc tggccggtaa aactgggttg gctgacaccg cgnggtggtg agctaatcgc
 421 ctatctcgga cattaccaac gccagcgtct ggtagccgac ggattgctgg cgaaaaaggg
 481 ctgccgcag tctggtcagg tcgcgattat tgctgatgtc gacgagcgta cccgtaaaac
 541 aggcgaagcc ttcgccgccg ggctggcacc tgactgtgca ataaccgtac atacccaggc
 601 agatacgtcc agtcccgatc cgttatttaa tcctctaaaa actggcgttt gccaactgga
 661 taacgcgaac gtgactgacg cgatcctcag cagggcagga gggtcaattg ctgactttac
 721 cgggcatcgg caaacggcgt ttcgcgaact ggaacggg tg cttaattttc cgcaatcaaa
 781 cttgtgcctt aaacgtgaga aacaggacga aagctgttca ttaacgcagg cattaccatc
 841 ggaactcaag gtgagcgccg acaatgtctc attaaccggt gcggtaagcc tcgcatcaat
 901 gctgacggag atatttctcc tgcaacaagc acagggaatg ccggagccgg ggtggggaag
 961 gatcaccgat tcacaccagt ggaacacctt gctaagtttg cataacgcgc aatttatttt
1021 gctacaacgc acgccagagg ttgcccgcag ccgcgccacc ccgtattag atttgatcaa
1081 gacagcgttg acgccccatc caccgcaaaa acaggcgtat ggtgtgacat tacccacttc
1141 agtgctgttt atcgccggac acgatactaa tctggcaaat ctcggcggcg cactggagct
1201 caactggacg cttccccggtc agccggataa cacgccgcca ggtggtgaac tggtgtttga
1261 acgctggcgt cggctaagcg ataacagcca gtggattcag gtttcgctgg tcttccagac
1321 tttacagcag atgcgtgata aaacgccgct gtcattaaat acgccgccg gagaggtgaa
1381 actgaccctg gcaggatgtg aagagcgaaa tgcgcagggc atgtgttcgt tggcaggttt
1441 tacgcaaatc gtgaatgaag cacgcatacc ggcgtgcagt ttgtaatgca taaaaaagag
1501 cattcagtta cctgaatgct ctgaggctga tgacaaacga agaactgtct aatgcgtaga
1561 ccggaaaagg cgttcacgcc gcatccggcc actttcagtt ttcctctttc tcggagtaac
1621 tataaccgta atagttatag ccgtaactgt aagcggtgct ggcgcgttta atcacaccat
1681 tgaggatagc gcctttaata ttgacgcctg cctgttccag acgctgcatt gacaaactca
1741 cctctttggc ggtgttcaag ccaaaacgcg caaccagcag gctggtgcca acagaacgcc
1801 ccacgaccgc ggcatcactc accgccagca tcggcggcgt atcgacaatc accagatcgt
1861 aatggtcgtt cgcccattcc agtaattgac gcatccgatc g
```

FIGURE 14

Amino acid sequence for *E. coli* appA phytase (wild type) (SEQ ID NO:4)

MKAILIPFLSLLIPLTPQSAFAQSEPELKLESVVIVSRHGVRAPTKATQLMQDVT
PDAWPTWPVKLGWLTPRGGELIAYLGHYQRQRLVADGLLAKKGCPQSGQVA
IIADVDERTRKTGEAFAAGLAPDCAITVHTQADTSSPDPLFNPLKTGVCQLDNA
NVTDAILSRAGGSIADFTGHRQTAFRELERVLNFPQSNLCLKREKQDESCSLTQ
ALPSELKVSADNVSLTGAVSLASMLTEIFLLQQAQGMPEPGWGRITDSHQWNT
LLSLHNAQFYLLQRTPEVARSRATPLLDLIKTALTPHPPQKQAYGVTLPTSVLFI
AGHDTNLANLGGALELNWTLPGQPDNTPPGGELVFERWRRLSDNSQWIQVSL
VFQTLQQMRDKTPLSLNTPPGEVKLTLAGCEERNAQGMCSLAGFTQIVNEARI
PACSL

PHYTASES, NUCLEIC ACIDS ENCODING THEM AND METHODS FOR MAKING AND USING THEM

CROSS-REFERENCE TO RELATED APPLICATIONS

This application is a continuation-in-part of U.S. patent application Ser. No. 09/866,379, filed May 24, 2001, now U.S. Pat. No. 6,855,365, which is a continuation-in-part of U.S. Ser. No. 09/580,515, filed May 25, 2000, now U.S. Pat. No. 6,720,014, which is a continuation-in-part of U.S. Ser. No. 09/318,528, filed May 25, 1999, now U.S. Pat. No. 6,183,740, which is a continuation-in-part of U.S. Ser. No. 09/291,931, filed Apr. 13, 1999, now U.S. Pat. No. 6,190,897, which is a continuation of U.S. Ser. No. 09/259,214, filed Mar. 1, 1999, now U.S. Pat. No. 6,110,719, which is a divisional of U.S. Ser. No. 08/910,798, now U.S. Pat. No. 5,876,997, filed Aug. 13, 1997. Each of the aforementioned applications and patent are explicitly incorporated herein by reference in their entirety and for all purposes.

FIELD OF THE INVENTION

This invention relates to newly made polynucleotides, polypeptides encoded by such polynucleotides, uses of such polynucleotides and polypeptides, as well as the production and isolation of such polynucleotides and polypeptides. In particular, the invention provides polypeptides having phytase activity, e.g., SEQ ID NO:1. The invention provides isolated and recombinant phytase enzymes. The phytases can be produced by modification of the wild type appA of *E. coli* or they can be produced from recombinant host cells. The phytases of the invention can be used to aid in the digestion of phytate. The phytases of the invention can be used in foodstuffs to improve the feeding value of phytate rich ingredients. The phytases of the invention can be thermotolerant and/or thermostable. Also provided are methods for obtaining a variant polynucleotide encoding a phytase and for obtaining a phytase with thermostability or thermotolerant at high or low temperatures.

BACKGROUND

Minerals are essential elements for the growth of all organisms. Dietary minerals can be derived from many source materials, including plants. For example, plant seeds are a rich source of minerals since they contain ions that are complexed with the phosphate groups of phytic acid molecules. These phytate-associated minerals may, in some cases, meet the dietary needs of some species of farmed organisms, such as multi-stomached ruminants. Accordingly, in some cases ruminants require less dietary supplementation with inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released. The majority of species of farmed organisms, however, are unable to efficiently utilize phytate-associated minerals. Thus, for example, in the livestock production of monogastric animals (e.g., pigs, birds, and fish), feed is commonly supplemented with minerals and/or with antibiotic substances that alter the digestive flora environment of the consuming organism to enhance growth rates.

As such, there are many problematic burdens—related to nutrition, ex vivo processing steps, health and medicine, environmental conservation, and resource management—that are associated with an insufficient hydrolysis of phytate in many applications. The following are non-limiting examples of these problems:

1) The supplementation of diets with inorganic minerals is a costly expense.
2) The presence of unhydrolyzed phytate is undesirable and problematic in many ex vivo applications (e.g. by causing the presence of unwanted sludge).
3) The supplementation of diets with antibiotics poses a medical threat to humans and animals alike by increasing the abundance of antibiotic-tolerant pathogens.
4) The discharge of unabsorbed fecal minerals into the environment disrupts and damages the ecosystems of surrounding soils, fish farm waters, and surface waters at large.
5) The valuable nutritional offerings of many potential foodstuffs remain significantly untapped and squandered.

Many potentially nutritious plants, including particularly their seeds, contain appreciable amounts of nutrients, e.g. phosphate, that are associated with phytate in a manner such that these nutrients are not freely available upon consumption. The unavailability of these nutrients is at least partially overcome by some organisms, including cows and other ruminants that have a sufficient digestive ability—largely derived from the presence of symbiotic life forms in their digestive tracts—to hydrolyze phytate and liberate the associated nutrients. However, the majority of species of farmed animals, including pigs, fish, chickens, turkeys, as well as other non-ruminant organisms including man, are unable to efficiently liberate these nutrients after ingestion.

Consequently, phytate-containing foodstuffs require supplementation with exogenous nutrients and/or with a source of phytase activity in order to amend their deficient nutritional offerings upon consumption by a very large number of species of organisms.

In yet another aspect, the presence of unhydrolyzed phytate leads to problematic consequences in ex vivo processes including—but not limited to—the processing of foodstuffs. In but merely one exemplification, as described in EP0321004-B1 (Vaara et al.), there is a step in the processing of corn and sorghum kernels whereby the hard kernels are steeped in water to soften them. Water-soluble substances that leach out during this process become part of a corn steep liquor, which is concentrated by evaporation. Unhydrolyzed phytic acid in the corn steep liquor, largely in the form of calcium and magnesium salts, is associated with phosphorus and deposits an undesirable sludge with proteins and metal ions. This sludge is problematic in the evaporation, transportation and storage of the corn steep liquor.

The supplementation of diets with antibiotic substances has many beneficial results in livestock production. For example, in addition to its role as a prophylactic means to ward off disease, the administration of exogenous antibiotics has been shown to increase growth rates by upwards of 3–5%. The mechanism of this action may also involve—in part—an alteration in the digestive flora environment of farmed animals, resulting in a microfloral balance that is more optimal for nutrient absorption.

However, a significant negative effect associated with the overuse of antibiotics is the danger of creating a repository of pathogenic antibiotic-resistant microbial strains. This danger is imminent, and the rise of drug-resistant pathogens in humans has already been linked to the use of antibiotics in livestock. For example, Avoparcin, the antibiotic used in animal feeds, was banned in many places in 1997, and animals are now being given another antibiotic, virginiamycin, which is very similar to the new drug, Synercid®, used to replace vancomycin in human beings. However, studies have already shown that some enterococci in farm animals are resistant to Synercid®, Consequently, undesired tolerance consequences, such as those already seen with Avoparcin and vancomycin, are likely to reoccur no matter what new antibiotics are used as blanket prophylactics for farmed animals. Accordingly, researchers are calling for tighter controls on drug use in the industry.

The increases in growth rates achieved in animals raised on foodstuffs supplemented with the instantly disclosed phytase molecules matches—if not exceeds—those achieved using antibiotics such as, for example, Avoparcin. Accordingly, the instantly disclosed phytase molecules—either alone or in combination with other reagents (including but not limited to enzymes, including proteases)—are serviceable not only in this application (e.g., for increasing the growth rate of farmed animals) but also in other applications where phytate hydrolysis is desirable.

An environmental consequence is that the consumption of phytate-containing foodstuffs by any organism species that is phytase-deficient—regardless of whether the foodstuffs are supplemented with minerals—leads to fecal pollution resulting from the excretion of unabsorbed minerals. This pollution has a negative impact not only on the immediate habitat but consequently also on the surrounding waters. The environmental alterations occur primarily at the bottom of the food chain, and therefore have the potential to permeate upwards and throughout an ecosystem to effect permanent and catastrophic damage—particularly after years of continual pollution. This problem has the potential to manifest itself in any area where concentrated phytate processing occurs—including in vivo (e.g. by animals in areas of livestock production, zoological grounds, wildlife refuges, etc.) and in vitro (e.g. in commercial corn wet milling, ceral steeping processes, and the like) processing steps.

The decision to use exogenously added phytase molecules—whether to fully replace or to augment the use of exogenously administered minerals and/or antibiotics—ultimately needs to pass a test of financial feasibility and cost effectiveness by the user whose livelihood depends on the relevant application, such as livestock production.

Consequently, there is a need for means to achieve efficient and cost effective hydrolysis of phytate in various applications. Particularly, there is a need for means to optimize the hydrolysis of phytate in commercial applications. In a particular aspect, there is a need to optimize commercial treatment methods that improve the nutritional offerings of phytate-containing foodstuffs for consumption by humans and farmed animals.

Phytate occurs as a source of stored phosphorous in virtually all plant feeds (Graf (Ed.), 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are largely unavailable for absorption by monogastric animals, which lack phytase activity.

Although some hydrolysis of phytate occurs in the colon, most phytate passes through the gastrointestinal tract of monogastric animals and is excreted in the manure contributing to fecal phosphate pollution problems in areas of intense livestock production. Inorganic phosphorous released in the colon has an appreciably diminished nutritional value to livestock because inorganic phosphorous is absorbed mostly—if not virtually exclusively—in the small intestine. Thus, an appreciable amount of the nutritionally important dietary minerals in phytate is unavailable to monogastric animals.

In sum, phytate-associated nutrients are comprised of not only phosphate that is covalently linked to phytate, but also other minerals that are chelated by phytate as well. Moreover, upon ingestion, unhydrolyzed phytate may further encounter and become associated with additional minerals. The chelation of minerals may inhibit the activity of enzymes for which these minerals serve as co-factors.

Conversion of phytate to inositol and inorganic phosphorous can be catalyzed by microbial enzymes referred to broadly as phytases. Phytases such as phytase #EC 3.1.3.8 are capable of catalyzing the hydrolysis of myo-inositol hexaphosphate to D-myo-inositol 1,2,4,5,6-pentaphosphate and orthophosphate. Certain fungal phytases reportedly hydrolyze inositol pentaphosphate to tetra-, tri-, and lower phosphates. For example, *A. ficuum* phytases reportedly produce mixtures of myoinositol di- and mono-phosphates (Ullah, 1988). Phytase-producing microorganisms are comprised of bacteria such as *Bacillus subtilis* (Powar and Jagannathan, 1982) and *Pseudomonas* (Cosgrove, 1970); yeasts such as *Sacchoromyces cerevisiae* (Nayini and Markakis, 1984); and fungi such as *Aspergillus terreus* (Yamada et al., 1968).

Acid phosphatases are enzymes that catalytically hydrolyze a wide variety of phosphate esters and usually exhibit pH optima below 6.0 (Igarashi and Hollander, 1968). For example, #EC 3.1.3.2 enzymes catalyze the hydrolysis of orthophosphoric monoesters to orthophosphate products. An acid phosphatase has reportedly been purified from *A. ficuum*. The deglycosylated form of the acid phosphatase has an apparent molecular weight of 32.6 kDa (Ullah et al., 1987).

Phytase and less specific acid phosphatases are produced by the fungus *Aspergillus ficuum* as extracellular enzymes (Shieh et al., 1969). Ullah reportedly purified a phytase from wild type *A. ficuum* that had an apparent molecular weight of 61.7 kDA (on SDS-PAGE; as corrected for glycosylation); pH optima at pH 2.5 and pH 5.5; a Km of about 40 μm; and, a specific activity of about 50 U/mg (Ullah, 1988). PCT patent application WO 91/05053 also reportedly discloses isolation and molecular cloning of a phytase from *Aspergillus ficuum* with pH optima at pH 2.5 and pH 5.5, a Km of about 250 μm, and specific activity of about 100 U/mg protein. Summarily, the specific activity cited for these previously reported microbial enzymes have been approximately in the range of 50–100 U/mg protein.

The possibility of using microbes capable of producing phytase as a feed additive for monogastric animals has been reported previously (U.S. Pat. No. 3,297,548 Shieh and Ware; Nelson et al., 1971). The cost-effectiveness of this approach has been a major limitation for this and other commercial applications. Therefore improved phytase molecules are highly desirable.

Microbial phytases may also reportedly be useful for producing animal feed from certain industrial processes, e.g., wheat and corn waste products. In one aspect, the wet milling process of corn produces glutens sold as animal feeds. The addition of phytase may reportedly improve the nutritional value of the feed product. For example, the use of fungal phytase enzymes and process conditions (t~50° C. and pH~5.5) have been reported previously in (e.g. EP 0 321 004). Briefly, in processing soybean meal using traditional steeping methods, i.e., methods without the addition of exogenous phytase enzyme, the presence of unhydrolyzed phytate reportedly renders the meal and wastes unsuitable for feeds used in rearing fish, poultry and other non-ruminants as well as calves fed on milk. Phytase is reportedly useful for improving the nutrient and commercial value of this high protein soy material (see Finase Enzymes by Alko, Rajamäki, Finland). A combination of fungal phytase and a pH 2.5 optimum acid phosphatase form *A. niger* has been used by Alko, Ltd as an animal feed supplement in their phytic acid degradative product Finas F and Finase S. However, the cost-effectiveness of this approach has remained a major limitation to more widespread use. Thus a cost-effective source of phytase would greatly enhance the value of soybean meals as an animal feed (Shieh et al., 1969).

To solve the problems disclosed, the treatment of foodstuffs with exogenous phytase enzymes has been proposed, but this approach was not been fully optimized, particularly with respect to feasibility and cost efficiency. This optimization requires the consideration that a wide range of applications exists, particularly for large-scale production. For example, there is a wide range of foodstuffs, preparation methods thereof, and species of recipient organisms.

In a particular exemplification, it is appreciated that the manufacture of fish feed pellets requires exposure of ingredients to high temperatures and/or pressure in order to produce pellets that do not dissolve and/or degrade prematurely (e.g. prior to consumption) upon subjection to water. It would thus be desirable for this manufacturing process to obtain additive enzymes that are stable under high temperature and/or pressure conditions. Accordingly it is appreciated that distinct phytases may be differentially preferable or optimal for distinct applications.

It is furthermore recognized that an important way to optimize an enzymatic process is through the modification and improvement of the pivotal catalytic enzyme. For example, a transgenic plant can be formed that is comprised of an expression system for expressing a phytase molecule. It is appreciated that by attempting to improve factors that are not directly related to the activity of the expressed molecule proper, such as the expression level, only a finite—and potentially insufficient—level of optimization may be maximally achieved. Accordingly, there is also a need for obtaining molecules with improved characteristics.

SUMMARY OF THE INVENTION

The invention provides an isolated or recombinant nucleic acid comprising a nucleic acid sequence having at least 98% sequence identity to SEQ ID NO:1 over a region of at least about 100 residues, wherein the nucleic acids encode at least one polypeptide having a phytase activity and the sequence identities are determined by analysis with a sequence comparison algorithm or by a visual inspection. In alternative embodiments, the nucleic acid sequence has at least 98% sequence identity to SEQ ID NO:1 over a region of at least about 50 residues, 100 residues, 150 residues, 200 residues, 250 residues, 300 residues, 350 residues, 400 residues, 450 residues, 500 residues, 550 residues, 600 residues, 700 residues, 800 residues, 900 residues, 1000 residues, 1200 residues or 1300 residues.

In alternative embodiments the nucleic acid sequence has at least 98%, 98.5%, 99% or 99.5% sequence identity to SEQ ID NO:1 over a region of at least about 50 residues, 100 residues, 150 residues, 200 residues, 250 residues, 300 residues, 350 residues, 400 residues, 450 residues, 500 residues, 550 residues, 600 residues, 700 residues, 800 residues, 900 residues, 1000 residues, 1200 residues or 1300 residues. The nucleic acid sequence can have a sequence as set forth in SEQ ID NO:1. The nucleic acid sequence can encode a polypeptide having a sequence as set forth in SEQ ID NO:2.

In one aspect, the sequence comparison algorithm is a BLAST version 2.2.2 algorithm. The filtering setting can be set to blastall -p blastp -d "nr pataa"-F F, and all other options are set to default.

In one aspect, the phytase activity comprises catalysis of phytate (myo-inositol-hexaphosphate) to inositol and inorganic phosphate, or equivalent. The phytase activity can comprise the hydrolysis of phytate (myo-inositol-hexaphosphate).

In one aspect, the phytase activity can be thermostable or thermotolerant. The polypeptide can retain a phytase activity under conditions comprising a temperature range of between about 40° C. to about 70° C. The polypeptide can retain a phytase activity after exposure to a temperature in the range from greater than 37° C. to about 90° C. The polypeptide can retain a phytase activity after exposure to a temperature in the range from greater than 37° C. to about 50° C.

The invention provides an isolated or recombinant nucleic acid comprising a sequence that hybridizes under stringent conditions to a nucleic acid sequence as set forth in SEQ ID NO:1, wherein the nucleic acid encodes a polypeptide having a phytase activity. The nucleic acid is at least about 50 residues, 100 residues, 150 residues, 200 residues, 250 residues, 300 residues, 350 residues, 400 residues, 450 residues, 500 residues, 550 residues, 600 residues, 700 residues, 800 residues, 900 residues, 1000 residues, 1200 residues or 1300 residues in length. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide with a phytase activity, wherein the probe comprises at least 10 consecutive bases of a sequence selected from a group consisting of a sequence as set forth in SEQ ID NO:1, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence as set forth in SEQ ID NO:1.

The invention provides a nucleic acid probe for identifying a nucleic acid encoding a polypeptide with a phytase activity, wherein the probe comprises a nucleic acid sequence having at least 98% sequence identity to SEQ ID NO:1 over a region of at least about 100 residues, wherein the sequence identities are determined by analysis with a sequence comparison algorithm or by visual inspection. The probe can comprise an oligonucleotide comprising at least about 10 to 50, about 20 to 60, about 30 to 70, about 40 to 80, or about 60 to 100 consecutive bases of a nucleic acid sequence as set forth in SEQ ID NO:1. The probe can comprise a nucleic acid sequence having at least 99% sequence identity to a nucleic acid sequence as set forth in SEQ ID NO:1. The probe can comprise a subset of a sequence as set forth in SEQ ID NO:1.

The invention provides an amplification primer sequence pair for amplifying a nucleic acid encoding a polypeptide with a phytase activity, wherein the primer pair is capable of amplifying a nucleic acid sequence as set forth in SEQ ID NO:1. In one aspect, each member of the amplification primer sequence pair comprises an oligonucleotide comprising at least about 10 to 50 consecutive bases of the sequence.

The invention provides a method of amplifying a nucleic acid encoding a polypeptide with a phytase activity comprising amplification of a template nucleic acid with an amplification primer sequence pair capable of amplifying a nucleic acid sequence as set forth in SEQ ID NO:1.

The invention provides an expression cassette comprising a nucleic acid of the invention, e.g., a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof.

The invention provides a vector comprising a nucleic acid of the invention, e.g., a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof.

The invention provides a cloning vehicle comprising a vector of the invention or a nucleic acid of the invention, wherein the cloning vehicle comprises a viral vector, a plasmid, a phage, a phagemid, a cosmid, a fosmid, a bacteriophage or an artificial chromosome. The viral vector can comprise an adenovirus vector, a retroviral vectors or an adeno-associated viral vector. The viral vector can comprise a bacterial artificial chromosome (BAC), a plasmid, a bacteriophage P1-derived vector (PAC), a yeast artificial chromosome (YAC), a mammalian artificial chromosome (MAC).

The invention provides a transformed cell comprising a vector of the invention or a nucleic acid of the invention. The vector can comprise a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof.

The invention provides a transformed cell comprising a vector of the invention or a nucleic acid of the invention. The nucleic acid can comprise a nucleic acid sequence at least 98% sequence identity to SEQ ID NO:1 over a region of at least about 100 residues, wherein the sequence identities are determined by analysis with a sequence comparison algorithm or by visual inspection, or, the nucleic acid hybridizes under stringent conditions to a nucleic acid sequence as set forth in SEQ ID NO:1, or a subsequence thereof. In alternative aspects, the cell is a bacterial cell, a mammalian cell, a fungal cell, a yeast cell, an insect cell or a plant cell.

The invention provides a transgenic non-human animal comprising a vector of the invention or a nucleic acid or the invention. In one aspect, the nucleic acid comprises at least 98% sequence identity to SEQ ID NO:1 over a region of at least about 100 residues, wherein the sequence identities are determined by analysis with a sequence comparison algorithm or by visual inspection, or, comprises a nucleic acid that hybridizes under stringent conditions to a nucleic acid sequence as set forth in SEQ ID NO:1, or a subsequence thereof. In alternative aspects, transgenic non-human animal is a mouse, a goat or a pig.

The invention provides a transgenic plant comprising a vector of the invention or a nucleic acid or the invention. In one aspect, the nucleic acid sequence has at least 98% sequence identity to SEQ ID NO:1 over a region of at least about 100 residues, wherein the sequence identities are determined by analysis with a sequence comparison algorithm or by visual inspection, or, the nucleic acid hybridizes under stringent conditions to a nucleic acid sequence as set forth in SEQ ID NO:1, or a subsequence thereof. In alternative aspects, the plant is a corn plant, a potato plant, a tomato plant, a wheat plant, an oilseed plant, a rapeseed plant, a soybean plant or a tobacco plant.

The invention provides a transgenic seed comprising a vector of the invention or a nucleic acid or the invention. In one aspect, the nucleic acid sequence has at least 98% sequence identity to SEQ ID NO:1 over a region of at least about 100 residues, wherein the sequence identities are determined by analysis with a sequence comparison algorithm or by visual inspection, or, the nucleic acid hybridizes under stringent conditions to a nucleic acid sequence as set forth in SEQ ID NO:1, or a subsequence thereof. In alternative aspects, the seed is a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof, or, a nucleic acid sequence as set forth in SEQ ID NO:1. The antisense oligonucleotide can be between about 10 to 50, about 20 to 60, about 30 to 70, about 40 to 80, or about 60 to 100 bases in length.

The invention provides a method of inhibiting the translation of a phytase message in a cell comprising administering to the cell or expressing in the cell an antisense oligonucleotide comprising a nucleic acid sequence complementary to or capable of hybridizing under stringent conditions to a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof.

The invention provides an isolated or recombinant polypeptide comprising an amino acid sequence having at least 98% sequence identity to SEQ ID NO:2 over a region of at least about 100 residues, or, a polypeptide encoded by a nucleic acid comprising a sequence: (i) having at least 98% sequence identity to SEQ ID NO:1 over a region of at least about 100 residues, wherein the sequence identities are determined by analysis with a sequence comparison algorithm or by visual inspection, or, (ii) that hybridizes under stringent conditions to a nucleic acid as set forth in SEQ ID NO:1. In one aspect, the polypeptide has a phytase activity. The phytase activity can comprise the hydrolysis of phytate (myo-inositol-hexaphosphate).

In one aspect, the isolated or recombinant polypeptide has a thermotolerant phenotype, i.e., its phytase activity is thermotolerant. In one aspect, the isolated or recombinant polypeptide has a thermostable phenotype, i.e., its phytase activity is thermostable.

In alternative aspects, the isolated or recombinant polypeptide (amino acid sequence) of the invention has at least 98% sequence identity to SEQ ID NO:2 over a region of at least about 100 residues, wherein the sequence identities are determined by analysis with a sequence comparison algorithm or by a visual inspection. In alternative embodiments, the amino acid sequence has at least 98% sequence identity to SEQ ID NO:2 over a region of at least about 50 residues, 100 residues, 150 residues, 200 residues, 250 residues, 300 residues, 350 residues, 400 residues or 435 residues.

In alternative aspects, the isolated or recombinant polypeptide (amino acid sequence) of the invention has at least 98%, 98.5%, 99% or 99.5% sequence identity to SEQ ID NO:2 over a region of at least about 50 residues, 100 residues, 150 residues, 200 residues, 250 residues, 300 residues, 350 residues, 400 residues or 435. The isolated or recombinant polypeptide (amino acid sequence) of the invention can have a sequence as set forth in SEQ ID NO:2. The polypeptide can be encoded by a nucleic acid having a sequence as set forth in SEQ ID NO:1. In one aspect, the sequence comparison algorithm is a BLAST version 2.2.2 algorithm. The filtering setting can be set to blastall -p blastp -d "nr pataa"-F F, and all other options are set to default.

The isolated or recombinant polypeptide (amino acid sequence) of the invention can have a phytase activity. In one aspect, the phytase activity comprises catalysis of phytate (myo-inositol-hexaphosphate) to inositol and inorganic phosphate, or equivalent. The phytase activity can comprise the hydrolysis of phytate (myo-inositol-hexaphosphate).

The invention provides an isolated or recombinant polypeptide, wherein the polypeptide has a phytase activity and lacks a signal sequence and comprises an amino acid sequence of the invention, e.g., a sequence having at least 98% sequence identity to SEQ ID NO:2 over a region of at least about 100 residues, or, a polypeptide encoded by a nucleic acid comprising a sequence: (i) having at least 98% sequence identity to SEQ ID NO:1 over a region of at least about 100 residues, wherein the sequence identities are determined by analysis with a sequence comparison algorithm or by visual inspection, or, (ii) that hybridizes under stringent conditions to a nucleic acid as set forth in SEQ ID NO:1. In alternative aspects, the phytase activity comprises a thermostability when heated to a temperature in the range from about 37° C. to about 50° C., about 50° C. to about 70° C. or about 70° C. to about 90° C. The thermostable phytase activity can comprise a specific activity at about 37° C. in the range from about 100 to about 1000 units per milligram of protein. The thermostable phytase activity can comprise a specific activity from about 500 to about 750 units per milligram of protein. The thermostable phytase activity can comprise a specific activity at 37° C. in the range from about 500 to about 1200 units per milligram of protein. The thermostable phytase activity can comprise a specific activity at 37° C. in the range from about 750 to about 1000 units per milligram of protein. The phytase activity can be thermotolerance after being heated to an elevated temperature in the range from about 37° C. to about 90° C., or, after being heated to a temperature in the range from about 37° C. to about 70° C. The thermotolerance can comprise retention of at least half of the specific activity of the phytase at 37° C. after being heated to the elevated temperature. The thermotolerance can comprise retention of specific activity at 37° C. in the range from about 500 to about 1200 units per milligram of protein after being heated to the elevated temperature. The phytase can comprise at least one glycosylation site. The glycosylation can be one or more N-linked glycosylations or one or more N-linked glycosylations or a combination thereof. The phytase can be glycosylated in vitro or in vivo, e.g., after being expressed in a cell, e.g., a eukaryotic cells, e.g., a yeast cell, e.g., *P. pastoris* or a *S. pombe*, or an insect cell, or a mammalian cell, e.g., a human cell. In one aspect, the polypeptide retains a phytase activity under acidic conditions, e.g., conditions comprising about pH 5, or, under conditions comprising about pH 4.5.

The invention provides a protein preparation comprising a polypeptide of the invention, wherein the protein preparation comprises a liquid, a solid or a gel.

The invention provides a heterodimer comprising a polypeptide of the invention and a second domain. In one aspect, the second domain is a polypeptide and the heterodimer is a fusion protein. The second domain can be an epitope or a tag or a combination thereof.

The invention provides an immobilized polypeptide having a phytase activity, wherein the polypeptide comprises a polypeptide (amino acid) sequence of the invention or a heterodimer or fusion protein of the invention. In one aspect, the phytase is immobilized on a cell, a metal, a resin, a polymer, a ceramic, a glass, a microelectrode, a graphitic particle, a bead, a gel, a plate, an array or a capillary tube.

The invention provides an array comprising an immobilized polypeptide of the invention or a heterodimer or fusion protein of the invention, or a nucleic acid of the invention.

The invention provides an isolated or recombinant antibody that specifically binds to a polypeptide of the invention or to a polypeptide encoded by a nucleic acid of the invention. The antibody can be a monoclonal or a polyclonal antibody. The invention provides a hybridoma comprising an antibody that specifically binds to a polypeptide of the invention or to a polypeptide encoded by a nucleic acid of the invention.

The invention provides a food supplement for an animal comprising a polypeptide of the invention or to a polypeptide encoded by a nucleic acid of the invention. The polypeptide in the food supplement can be glycosylated.

The invention provides an edible enzyme delivery matrix comprising a polypeptide of the invention or to a polypeptide encoded by a nucleic acid of the invention, wherein the polypeptide comprises a phytase activity. The edible enzyme delivery matrix can comprise a pellet, a tablet or a pill. The polypeptide of the invention in the edible enzyme delivery matrix can be glycosylated. The polypeptide of the invention in the edible enzyme delivery matrix can be thermotolerant and/or thermostable.

The invention provides an edible pellet comprising a granulate edible carrier and a polypeptide of the invention or to a polypeptide encoded by a nucleic acid of the invention, wherein the polypeptide comprises a phytase activity.

The invention provides a feed composition comprising a foodstuff comprising a recombinant phytase protein having at least thirty contiguous amino acids of an amino acid sequence as set forth in SEQ ID NO:2 or a conservative variation thereof, and an edible carrier. The phytase protein in the foodstuff can be glycosylated. The phytase protein in the foodstuff can be thermotolerant and/or thermostable. The foodstuff can be manufactured in pellet, pill or tablet form. The foodstuff can be produced using polymer coated additives. The foodstuff can be manufactured in granulate form. The foodstuff can be produced by spray drying.

The invention provides a soybean meal comprising a polypeptide of the invention or to a polypeptide encoded by a nucleic acid a of the invention, wherein the polypeptide comprises a phytase activity.

The invention provides a method of isolating or identifying a polypeptide with phytase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a phytase.

The invention provides a method of making an anti-phytase antibody comprising administering to a non-human animal a nucleic acid of the invention, or a polypeptide of the invention, in an amount sufficient to generate a humoral immune response, thereby making an anti-phytase antibody.

The invention provides a method of producing a recombinant polypeptide comprising the steps of: (a) providing a nucleic acid operably linked to a promoter; wherein the nucleic acid comprises a sequence of the invention; and (b) expressing the nucleic acid of step (a) under conditions that allow expression of the polypeptide, thereby producing a recombinant polypeptide. The method can further comprise transforming a host cell with the nucleic acid of step (a) followed by expressing the nucleic acid of step (a), thereby producing a recombinant polypeptide in a transformed cell.

The invention provides a method for identifying a polypeptide having a phytase activity comprising the following steps: (a) providing a polypeptide of the invention or a polypeptide encoded by a nucleic acid having a sequence of the invention; (b) providing a phytase substrate; and (c) contacting the polypeptide or a fragment or variant thereof of step (a) with the substrate of step (b) and detecting an increase in the amount of substrate or a decrease in the amount of reaction product, wherein a decrease in the amount of the substrate or an increase in the amount of the reaction product detects a polypeptide having a phytase activity.

The invention provides a method for identifying a phytase substrate comprising the following steps: (a) providing a polypeptide of the invention or a polypeptide encoded by a nucleic acid having a sequence of the invention; (b) providing a test substrate; and (c) contacting the polypeptide of step (a) with the test substrate of step (b) and detecting an increase in the amount of substrate or a decrease in the amount of reaction product, wherein a decrease in the amount of the substrate or an increase in the amount of the reaction product identifies the test substrate as a phytase substrate.

The invention provides a method of determining whether a compound specifically binds to a polypeptide comprising the following steps: (a) expressing a nucleic acid or a vector comprising the nucleic acid under conditions permissive for translation of the nucleic acid to a polypeptide, wherein the nucleic acid has a sequence of the invention, or, providing a polypeptide of the invention; (b) contacting the polypeptide with the test compound; and (c) determining whether the test compound specifically binds to the polypeptide, thereby determining that the compound specifically binds to the polypeptide.

The invention provides a method for identifying a modulator of a phytase activity comprising the following steps: (a) providing a phytase polypeptide of the invention or a phytase polypeptide encoded by a nucleic acid of the invention; (b) providing a test compound; (c) contacting the polypeptide of step (a) with the test compound of step (b) and measuring an activity of the phytase, wherein a change in the phytase activity measured in the presence of the test compound compared to the activity in the absence of the test compound provides a determination that the test compound modulates the phytase activity. In one aspect, the phytase activity is measured by providing a phytase substrate and detecting an increase in the amount of the substrate or a decrease in the amount of a reaction product. In one aspect, a decrease in the amount of the substrate or an increase in the amount of the reaction product with the test compound is compared to the amount of substrate or reaction product without the test compound to identify the test compound as an activator of phytase activity. In one aspect, an increase in the amount of the substrate or a decrease in the amount of the reaction product with the test compound is compared to the amount of substrate or reaction product without the test compound to identify the test compound as an inhibitor of phytase activity.

The invention provides a computer system comprising a processor and a data storage device wherein said data storage device has stored thereon a polypeptide sequence or a nucleic acid sequence, wherein the polypeptide sequence comprises a polypeptide sequence of the invention, or subsequence thereof, and the nucleic acid comprises a nucleic acid sequence of the invention or subsequence thereof. The computer system can further comprising a sequence comparison algorithm and a data storage device having at least one reference sequence stored thereon. The sequence comparison algorithm can comprise a computer program that indicates polymorphisms. The computer system can further comprise an identifier that identifies one or more features in said sequence.

The invention provides a computer readable medium having stored thereon a polypeptide sequence or a nucleic acid sequence, wherein the polypeptide sequence comprises a polypeptide sequence of the invention, or subsequence thereof, and the nucleic acid comprises a nucleic acid sequence of the invention or subsequence thereof.

The invention provides a method for identifying a feature in a sequence comprising the steps of: (a) reading the sequence using a computer program which identifies one or more features in a sequence, wherein the sequence comprises a polypeptide sequence or a nucleic acid sequence, wherein the polypeptide sequence comprises sequence of the invention or subsequence thereof, and the nucleic acid comprises a sequence of the invention or subsequence thereof, and (b) identifying one or more features in the sequence with the computer program.

The invention provides a method for comparing a first sequence to a second sequence comprising the steps of: (a) reading the first sequence and the second sequence through use of a computer program which compares sequences, wherein the first sequence comprises a polypeptide sequence or a nucleic acid sequence, wherein the polypeptide sequence comprises sequence of the invention, or subsequence thereof, and the nucleic acid comprises a sequence of the invention or subsequence thereof; and (b) determining differences between the first sequence and the second sequence with the computer program. In one aspect, the step of determining differences between the first sequence and the second sequence can further comprise the step of identifying polymorphisms. The method can further comprise an identifier that identifies one or more features in a sequence. The method can further comprise reading the first sequence using a computer program and identifying one or more features in the sequence.

The invention provides a method for isolating or recovering a nucleic acid encoding a polypeptide with a phytase activity from an environmental sample comprising the steps of: (a) providing an amplification primer sequence pair for amplifying a nucleic acid encoding a polypeptide with a phytase activity, wherein the primer pair is capable of amplifying SEQ ID NO:1, or a subsequence thereof; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide with a phytase activity from an environmental sample. In one aspect, each member of the amplification primer sequence pair can comprise an oligonucleotide comprising at least about 10 to 50 consecutive bases of a sequence as set forth in SEQ ID NO:1. The invention provides a method for isolating or recovering a nucleic acid encoding a polypeptide with a phytase activity from an environmental sample comprising the steps of: (a) providing a polynucleotide probe comprising a sequence of the invention, or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide with a phytase activity from a soil sample. The environmental sample can comprise a water sample, a liquid sample, a soil sample, an air sample or a biological sample. The biological sample can be derived from a bacterial cell, a protozoan cell, an insect cell, a yeast cell, a plant cell, a fungal cell or a mammalian cell.

The invention provides a method of generating a variant of a nucleic acid encoding a phytase comprising the steps of: (a) providing a template nucleic acid comprising a nucleic acid sequence of the invention; and (b) modifying, deleting or adding one or more nucleotides in the template sequence, or a combination thereof, to generate a variant of the template nucleic acid. The method can further comprise expressing the variant nucleic acid to generate a variant phytase polypeptide. The modifications, additions or deletions can be introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis™ (GSSM™), synthetic ligation reassembly (SLR) and/or a combination thereof. The modifications, additions or deletions are introduced by recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and/or a combination thereof. In alternative aspects, the modifications, additions or deletions are introduced by error-prone PCR, by shuffling, by oligonucleotide-directed mutagenesis, by assembly PCR, by sexual PCR mutagenesis, in vivo mutagenesis, cassette mutagenesis, by recursive ensemble mutagenesis, by exponential ensemble mutagenesis, site-specific mutagenesis, by gene reassembly, by synthetic ligation reassembly (SLR) and/or by Gene Site Saturation Mutagenesis™ (GSSM™).

In one aspect, method is iteratively repeated until a phytase having an altered or different activity or an altered or different stability from that of a phytase encoded by the template nucleic acid is produced. The variant phytase polypeptide can be thermotolerant, wherein the phytase retains some activity after being exposed to an elevated temperature. The variant phytase polypeptide can have increased glycosylation as compared to the phytase encoded by a template nucleic acid. The variant phytase polypeptide can have a phytase activity under a high temperature, wherein the phytase encoded by the template nucleic acid is not active under the high temperature. In one aspect, method is iteratively repeated until a phytase coding sequence having an altered codon usage from that of the template nucleic acid is produced. In one aspect, the method is iteratively repeated until a phytase gene having higher or lower level of message expression or stability from that of the template nucleic acid is produced.

The invention provides a method for modifying codons in a nucleic acid encoding a phytase to increase its expression in a host cell, the method comprising (a) providing a nucleic acid encoding a phytase comprising a nucleic acid sequence of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides a method for modifying codons in a nucleic acid encoding a phytase, the method comprising (a) providing a nucleic acid encoding a phytase comprising a nucleic acid sequence of the invention; and, (b) identifying a codon in the nucleic acid of step (a) and replacing it with a different codon encoding the same amino acid as the replaced codon, thereby modifying codons in a nucleic acid encoding a phytase.

The invention provides a method for modifying codons in a nucleic acid encoding a phytase to increase its expression in a host cell, the method comprising (a) providing a nucleic acid encoding a phytase comprising a nucleic acid sequence of the invention; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides a method for modifying a codon in a nucleic acid encoding a phytase to decrease its expression in a host cell, the method comprising (a) providing a nucleic acid encoding a phytase comprising a sequence of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In alternative aspects, the host cell is a bacterial cell, a fungal cell, an insect cell, a yeast cell, a plant cell or a mammalian cell, e.g., a human cell.

The invention provides a method for producing a library of nucleic acids encoding a plurality of modified phytase active sites or substrate binding sites, wherein the modified active sites or substrate binding sites are derived from a first nucleic acid comprising a sequence encoding a first active site or a first substrate binding site the method comprising: (a) providing a first nucleic acid encoding a first active site or first substrate binding site, wherein the first nucleic acid sequence comprises a sequence that hybridizes under stringent conditions to a sequence as set forth in SEQ ID NO:1, and the nucleic acid encodes a phytase active site or a phytase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified phytase active sites or substrate binding sites. In one aspect, the method comprises mutagenizing the first nucleic acid of step (a) by a method comprising an optimized directed evolution system, or, a method comprising gene site-saturation mutagenesis (GSSM), or, a method comprising a synthetic ligation reassembly (SLR). The method can further comprise mutagenizing the first nucleic acid of step (a) or variants by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. The method can further comprising mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides a method making a small molecule comprising the steps of: (a) providing a plurality of biosynthetic enzymes capable of synthesizing or modifying a small molecule, wherein one of the enzymes comprises a phytase enzyme encoded by a nucleic acid comprising a sequence of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions.

The invention provides a method for modifying a small molecule comprising the steps: (a) providing a phytase enzyme encoded by a nucleic acid comprising a sequence of the invention; (b) providing a small molecule; and (c) reacting the enzyme of step (a) with the small molecule of step (b) under conditions that facilitate an enzymatic reaction catalyzed by the phytase enzyme, thereby modifying a small molecule by a phytase enzymatic reaction. The method can comprise a plurality of small molecule substrates for the enzyme of step (a), thereby generating a library of modified small molecules produced by at least one enzymatic reaction catalyzed by the phytase enzyme. The can comprise a plurality of additional enzymes under conditions that facilitate a plurality of biocatalytic reactions by the enzymes to form a library of modified small molecules produced by the plurality of enzymatic reactions. The method can further comprise the step of testing the library to determine if a particular modified small molecule that exhibits a desired activity is present within the library.

In one aspect, the method comprises the step of testing the library by steps further comprising systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides a method for determining a functional fragment of a phytase enzyme comprising the steps of: (a) providing a phytase enzyme, wherein the enzyme comprises an amino acid sequence of the invention, or, is encoded by a nucleic acid having a sequence of the invention; and (b) deleting a plurality of amino acid residues from the sequence of step (a) and testing the remaining subsequence for a phytase activity, thereby determining a functional fragment of a phytase enzyme. The phytase activity can be measured by providing a phytase substrate and detecting an increase in the amount of the substrate or a decrease in the amount of a reaction product. In one aspect, a decrease in the amount of an enzyme substrate or an increase in the amount of the reaction product with the test compound is compared to the amount of substrate or reaction product without the test compound to identify the test compound as an activator of phytase activity.

The invention provides a method for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid comprising a sequence of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. The genetic composition of the cell can be modified by a method comprising deletion of a sequence or modification of a sequence in the cell, or, knocking out the expression of a gene. The method can further comprise selecting a cell comprising a newly engineered phenotype. The method can further comprise culturing the selected cell, thereby generating a new cell strain comprising a newly engineered phenotype.

The invention provides a method for hydrolyzing an inositol-hexaphosphate to inositol and inorganic phosphate comprising the following steps: (a) providing a polypeptide having a phytase activity, wherein the polypeptide comprises an amino acid sequence of the invention, or, a polypeptide encoded by a nucleic acid having a sequence of the invention; (b) providing a composition comprising an inositol-hexaphosphate; and (c) contacting the polypeptide of step (a) with the composition of step (b) under conditions wherein the polypeptide hydrolyzes the inositol-hexaphosphate to produce to inositol and inorganic phosphate. The conditions can comprise a temperature of between about 37° C. and about 70° C. The composition can comprise a phytic acid.

The invention provides a method for oil degumming comprising the following steps: (a) providing a polypeptide having a phytase activity, wherein the polypeptide comprises an amino acid sequence of the invention, or, a polypeptide encoded by a nucleic acid having a sequence of the invention; (b) providing a composition comprising a vegetable oil; and (c) contacting the polypeptide of step (a) and the vegetable oil of step (b) under conditions wherein the polypeptide can cleave an inositol-inorganic phosphate linkage, thereby degumming the oil.

The invention provides a method for producing an animal feed comprising the following steps: (a) transforming a plant, plant part or plant cell with a polynucleotide encoding a phytase enzyme polypeptide, wherein the phytase comprises at least thirty contiguous amino acids of a sequence of the invention, or a polypeptide encoded by a nucleic acid having a sequence of the invention, or a polypeptide having a sequence as set forth in SEQ ID NO: 2; (b) culturing the plant, plant part or plant cell under conditions in which the phytase enzyme is expressed; and (c) converting the plant, plant parts or plant cell into a composition suitable for feed for an animal, or adding the cultured plant, plant part or plant cell to an animal feed, thereby producing an animal feed. The polynucleotide can comprise an expression vector, wherein the vector comprises an expression control sequence capable of expression the nucleic acid in a plant cell. The animal can be a monogastric animal, e.g., a ruminant.

The invention provides a method for delivering a phytase enzyme supplement to an animal, said method comprising: (a) preparing an edible delivery matrix comprising an edible carrier and a phytase enzyme, wherein the matrix readily disperses and releases the phytase enzyme when placed into aqueous media, and (b) administering the edible enzyme delivery matrix to the animal. The edible delivery matrix can comprise a granulate edible carrier. The edible delivery matrix can be in the form of pellets, pills, tablets, and the like. The edible carrier can comprise a carrier selected from the group consisting of grain germ, hay, alfalfa, timothy, soy hull, sunflower seed meal and wheat meal. The edible carrier can comprise grain germ that is spent of oil. The phytase can comprise at least thirty contiguous amino acids of a sequence of the invention, or a polypeptide encoded by a nucleic acid having a sequence of the invention, or a polypeptide having a sequence as set forth in SEQ ID NO: 2. The phytase enzyme can be glycosylated to provide thermotolerance or thermostability at various conditions, e.g., at pelletizing conditions. The delivery matrix can be formed by pelletizing a mixture comprising a grain germ and the phytase enzyme to yield a particle. The pellets can be made under conditions comprising application of steam. The pellets can be made under conditions comprising application of a temperature in excess of 80° C. for about 5 minutes. The pellet can comprise a phytase enzyme that comprises a specific activity of at least 350 to about 900 units per milligram of enzyme.

The invention provides a method of increasing the resistance of a phytase polypeptide to enzymatic inactivation in a digestive system of an animal, the method comprising glycosylating a phytase polypeptide, wherein the phytase comprises at least thirty contiguous amino acids of a sequence of the invention, or a polypeptide encoded by a nucleic acid having a sequence of the invention, or a polypeptide having a sequence as set forth in SEQ ID NO: 2, thereby increasing resistance of the phytase polypeptide to enzymatic inactivation in a digestive system of an animal. The glycosylation can be N-linked glycosylation and/or O-linked glycosylation. The phytase polypeptide can be glycosylated as a result of in vitro expression, or in vivo expression of a polynucleotide encoding the phytase in a cell. The cell can be a eukaryotic cell, such as a fungal cell, a plant cell, an insect cell or a mammalian cell.

The invention provides a method of generating or increasing the thermotolerance or thermostability of a phytase polypeptide, the method comprising glycosylating a phytase polypeptide, wherein the phytase comprises at least thirty contiguous amino acids of a sequence of the invention, or a polypeptide encoded by a nucleic acid having a sequence of the invention, or a polypeptide having a sequence as set forth in SEQ ID NO: 2, thereby increasing the thermotolerance or thermostability of the phytase polypeptide. The phytase specific activity can be thermostable or thermotolerant at a temperature in the range from greater than about 37° C. to about 90° C.

The invention provides a method for processing of corn and sorghum kernels comprising the following steps: (a) providing a polypeptide having a phytase activity, wherein the polypeptide comprises an amino acid sequence of the invention, or, a polypeptide encoded by a nucleic acid having a sequence of the invention; (b) providing a composition comprising a corn steep liquor or a sorghum steep liquor; and (c) contacting the polypeptide of step (a) and the composition of step (b) under conditions wherein the polypeptide can cleave an inositol-inorganic phosphate linkage.

The invention provides a method for overexpressing a recombinant phytase in a cell comprising expressing a vector comprising a nucleic acid of the invention, e.g., a nucleic acid comprising a nucleic acid sequence at least 98% sequence identity to SEQ ID NO:1 over a region of at least about 100 residues, wherein the sequence identities are determined by analysis with a sequence comparison algorithm or by visual inspection, or, a nucleic acid that hybridizes under stringent conditions to a nucleic acid sequence as set forth in SEQ ID NO:1, or a subsequence thereof. The overexpression can be effected by any means, e.g., use of a high activity promoter, a dicistronic vector or by gene amplification of the vector.

The invention provides methods for generating a variant phytase having a desired activity by obtaining a nucleic acid comprising a polynucleotide sequence selected from a sequence encoding a phytase enzyme, a sequence substantially identical thereto, a sequence complementary thereto, and a fragment comprising at least 30 consecutive nucleotides thereof, and modifying one or more nucleotides in said sequence to another nucleotide, deleting one or more nucleotides in said sequence, or adding one or more nucleotides to said sequence. By such a method, a variant polynucleotide is obtained that encodes a modified phytase enzyme having a desired activity, such as enhanced thermostability or enhanced thermotolerance.

In still another aspect, the invention provides methods for delivering a phytase supplement to an animal by preparing an edible enzyme delivery matrix in the form of pellets comprising a granulate edible carrier and a thermotolerant recombinant phytase enzyme, wherein the particles readily disperse the phytase enzyme contained therein into aqueous media, and administering the edible enzyme delivery matrix to the animal.

In yet another aspect, the invention provides methods for increasing resistance of a phytase polypeptide to enzymatic inactivation in a digestive system of an animal comprising glycosylating a phytase polypeptide having an amino acid sequence as set forth in SEQ ID NO:2, or a conservative variation thereof, thereby increasing resistance of the phytase polypeptide to enzymatic inactivation in the digestive system of an animal.

In another aspect, the invention provides methods for utilizing phytase as a nutritional supplement in the diets of animals by preparing a nutritional supplement containing a recombinant phytase enzyme comprising at least thirty contiguous amino acids of SEQ ID NO:2, and administering the nutritional supplement to an animal to increase the utilization of phytate contained in food ingested by the animal.

In yet another aspect, the invention provides methods of increasing thermotolerance of a phytase polypeptide, the method comprising glycosylating a phytase polypeptide, or a conservative variation thereof, so as to thereby increase thermotolerance of the phytase polypeptide.

In still another aspect, the invention provides a thermostable phytase polypeptide, said thermotolerant phytase polypeptide being glycosylated so as to provide increased specific activity of the phytase polypeptide after exposure to a temperature in the range from greater than 37° C. to about 90° C. compared to a corresponding substantially non-glycosylated phytase polypeptide.

In yet another aspect, the invention feed composition comprising a recombinant phytase protein having at least thirty contiguous amino acids of the amino acid sequence set forth in SEQ ID NO:2, or a conservative variation thereof, and a phytate-containing foodstuff.

The details of one or more aspects of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

FIG. 1A shows the nucleotide sequence for a modified phytase (SEQ ID NO:1).

FIG. 1B shows the amino acid sequence for a modified phytase (SEQ ID NO:2).

FIG. 5 is a table presenting data from experiments designed to determine the relative half life of phytase from E. coli, P. pastoris, and S. cerevisiae after exposure to pepsin as a simulated gastric intestinal fluid.

FIG. 6 presents the amino acid sequence of a phytase enzyme (amino acid residues 2–432 of SEQ ID NO:2) with the predicted glycosylation sites in bold.

FIG. 7 presents in table format the results obtained from analysis on a 12% Tris-Glycine Gel of P. pastoris and S. cerevisiae phytase protein digested with O-glycosidase and Endo H.

FIG. 9A presents the amino acid sequence of SEQ ID NO:2 (amino acid residues 2–432 of SEQ ID NO:2) phytase expressed in P. pastoris with the glycosylated residues as determined experimentally indicated in bold in the partial sequence of SEQ ID NO:4.

FIG. 9B presents the amino acid sequence of SEQ ID NO:2 (amino acid residues 2–432 of SEQ ID NO:2) phytase expressed in S. cerevisiae with the glycosylated residues as determined experimentally indicated in bold in the partial sequence of SEQ ID NO:4.

FIG. 10 presents a summary of the results of glycosylation mapping for the phytase of FIGS. 9A and 9B with a partial sequence of SEQ ID NO:4.

FIG. 13 shows the nucleotide sequence encoding the wild type E. coli appA phytase (SEQ ID NO:3).

FIG. 14 shows the amino acid sequences for the wild type E. coli appA phytase polypeptide (SEQ ID NO:4).

DETAILED DESCRIPTION OF THE INVENTION

Figure 2A:
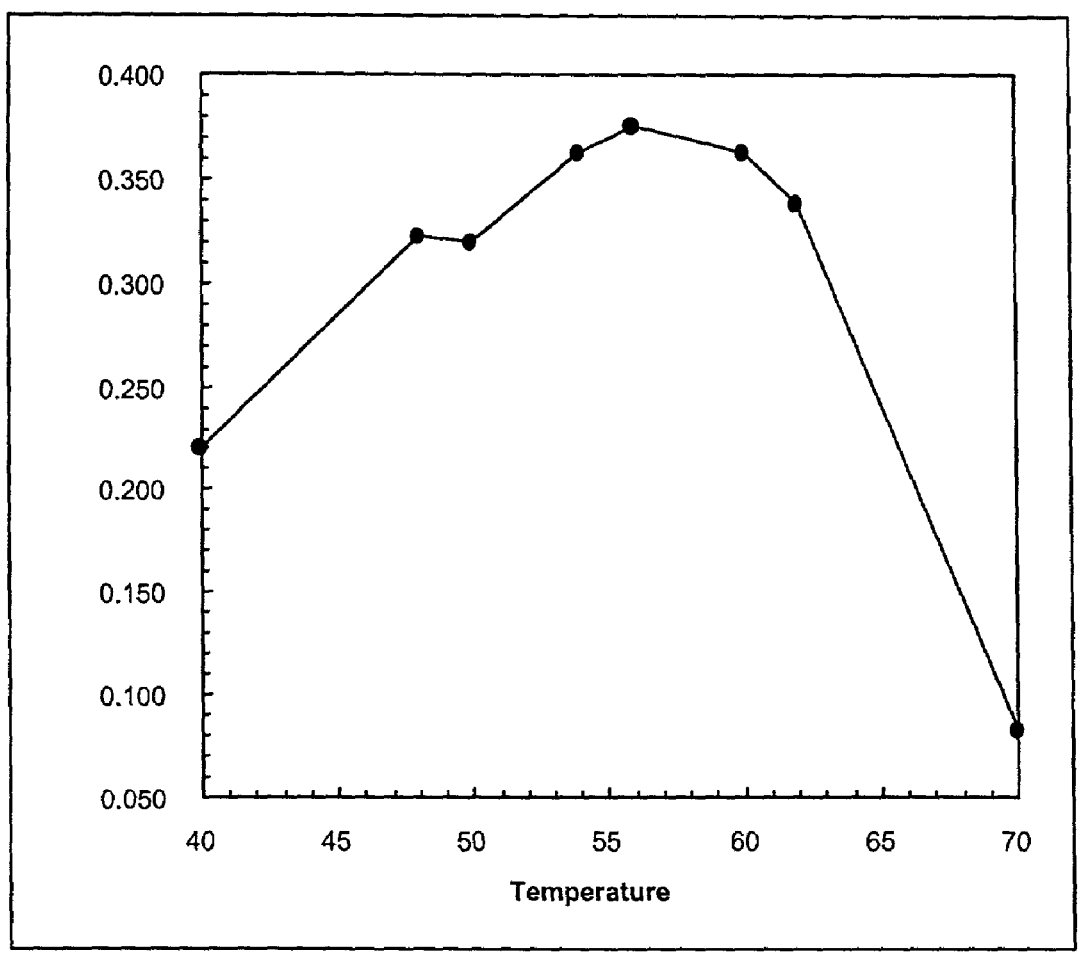
FIGS. 2A and 2B show the pH and temperature profile and stability data for the phytase enzyme of the present invention (SEQ ID NO:2). OD at 700 nm is indicated on the Y-axis of the graphs in FIG. 2. Temperature or pH is indicated on the X-axis of the graphs.
Figure 2B:
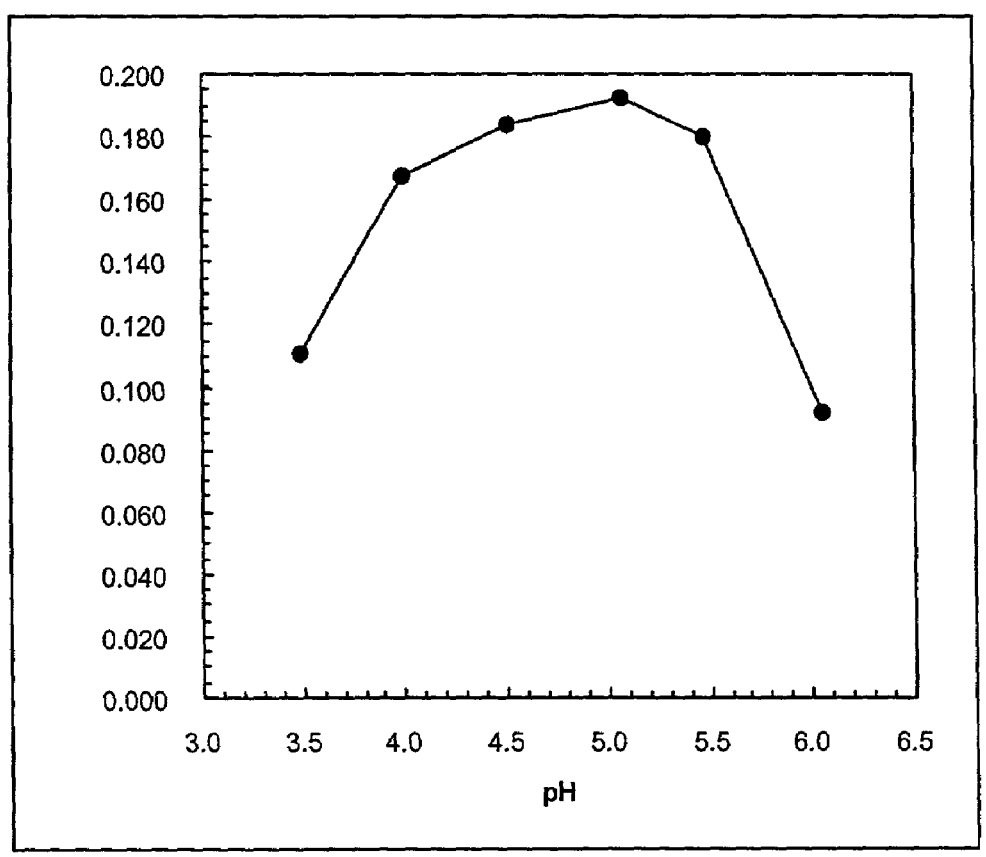

The invention relates to phytase polypeptides (e.g., SEQ ID NO:2) and polynucleotides (e.g., SEQ ID NO: 1) encoding them as well as methods of use of the polynucleotides and polypeptides. The terminology "phytase" encompasses enzymes having any phytase activity, for example, enzymes capable of catalyzing the degradation of phytate, e.g., the catalysis of phytate (myo-inositol-hexaphosphate) to inositol and inorganic phosphate. The phytases of the invention include thermotolerant and thermoresistant enzymes. A deposit of the gene designated 819PH59 (SEQ ID NO:1) in E. coli XL1-Blue, has been made with and accepted by the ATCC located at 10801 University Blvd., Manassas, Va. 20110-2209, on Nov. 26, 2002. The Patent Deposit Designation is PTA-4822.

The phytases and polynucleotides encoding the phytases of the invention are useful in a number of processes, methods, and compositions. For example, as discussed above, a phytase can be used in animal feed, and feed supplements as well as in treatments to degrade or remove excess phytate from the environment or a sample. Other uses will be apparent to those of skill in the art based upon the teachings provided herein, including those discussed above.

In one aspect, phytase molecules of the invention—either alone or in combination with other reagents (including but not limited to enzymes, including proteases)—are used in the processing of foodstuffs, e.g., for prevention of the unwanted corn sludge, and in other applications where phytate hydrolysis is desirable. In one aspect, phytase molecules of the invention are used to eliminate or decrease the presence of unhydrolyzed phytate, especially where unhydrolyzed phytate leads to problematic consequences in ex vivo processes including—but not limited to—the processing of foodstuffs. In one aspect, phytase molecules of the invention are used in procedures as described in EP0321004-B1 (Vaara et al.), including steps in the processing of corn and sorghum kernels whereby the hard kernels are steeped in water to soften them. Water-soluble substances that leach out during this process become part of a corn steep liquor, which is concentrated by evaporation. Unhydrolyzed phytic acid in the corn steep liquor, largely in the form of calcium and magnesium salts, is associated with phosphorus and deposits an undesirable sludge with proteins and metal ions. This sludge is problematic in the evaporation, transportation and storage of the corn steep liquor. Phytase molecules of the invention are used to hydrolyze this sludge.

The phytase molecules of the invention provide substantially superior commercial performance than previously identified phytase molecules, e.g. phytase molecules of fungal origin.

The phytase activity of the enzymes of the invention can be approximately 4400 U/mg. This corresponds to about a 40-fold or better improvement in activity of previously reported microbial enzymes has been approximately in the range of 50–100 U/mg protein.

The invention also provides methods for changing the characteristics of a phytase of the invention by mutagenesis and other method, including directed evolution, e.g., Diversa Corporation's proprietary approaches (e.g., DirectEvolution™). These approaches are further elaborated in U.S. Pat. No. 5,830,696. In brief, DirectEvolution™ comprises: a) the subjection of one or more molecular templates, e.g., the phytase nucleic acids of the invention, to mutagenesis to generate novel molecules, and b) the selection among these progeny species of novel molecules with more desirable characteristics.

The power of directed evolution depends on the starting choice of starting templates (e.g., SEQ ID NO:1), as well as on the mutagenesis process(es) chosen and the screening process(es) used. Thus, the invention provides novel highly active, physiologically effective, and economical sources of phytase activity, including novel phytases that: a) have superior activities under one or more specific applications, such as high temperature manufacture of foodstuffs, and are thus useful for optimizing these specific applications; b) are useful as templates for directed evolution to achieve even further improved novel molecules; and c) are useful as tools for the identification of additional related molecules by means such as hybridization-based approaches.

Definitions

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267–273; Yarmush (1992) J. Biochem. Biophys. Methods 25:85–97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below.

A "coding sequence of" or a "sequence encodes" a particular polypeptide or protein, is a nucleic acid sequence which is transcribed and translated into a polypeptide or protein when placed under the control of appropriate regulatory sequences.

The term "expression cassette" as used herein refers to a nucleotide sequence which is capable of affecting expression of a structural gene (i.e., a protein coding sequence, such as a phytase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid that can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

"Amino acid" or "amino acid sequence" as used herein refer to an oligopeptide, peptide, polypeptide, or protein sequence, or to a fragment, portion, or subunit of any of these, and to naturally occurring or synthetic molecules.

As used herein, the term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" means that the nucleic acid is adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 15%, 20%, 30%, 40%, 50%, 60%, 70%, 80%, 90% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence is "operably linked to" a coding sequence when RNA polymerase which initiates transcription at the promoter will transcribe the coding sequence into mRNA, as discussed further, below.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acids or polypeptides, refers to two or more sequences that have at least 50%, 60%, 70%, 75%, 80%, 85%, 90%, 95%, 98% or 99% nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:2, over a region of at least about 100 residues, 150 residues, 200 residues, 300 residues, 400 residues, or a region ranging from between about 50 residues to the full length of the nucleic acid or polypeptide. Nucleic acid sequences of the invention can be substantially identical over the entire length of a polypeptide coding region.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a phytase polypeptide, resulting in modification of the structure of the polypeptide, without significantly altering its biological activity. For example, amino- or carboxyl-terminal amino acids that are not required for phytase biological activity can be removed. Modified polypeptide sequences of the invention can be assayed for phytase biological activity by any number of methods, including contacting the modified polypeptide sequence with a phytase substrate and determining whether the modified polypeptide decreases the amount of specific substrate in the assay or increases the bioproducts of the enzymatic reaction of a functional phytase with the substrate, as discussed further, below.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

The term "variant" refers to polynucleotides or polypeptides of the invention modified at one or more base pairs, codons, introns, exons, or amino acid residues (respectively) yet still retain the biological activity of a phytase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant phytases having activity at a pH or temperature, for example, that is different from a wild-type phytase, are included herein.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. In one aspect, a "nucleic acid sequence" of the invention includes, for example, a sequence encoding a polypeptide as set forth in SEQ ID NO:2, and variants thereof. In another aspect, a "nucleic acid sequence" of the invention includes, for example, a sequence as set forth in SEQ ID NO:1, sequences complementary thereto, fragments of the foregoing sequences and variants thereof.

A "coding sequence" or a "nucleotide sequence encoding" a particular polypeptide or protein, is a nucleic acid sequence which is transcribed and translated into a polypeptide or protein when placed under the control of appropriate regulatory sequences.

The term "gene" means the segment of DNA involved in producing a polypeptide chain; it includes regions preceding and following the coding region (leader and trailer) as well as, where applicable, intervening sequences (introns) between individual coding segments (exons).

"Amino acid" or "amino acid sequence" as used herein refer to an oligopeptide, peptide, polypeptide, or protein sequence, or to a fragment, portion, or subunit of any of these, and to naturally occurring or synthetic molecules. In one aspect, an "amino acid sequence" or "polypeptide sequence" of the invention includes, for example, a sequence as set forth in SEQ ID NO:2, fragments of the foregoing sequence and variants thereof. In another aspect, an "amino acid sequence" of the invention includes, for example, a sequence encoded by a polynucleotide having a sequence as set forth in SEQ ID NO:1, sequences complementary thereto, fragments of the foregoing sequences and variants thereof.

The term "polypeptide" as used herein, refers to amino acids joined to each other by peptide bonds or modified peptide bonds, i.e., peptide isosteres, and may contain modified amino acids other than the 20 gene-encoded amino acids. The polypeptides may be modified by either natural processes, such as post-translational processing, or by chemical modification techniques that are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. (See *Proteins—Structure and Molecular Properties* 2$^{nd}$ Ed., T. E. Creighton, W.H. Freeman and Company, New York (1993); *Posttranslational Covalent Modification of Proteins*, B. C. Johnson, Ed., Academic Press, New York, pp. 1–12 (1983)).

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$–$10^6$ fold. However, the term "purified" also includes nucleic acids which have been purified from the remainder of the genomic DNA or from other sequences in a library or other environment by at least one order of magnitude, typically two or three orders, and more typically four or five orders of magnitude.

As used herein, the term "recombinant" means that the nucleic acid is adjacent to "backbone" nucleic acid to which it is not adjacent in its natural environment. Additionally, to be "enriched" the nucleic acids will represent 5% or more of the number of nucleic acid inserts in a population of nucleic acid backbone molecules. Backbone molecules according to the invention include nucleic acids such as expression vectors, self-replicating nucleic acids, viruses, integrating nucleic acids, and other vectors or nucleic acids used to maintain or manipulate a nucleic acid insert of interest. Typically, the enriched nucleic acids represent 15% or more of the number of nucleic acid inserts in the population of recombinant backbone molecules. More typically, the enriched nucleic acids represent 50% or more of the number of nucleic acid inserts in the population of recombinant backbone molecules. In one aspect, the enriched nucleic acids represent 90% or more of the number of nucleic acid inserts in the population of recombinant backbone molecules.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B., J. Am. Chem. Soc., 85:2149–2154, 1963) (See also Stewart, J. M. and Young, J. D., Solid Phase Peptide Synthesis, 2 ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

A promoter sequence is "operably linked to" a coding sequence when RNA polymerase which initiates transcription at the promoter will transcribe the coding sequence into mRNA.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the gel electrophoresis may be performed to isolate the desired fragment.

"Oligonucleotide" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

The phrase "substantially identical" in the context of two nucleic acid sequences or polypeptides, refers to two or more sequences that have at least 60%, 70%, 80%, and in some aspects 90–95% nucleotide or amino acid residue identity, when compared and aligned for maximum correspondence, as measured using one of the known sequence comparison algorithms or by visual inspection. Typically, the substantial identity exists over a region of at least about 100 residues, and most commonly the sequences are substantially identical over at least about 150–200 residues. In some aspects, the sequences are substantially identical over the entire length of the coding regions.

The term "about" is used herein to mean "approximately," or "roughly," or "around," or "in the region of." When the term "about" is used in conjunction with a numerical range, it modifies that range by extending the boundaries above and below the numerical values set forth. In general, the term "about" is used herein to modify a numerical value above and below the stated value by a variance of 20 percent.

Additionally a "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a phytase polypeptide, resulting in modification of the structure of the polypeptide, without significantly altering its biological activity. For example, amino- or carboxyl-terminal amino acids that are not required for phytase biological activity can be removed. Modified polypeptide sequences of the invention can be assayed for phytase biological activity by any number of methods, including contacting the modified polypeptide sequence with an phytase substrate and determining whether the modified polypeptide decreases the amount of specific substrate in the assay or increases the bioproducts of the enzymatic reaction of a functional phytase polypeptide with the substrate.

"Fragments" as used herein are a portion of a naturally occurring or recombinant protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related. In general two amino acid sequences are "substantially the same" or "substantially homologous" if they are at least about 70, but more typically about 85% or more identical. Fragments which have different three dimensional structures as the naturally occurring protein are also included. An example of this, is a "pro-form" molecule, such as a low activity proprotein that can be modified by cleavage to produce a mature enzyme with significantly higher activity.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "variant" refers to polynucleotides or polypeptides of the invention modified at one or more base pairs, codons, introns, exons, or amino acid residues (respectively) yet still retain the biological activity of an phytase of the invention. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM and any combination thereof.

The terms "thermostable" and "thermostability" as used herein with reference to an enzyme mean the ability of the enzyme to function at increased temperatures, for example to have comparable specific activity at 70° C. and at 85° C. at a common pH. A "thermostable" enzyme will maintain much or all of its activity at an increased temperature or may be more active at an increased temperature than at its normal temperature (e.g., room temperature) or its optimum temperature prior to mutagenesis to obtain enhanced thermostability.

The terms "thermotolerant" and "thermotolerance" as used herein with reference to an enzyme mean the ability of the enzyme to function normally after exposure to high temperature, even though the high temperature may temporarily deactivate the enzyme.

Generating and Manipulating Nucleic Acids

The invention provides nucleic acids, including expression cassettes such as expression vectors, encoding the polypeptides and phytases of the invention. The invention also includes methods for discovering new phytase sequences using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333–335; yeast artificial chromosomes (YAC); bacterial artificial chromosomes (BAC); P1 artificial chromosomes, see, e.g., Woon (1998) Genomics 50:306–316; P1-derived vectors (PACs), see, e.g., Kern (1997) Biotechniques 23:120–124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lac, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing, or over-expressing, a polypeptide in bacteria include the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Expression Vectors and Cloning Vehicles

The invention provides expression vectors and cloning vehicles comprising nucleic acids of the invention, e.g., sequences encoding the phytases of the invention, for expression, and over-expression, of the polypeptides of the invention (and nucleic acids, e.g., antisense). Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector may comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Host Cells and Transformed Cells

The invention also provides a transformed cell comprising a nucleic acid sequence of the invention, e.g., a sequence encoding a phytase of the invention, a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include E. coli, Streptomyces, Bacillus subtilis, Salmonella typhimurium and various species within the genera Pseudomonas, Streptomyces, and Staphylococcus. Exemplary insect cells include Drosophila S2 and Spodoptera Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express, or overexpress, recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Amplification of Nucleic Acids

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides with a phytase activity, where the primer pairs are capable of amplifying nucleic acid sequences including the exemplary SEQ ID NO:1, or a subsequence thereof. One of skill in the art can design amplification primer sequence pairs for any part of or the full length of these sequences; for example:

The exemplary SEQ ID NO:1 is

ATGAAAGCGATCTTAATCCCATTTTTATCTCTTCTGATTCCGTTAACCCC

GCAATCTGCATTCGCTCAGAGTGAGCCGGAGCTGAAGCTGGAAAGTGTGG

TGATTGTCAGTCGTCATGGTGTGCGTGCTCCAACCAAGGCCACGCAACTG

ATGCAGGATGTCACCCCAGACGCATGGCCAACCTGGCCGGTAAAACTGGG

TGAGCTGACACCGCGCGGTGGTGAGCTAATCGCCTATCTCGGACATTACT

GGCGTCAGCGTCTGGTAGCCGACGGATTGCTGCCTAAATGTGGCTGCCCG

CAGTCTGGTCAGGTCGCGATTATTGCTGATGTCGACGAGCGTACCCGTAA

AACAGGCGAAGCCTTCGCCGCCGGGCTGGCACCTGACTGTGCAATAACCG

TACATACCCAGGCAGATACGTCCAGTCCCGATCCGTTATTTAATCCTCTA

AAAACTGGCGTTTGCCAACTGGATAACGCGAACGTGACTGACGCGATCCT

CGAGAGGGCAGGAGGGTCAATTGCTGACTTTACCGGGCATTATCAAACGG

CGTTTCGCGAACTGGAACGGGTGCTTAATTTTCCGCAATCAAACTTGTGC

CTTAAACGTGAGAAACAGGACGAAAGCTGTTCATTAACGCAGGCATTACC

```
                      -continued
ATCGGAACTCAAGGTGAGCGCCGACTGTGTCTCATTAACCGGTGCGGTAA

GCCTCGCATCAATGCTGACGGAGATATTTCTCCTGCAACAAGCACAGGGA

ATGCCGGAGCCGGGGTGGGGAAGGATCACCGATTCACACCAGTGGAACAC

CTTGCTAAGTTTGCATAACGCGCAATTTGATTTGCTACAACGCACGCCAG

AGGTTGCCCGCAGCCGCGCCACCCCGTTATTAGATTTGATCAAGACAGCG

TTGACGCCCCATCCACCGCAAAAACAGGCGTATGGTGTGACATTACCCAC

TTCAGTGCTGTTTATCGCCGGACACGATACTAATCTGGCAAATCTCGGCG

GCGCACTGGAGCTCAACTGGACGCTTCCCGGTCAGCCGGATAACACGCCG

CCAGGTGGTGAACTGGTGTTTGAACGCTGGCGTCGGCTAAGCGATAACAG

CCAGTGGATTCAGGTTTCGCTGGTCTTCCAGACTTTACAGCAGATGCGTG

ATAAAACGCCGCTGTCATTAAATACGCCGCCCGGAGAGGTGAAACTGACC

CTGGCAGGATGTGAAGAGCGAAATGCGCAGGGCATGTGTTCGTTGGCAGG

TTTTACGCAAATCGTGAATGAAGCACGCATACCGGCGTGCAGTTTGAGAT

CTCATCTA
```

Thus an exemplary amplification primer sequence pair is residues 1 to 21 of SEQ ID NO:1 (i.e., ATGAAAGC-GATCTTAATCCCA) and the complementary strand of the last 21 residues of SEQ ID NO:1 (i.e., the complementary strand of TGCAGTTTGAGATCTCATCTA).

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

Determining the Degree of Sequence Identity

The invention provides an isolated or recombinant nucleic acid comprising a nucleic acid sequence having at least 98% sequence identity to SEQ ID NO:1 over a region of at least about 100 residues, wherein the nucleic acids encode at least one polypeptide having a phytase activity and the sequence identities are determined by analysis with a sequence comparison algorithm or by a visual inspection. In alternative embodiments the nucleic acid sequence has at least 98%, 98.5%, 99% or 99.5% sequence identity to SEQ ID NO:1 over a region of at least about 50 residues, 100 residues, 150 residues, 200 residues, 250 residues, 300 residues, 350 residues, 400 residues, 450 residues, 500 residues, 550 residues, 600 residues, 700 residues, 800 residues, 900 residues, 1000 residues, 1200 residues or 1300 residues. The nucleic acid sequence can have a sequence as set forth in SEQ ID NO:1. In one aspect, the extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W.H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444–2448, 1988; Altschul et al., J. Mol. Biol. 215(3):403–410, 1990; Thompson et al., Nucleic Acids Res. 22(2):4673–4680, 1994; Higgins et al., Methods Enzymol. 266:383–402, 1996; Altschul et al., J. Mol. Biol. 215(3):403–410, 1990; Altschul et al., Nature Genetics 3:266–272, 1993.

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence SEQ ID NO:1, SEQ ID NO:2) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous residues. For example, in alternative aspects of the invention, continuous residues ranging anywhere from 20 to the full length of exemplary sequences SEQ ID NO:1, SEQ ID NO:2 are compared to a reference sequence of the same number of contiguous positions after the two sequences are optimally aligned. If the reference sequence has the requisite sequence identity to SEQ ID NO:1, SEQ ID NO:2, e.g., 98% sequence identity to SEQ ID NO:1, SEQ ID NO:2, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389–3402; Altschul (1990) J. Mol. Biol. 215:403–410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, less than about 0.01, or less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which can be obtained from a protein or nucleic acid sequence database. High-scoring segment pairs can be identified (i.e., aligned) by means of a scoring matrix, many of which are known in the art. An exemplary scoring matrix used is the BLOSUM62 matrix (Gonnet et al., Science 256:1443–1445, 1992; Henikoff and Henikoff, Proteins 17:49–61, 1993). Alternatively, the PAM or PAM250 matrices may be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used. default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention include:
"Filter for low complexity: ON
>Word Size: 3
>Matrix: Blosum62
>Gap Costs: Existence:11
>Extension:1"
"Filter for low complexity: ON Other default settings are: filter for low complexity OFF, word size of 3 for protein, BLOSUM62 matrix, gap existence penalty of −11 and a gap extension penalty of −1.

An exemplary NCBI BLAST 2.2.2 program setting is set forth in Example 1, below. Note that the "-W" option defaults to 0. This means that, if not set, the word size defaults to 3 for proteins and 11 for nucleotides.

Computer Systems and Computer Program Products

To determine and identify sequence identities, structural homologies, motifs and the like in silico the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention, e.g., the exemplary sequences SEQ ID NO:1, SEQ ID NO:2. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Figure 15:
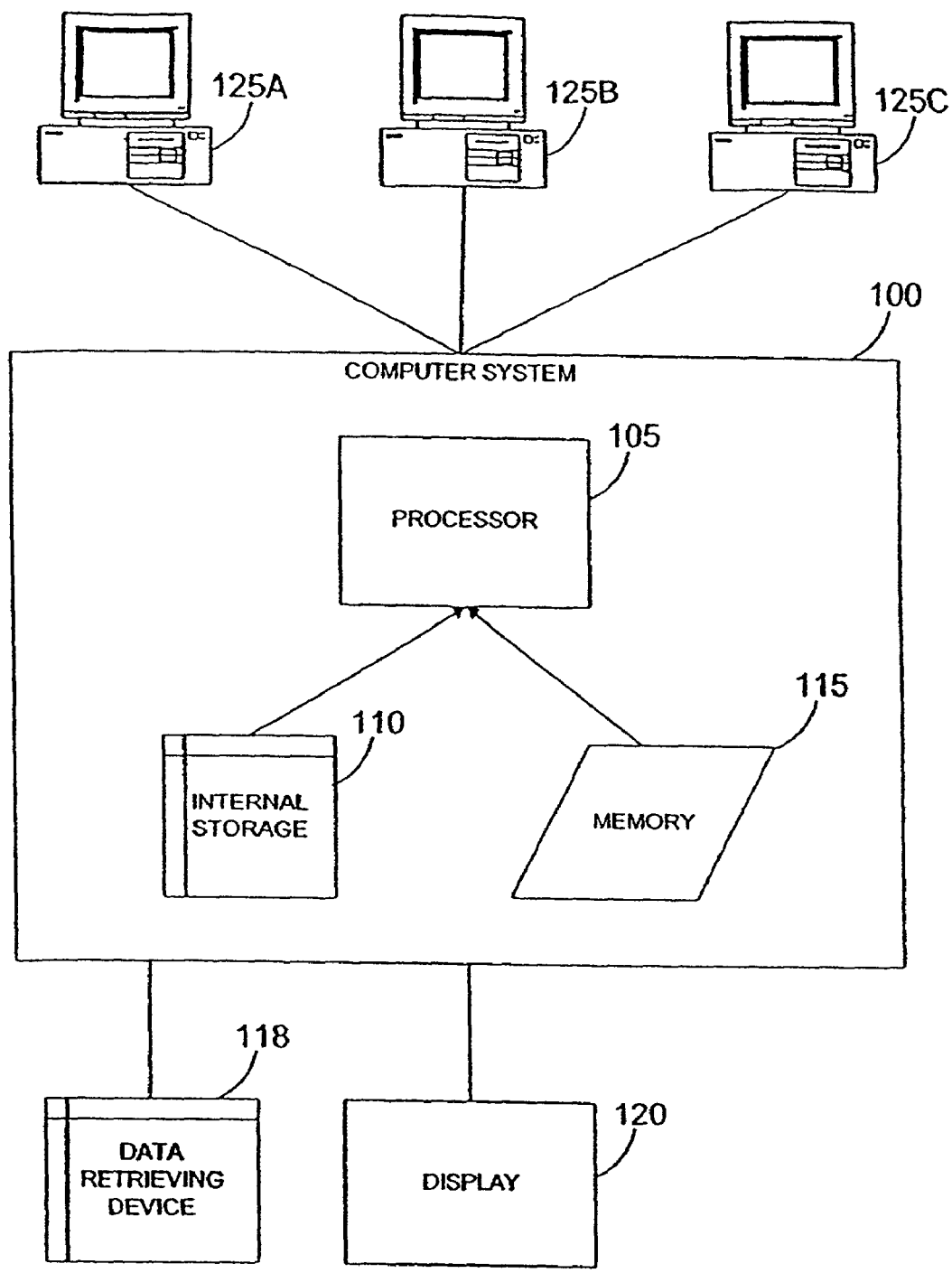
FIG. 15 is a block diagram of a computer system, as described in detail, below.

Aspects of the invention include systems (e.g., internet based systems), particularly computer systems, which store and manipulate the sequences and sequence information described herein. One example of a computer system 100 is illustrated in block diagram form in FIG. 15. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (can be implemented as RAM) and one or more internal data storage devices 110, such as a hard drive and/or other computer readable media having data recorded thereon. The computer system 100 can further include one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a–c in a network or wide area network to provide centralized access to the computer system 100. Software for accessing and processing the nucleotide or amino acid sequences of the invention can reside in main memory 115 during execution.

In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of an exemplary sequence SEQ ID NO:1, SEQ ID NO:2, stored on a computer readable medium to reference sequences stored on a computer readable medium to identify homologies or structural motifs.

Figure 16:
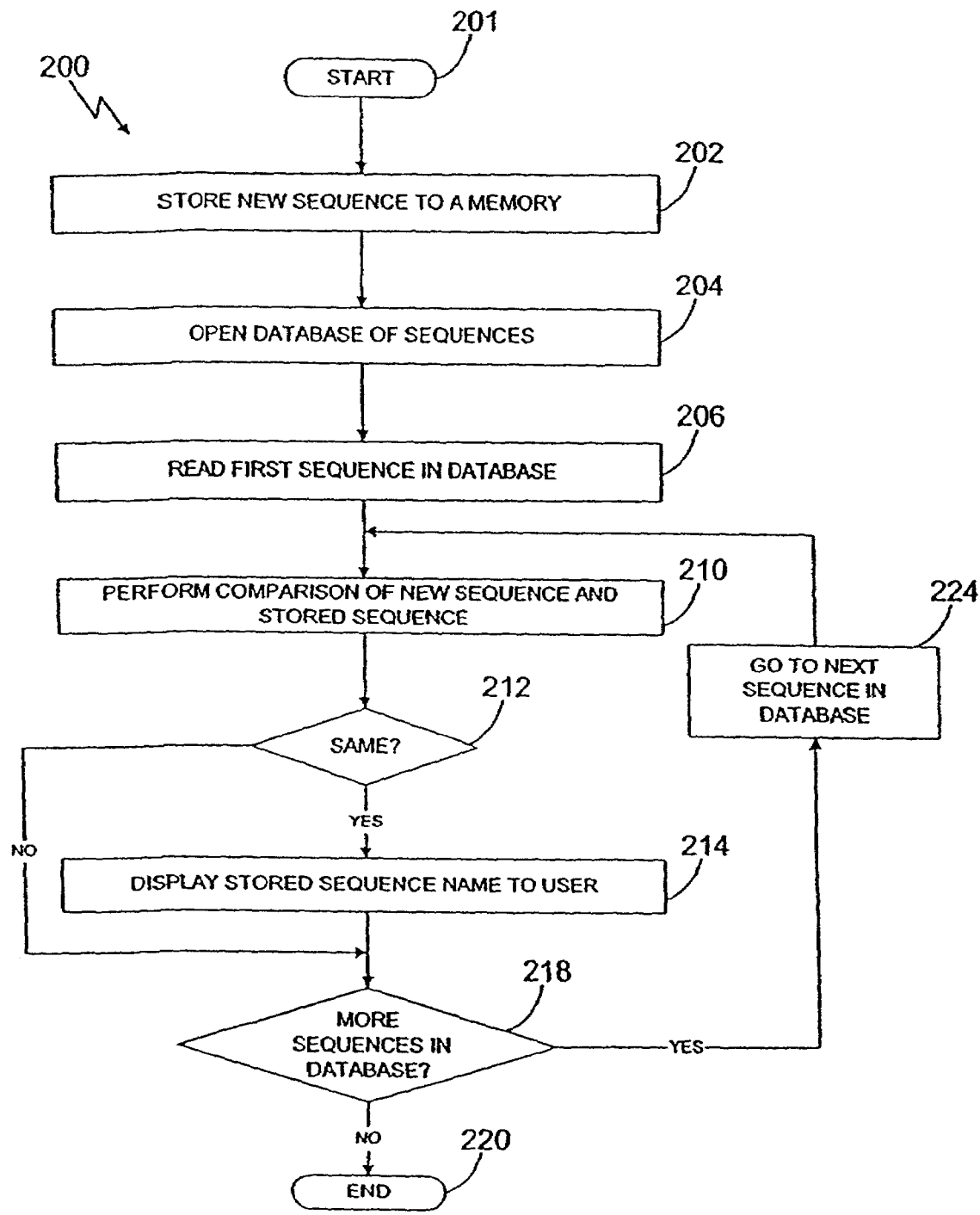
FIG. 16 is a flow diagram illustrating one aspect of a process 200 for comparing a new nucleotide or protein sequence with a database of sequences in order to determine the homology levels between the new sequence and the sequences in the database, as described in detail, below.

The parameters used with the above algorithms may be adapted depending on the sequence length and degree of homology studied. In some aspects, the parameters may be the default parameters used by the algorithms in the absence of instructions from the user. FIG. 16 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes.

Figure 17:
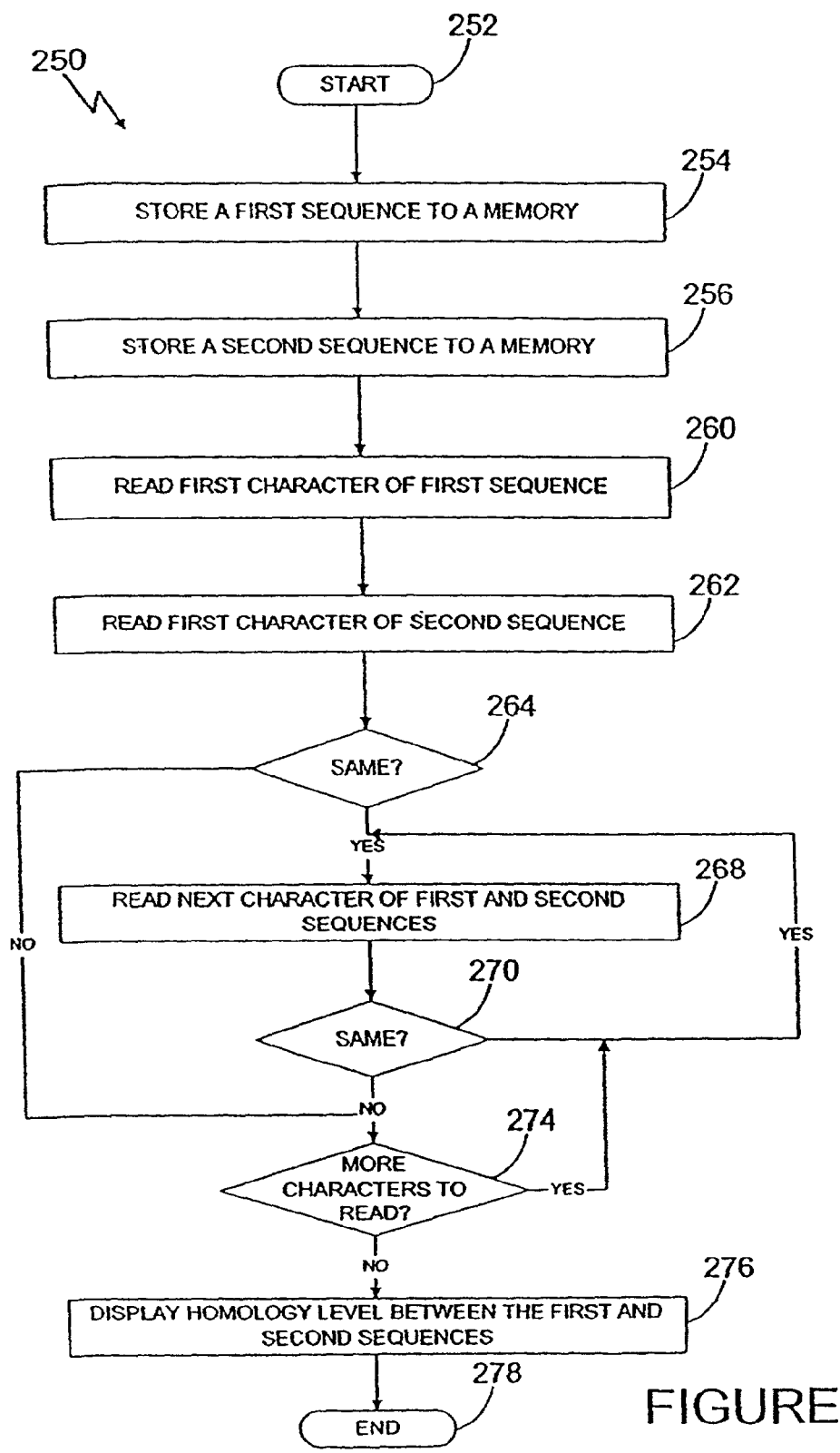
FIG. 17 is a flow diagram illustrating one embodiment of a process in a computer for determining whether two sequences are homologous, as described in detail, below.

FIG. 17 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 17. The method can be performed by reading a sequence of the invention and the reference sequences through the use of the computer program and identifying differences with the computer program.

Figure 18:
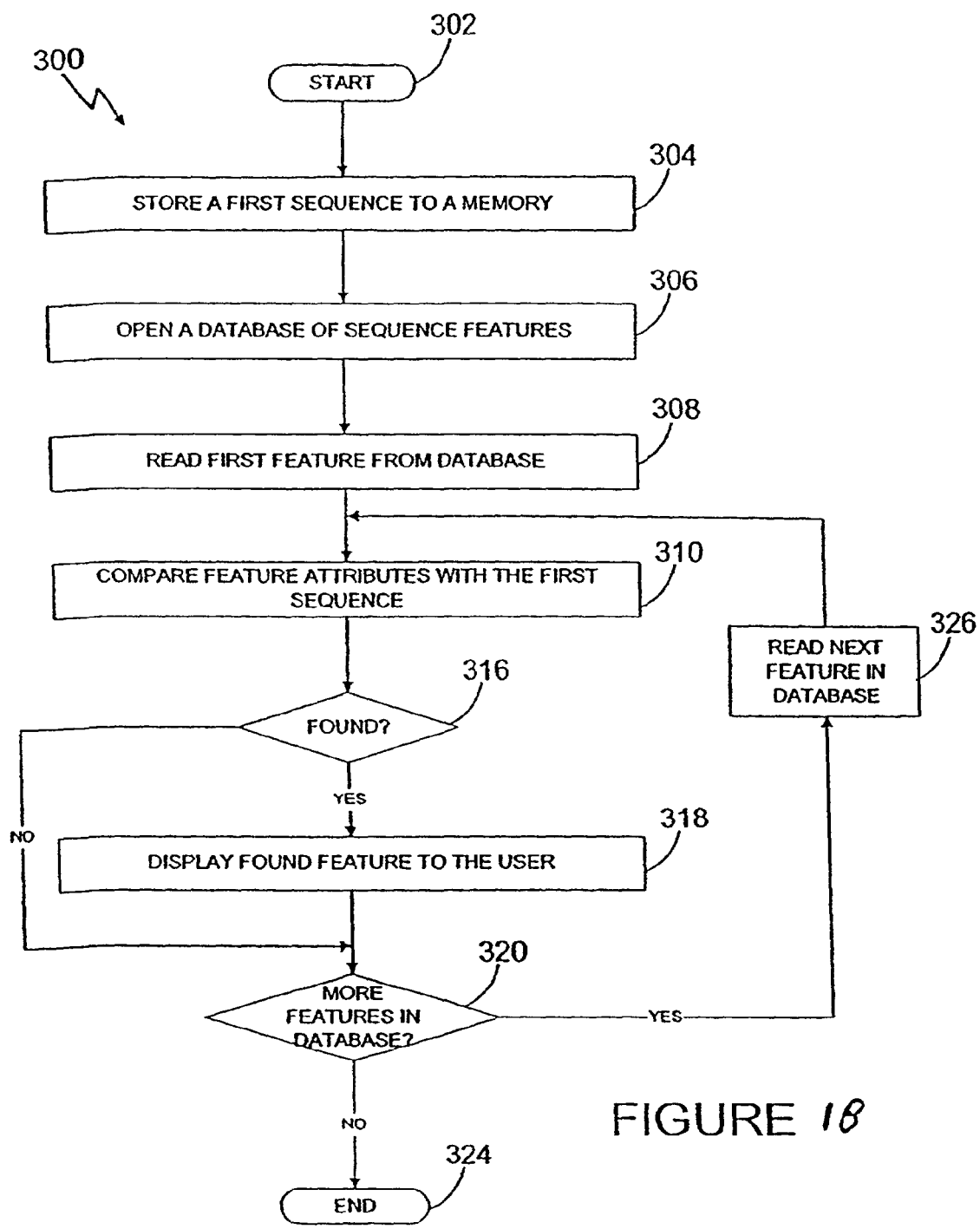
FIG. 18 is a flow diagram illustrating one aspect of an identifier process for detecting the presence of a feature in a sequence, as described in detail, below.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 18 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence.

If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention may be stored and manipulated in a variety of data processor programs in a variety of formats. For example, a sequence can be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237–245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, e.g., a sequence as set forth in SEQ ID NO:1, or a nucleic acid that encodes a polypeptide comprising a sequence as set forth in SEQ ID NO:2. The stringent conditions can be highly stringent conditions, medium stringent conditions, low stringent conditions, including the high and reduced stringency conditions described herein. In alternative embodiments, nucleic acids of the invention as defined by their ability to hybridize under stringent conditions can be between about five residues and the full length of the molecule of SEQ ID NO:1; e.g., they can be at least 5, 10, 15, 20, 25, 30, 35, 40, 50, 55, 60, 65, 70, 75, 80, 90, 100, 150, 200, 250, 300, 350, 400 residues in length. Nucleic acids shorter than full length are also included. These nucleic acids are useful as, e.g., hybridization probes, labeling probes, PCR oligonucleotide probes, iRNA, antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

Oligonucleotides Probes and Methods for Using Them

The invention also provides nucleic acid probes for identifying nucleic acids encoding a polypeptide with a phytase activity. In one aspect, the probe comprises at least 10 consecutive bases of a sequence as set forth in SEQ ID NO:1. Alternatively, a probe of the invention can be at least about 5, 6, 7, 8 or 9 to about 40, about 10 to 50, about 20 to 60 about 30 to 70, consecutive bases of a sequence as set forth in SEQ ID NO:1. The probes identify a nucleic acid by binding or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH2PO4, pH 7.0, 5.0 mM Na2EDTA, 0.5% SDS, 10× Denhardt's, and 0.5 mg/ml polyriboadenylic acid. Approximately 2×10$^7$ cpm (specific activity 4–9×10$^8$ cpm/ug) of $^{32}$P end-labeled oligonucleotide probe are then added to the solution. After 12–16 hours of incubation, the membrane is washed for 30 minutes at room temperature (RT) in 1×SET (150 mM NaCl, 20 mM Tris hydrochloride, pH 7.8, 1 mM Na2EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41(fraction G+C)−(0.63% formamide)−(600/N) where N is the length of the probe. Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, or 500 consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acids of the invention.

Additionally, the probes and methods of the invention may be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters, or a BLAST 2.2.2 program with exemplary settings as set forth herein).

Inhibiting Expression of a Phytase

The invention further provides for nucleic acids complementary to (e.g., antisense sequences to) the nucleic acid sequences of the invention. Antisense sequences are capable of inhibiting the transport, splicing or transcription of phytase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind phytase gene or message, in either case preventing or inhibiting the production or function of phytase enzyme. The association can be though sequence specific hybridization. Another useful class of inhibitors includes oligonucleotides which cause inactivation or cleavage of phytase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

The invention provides antisense oligonucleotides capable of binding phytase message which can inhibit phytase activity by targeting mRNA. Strategies for designing antisense oligonucleotides are well described in the scientific and patent literature, and the skilled artisan can design such phytase oligonucleotides using the novel reagents of the invention. For example, gene walking/RNA mapping protocols to screen for effective antisense oligonucleotides are well known in the art, see, e.g., Ho (2000) Methods Enzymol. 314:168–183, describing an RNA mapping assay, which is based on standard molecular techniques to provide an easy and reliable method for potent antisense sequence selection. See also Smith (2000) Euro. J. Pharm. Sci. 11:191–198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997) Toxicol Appl Pharmacol 144:189–197; Antisense Therapeutics, ed. Agarwal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense phytase sequences of the invention (see, e.g., Gold (1995) J. of Biol. Chem. 270:13581–13584).

Inhibitory Ribozymes

The invention provides for with ribozymes capable of binding phytase message which can inhibit phytase enzyme activity by targeting mRNA. Strategies for designing ribozymes and selecting the phytase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site. The enzymatic ribozyme RNA molecule can be formed in a hammerhead motif, but may also be formed in the motif of a hairpin, hepatitis delta virus, group I intron or RNaseP-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

Modification of Nucleic Acids

The invention provides methods of generating variants of the nucleic acids of the invention, e.g., those encoding a phytase enzyme. These methods can be repeated or used in various combinations to generate phytase enzymes having an altered or different activity or an altered or different stability from that of a phytase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods.

Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467–5471; or, combinatorial multiple cassette mutagenesis, see, e.g., Crameri (1995) Biotechniques 18:194–196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1–4; Ness (1999) Nature Biotechnology 17:893–896; Chang (1999) "Evolution of a cytokine using DNA family shuffling" Nature Biotechnology 17:793–797; Minshull (1999) "Protein evolution by molecular breeding" Current Opinion in Chemical Biology 3:284–290; Christians (1999) "Directed evolution of thymidine kinase for AZT phosphorylation using DNA family shuffling" Nature Biotechnology 17:259–264; Crameri (1998) "DNA shuffling of a family of genes from diverse species accelerates directed evolution" Nature 391:288–291; Crameri (1997) "Molecular evolution of an arsenate detoxification pathway by DNA shuffling," Nature Biotechnology 15:436–438; Zhang (1997) "Directed evolution of an effective fucosidase from a galactosidase by DNA shuffling and screening" Proc. Natl. Acad. Sci. USA 94:4504–4509; Patten et al. (1997) "Applications of DNA Shuffling to Pharmaceuticals and Vaccines" Current Opinion in Biotechnology 8:724–733; Crameri et al. (1996) "Construction and evolution of antibody-phage libraries by DNA shuffling" Nature Medicine 2:100–103; Crameri et al. (1996) "Improved green fluorescent protein by molecular evolution using DNA shuffling" Nature Biotechnology 14:315–319; Gates et al. (1996) "Affinity selective isolation of ligands from peptide libraries through display on a lac repressor 'headpiece dimer'" Journal of Molecular Biology 255:373–386; Stemmer (1996) "Sexual PCR and Assembly PCR" In: The Encyclopedia of Molecular Biology. VCH Publishers, New York. pp.447–457; Crameri and Stemmer (1995) "Combinatorial multiple cassette mutagenesis creates all the permutations of mutant and wildtype cassettes" BioTechniques 18:194–195; Stemmer et al. (1995) "Single-step assembly of a gene and entire plasmid form large numbers of oligodeoxyribonucleotides" Gene, 164:49–53; Stemmer (1995) "The Evolution of Molecular Computation" Science 270: 1510; Stemmer (1995) "Searching Sequence Space" Bio/Technology 13:549–553; Stemmer (1994) "Rapid evolution of a protein in vitro by DNA shuffling" Nature 370:389–391; and Stemmer (1994) "DNA shuffling by random fragmentation and reassembly: In vitro recombination for molecular evolution." Proc. Natl. Acad. Sci. USA 91:10747–10751.

Mutational methods of generating diversity include, for example, site-directed mutagenesis (Ling et al. (1997) "Approaches to DNA mutagenesis: an overview" Anal Biochem. 254(2): 157–178; Dale et al. (1996) "Oligonucleotide-directed random mutagenesis using the phosphorothioate method" Methods Mol. Biol. 57:369–374; Smith (1985) "In vitro mutagenesis" Ann. Rev. Genet. 19:423–462; Botstein & Shortle (1985) "Strategies and applications of in vitro mutagenesis" Science 229:1193–1201; Carter (1986) "Site-directed mutagenesis" Biochem. J. 237:1–7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488–492; Kunkel et al. (1987) "Rapid and efficient site-specific mutagenesis without phenotypic selection" Methods in Enzymol. 154, 367–382; and Bass et al. (1988) "Mutant Trp repressors with new DNA-binding specificities" Science 242:240–245); oligonucleotide-directed mutagenesis (Methods in Enzymol. 100: 468–500 (1983); Methods in Enzymol. 154: 329–350 (1987); Zoller & Smith (1982) "Oligonucleotide-directed mutagenesis using M13-derived vectors: an efficient and general procedure for the production of point mutations in any DNA fragment" Nucleic Acids Res. 10:6487–6500; Zoller & Smith (1983) "Oligonucleotide-directed mutagenesis of DNA fragments cloned into M13 vectors" Methods in Enzymol. 100:468–500; and Zoller & Smith (1987) "Oligonucleotide-directed mutagenesis: a simple method using two oligonucleotide primers and a single-stranded DNA template" Methods in Enzymol. 154: 329–350); phosphorothioate-modified DNA mutagenesis (Taylor et al. (1985) "The use of phosphorothioate-modified DNA in restriction enzyme reactions to prepare nicked DNA" Nucl. Acids Res. 13: 8749–8764; Taylor et al. (1985) "The rapid generation of oligonucleotide-directed mutations at high frequency using phosphorothioate-modified DNA" Nucl. Acids Res. 13: 8765–8787 (1985); Nakamaye (1986) "Inhibition of restriction endonuclease Nci I cleavage by phosphorothioate groups and its application to oligonucleotide-directed mutagenesis" Nucl. Acids Res. 14: 9679–9698; Sayers et al. (1988) "Y-T Exonucleases in phosphorothioate-based oligonucleotide-directed mutagenesis" Nucl. Acids Res. 16:791–802; and Sayers et al. (1988) "Strand specific cleavage of phosphorothioate-containing DNA by reaction with restriction endonucleases in the presence of ethidium bromide" Nucl. Acids Res. 16: 803–814); mutagenesis using gapped duplex DNA (Kramer et al. (1984) "The gapped duplex DNA approach to oligonucleotide-directed mutation construction" Nucl. Acids Res. 12: 9441–9456; Kramer & Fritz (1987) Methods in Enzymol. "Oligonucleotide-directed construction of mutations via gapped duplex DNA" 154:350–367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987–6999).

Additional protocols used in the methods of the invention include point mismatch repair (Kramer (1984) "Point Mismatch Repair" Cell 38:879–887), mutagenesis using repair-deficient host strains (Carter et al. (1985) "Improved oligonucleotide site-directed mutagenesis using M13 vectors" Nucl. Acids Res. 13: 4431–4443; and Carter (1987) "Improved oligonucleotide-directed mutagenesis using M13 vectors" Methods in Enzymol. 154: 382–403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415–423), mutagenesis by total gene synthesis (Nambiar et al. (1984) "Total synthesis and cloning of a gene coding for the ribonuclease S protein" Science 223: 1299–1301; Sakamar and Khorana (1988) "Total synthesis and expression of a gene for the a-subunit of bovine rod outer segment guanine nucleotide-binding protein (transducin)" Nucl. Acids Res. 14: 6361–6372; Wells et al. (1985) "Cassette mutagenesis: an efficient method for generation of multiple mutations at defined sites" Gene 34:315–323; and Grundstrom et al. (1985) "Oligonucleotide-directed mutagenesis by microscale 'shot-gun' gene synthesis" Nucl. Acids Res. 13: 3305–3316), double-strand break repair (Mandecki (1986); Arnold (1993) "Protein engineering for unusual environments" Current Opinion in Biotechnology 4:450–455. "Oligonucleotide-directed double-strand break repair in plasmids of *Escherichia coli*: a method for site-specific mutagenesis" Proc. Natl. Acad. Sci. USA, 83:7177–7181). Additional details on many of the above methods can be found in Methods in Enzymology Volume 154, which also describes useful controls for trouble-shooting problems with various mutagenesis methods. See also U.S. Pat. Nos. 5,605, 793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION" by del Cardayre et al., filed Jul. 15, 1998 (U.S. Ser. No. 09/166,188), and Jul. 15, 1999 (U.S. Ser. No. 09/354,922); "OLIGONUCLEOTIDE MEDIATED NUCLEIC ACID RECOMBINATION" by Crameri et al., filed Sep. 28, 1999 (U.S. Ser. No. 09/408,392), and "OLIGONUCLEOTIDE MEDIATED NUCLEIC ACID RECOMBINATION" by Crameri et al., filed Jan. 18, 2000 (PCT/US00/01203); "USE OF CODON-VARIED OLIGONUCLEOTIDE SYNTHESIS FOR SYNTHETIC SHUFFLING" by Welch et al., filed Sep. 28, 1999 (U.S. Ser. No. 09/408,393); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549).

Non-stochastic, or "directed evolution," methods include, e.g., saturation mutagenesis (GSSM), synthetic ligation reassembly (SLR), or a combination thereof are used to modify the nucleic acids of the invention to generate phytases with new or altered properties (e.g., activity under highly acidic or alkaline conditions, high temperatures, and the like). Polypeptides encoded by the modified nucleic acids can be screened for an activity before testing for an phytase or other activity. Any testing modality or protocol can be used, e.g., using a capillary array platform. See, e.g., U.S. Pat. Nos. 6,280,926; 5,939,250.

Saturation Mutagenesis, or, GSSM

In one aspect of the invention, non-stochastic gene modification, a "directed evolution process," is used to generate phytases with new or altered properties. Variations of this method have been termed "gene site-saturation mutagenesis," "site-saturation mutagenesis," "saturation mutagenesis" or simply "GSSM." It can be used in combination with other mutagenization processes. See, e.g., U.S. Pat. Nos. 6,171,820; 6,238,884. In one aspect, GSSM comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

Synthetic Ligation Reassembly (SLR)

The invention provides a non-stochastic gene modification system termed "synthetic ligation reassembly," or simply "SLR," a "directed evolution process," to generate phytases with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecules having an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved. The mutually compatible ligatable ends of the nucleic acid building blocks to be assembled are considered to be "serviceable" for this type of ordered assembly if they enable the building blocks to be coupled in predetermined orders. Thus the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces. In one aspect, a non-stochastic method termed synthetic ligation reassembly (SLR), that is somewhat related to stochastic shuffling, save that the nucleic acid building blocks are not shuffled or concatenated or chimerized randomly, but rather are assembled non-stochastically can be used to create variants.

The SLR method does not depend on the presence of a high level of homology between polynucleotides to be shuffled. The invention can be used to non-stochastically generate libraries (or sets) of progeny molecules comprised of over $10^{100}$ different chimeras. Conceivably, SLR can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. Enzymes and polypeptides for use in the invention can be mutagenized in accordance with the methods described herein.

Thus according to one aspect of the invention, the sequences of a plurality of progenitor nucleic acid templates are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, or almost all of the progenitor templates. In one aspect, a serviceable demarcation point is an area of homology that is shared by all of the progenitor templates.

In one aspect, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated can comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one aspect, the recombination is facilitated by, or occurs at, areas of homology between the man-made intron-containing gene and a nucleic acid with serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which can have two ligatable ends. The two ligatable ends on each nucleic acid building block may be two blunt ends (i.e. each having an overhang of zero nucleotides), or one blunt end and one overhang, or two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Exemplary sizes for building block range from 1 base pair (not including any overhangs) to 100,000 base pairs (not including any overhangs). Other size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. In one aspect, the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect variants of the polynucleotides and polypeptides described herein are obtained by the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In a another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., SEQ ID NO:1) into a suitable host cell. The regions of partial sequence homology promote processes that result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides methods for generating hybrid polynucleotides which may encode biologically active hybrid polypeptides (e.g., a hybrid phytase). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

In addition to the various methods described above, various methods are known in the art that can be used to obtain hybrid polynucleotides with enhanced enzymatic properties. The following examples illustrate the use of such procedures for obtaining thermostable or thermotolerant enzymes by mutagenesis of a polynucleotide encoding a wild-type enzyme of interest.

For example, M. Lehmann et al. (in *Biochimica et Biophysica Acta* 1543:408–415, 2000) describes a "consensus approach" wherein sequence alignment of homologous fungal phytases was used to calculate a consensus phytase amino acid sequence. Upon construction of the corresponding consensus gen, recombinant expression and purification, the recombinant phytase obtained displayed an unfolding temperature (Tm) 15–22° C. higher than that of all parent phytases used in the design. Site-directed mutagenesis of the gene encoding the recombinant protein was used to further increase the Tm value to 90.4° C. The thermostabilizing effect was attributed to a combination of multiple amino acid exchanges that were distributed over the entire sequence of the protein and mainly affected surface-exposed residues.

Another approach to obtaining an enzyme with enhanced thermal properties is described by L. Jermutus et al. (J. of Biotechnology 85:15–24, 2001). In this approach ionic interactions and hydrogen bonds on the surface of *Aspergillus terreus* phytase were first restored to correspond to those present in the homologous, but more thermostable enzyme from *A. niger*. Then entire secondary structural elements were replaced in the same region and based on the crystal structure of *A. niger* phytase. The replacement of one α-helix on the surface of *A. terreus* phytase by the corresponding stretch of *A niger* phytase resulted in a structure-based chimeric enzyme (fusion protein) with improved thermostability and unaltered enzymatic activity.

Yet another approach is illustrated by L. Giver et al. (*Proc. Natl. Acad. Sci. USA* 95:12809–12813, 1998), wherein six generations of random mutagenesis introduced during mutagenic PCR of a polynucleotide encoding *Bacillus subtilis* p-nitrobenzyl esterase followed by in vitro recombination based on the method of Stemmer resulted in a recombinant esterase with increased thermostability (greater than 14° C. increase in Tm) without compromising catalytic activity at lower temperatures.

C. Vetriani et al. (*Proc. Natl. Acad. Sci USA* 95:12300–12305, 1998) describe a procedure by which homology-based modeling and direct structure comparison of the hexameric glutamate dehydrogenases from the hyperthermophiles *Pyrococcus furiosus* and *Thermococcus litoralis*, with optimal growth temperatures of 100° C. and 88° C., respectively, were used to determine key thermostabilizing features. An intersubunit ion-pair network observed to be substantially reduced in the less stable enzyme was altered by mutagenesis of two residues therein to restore the interactions found in the more stable enzyme. Although either single mutation had adverse effects on the thermostability, with both mutations in place, a four-fold improvement of stability at 104° C. over the wild-type enzyme was observed.

A. Tomschy et al. (*Protein Science* 9:1304–1311, 2000) describe a procedure utilizing the crystal structure of *Aspergillus Niger* phytase (at 2.5 angstroms resolution) to specify all active sites of the enzyme. A multiple amino acid sequence alignment was then used to identify non-conserved active site residues that might correlate with a given favorable property of interest. Using this approach, Gln27 of *A. fumigatus* phytase, which differed from Leu27 of *A. niger*, was identified as likely to be involved in substrate binding and/or release and responsible for the lower specific activity of the *A. fumigatus* phytase (26.5 vs. 196 6 U/mg protein at pH 5.0). Site directed mutagenesis of Gln27 of *A. fumigatus* phytase to Leu increased the specific activity of the mutant enzyme to 92.1 U/mg protein.

In one aspect, the instant invention provides a method (and products thereof) of producing stabilized aqueous liquid formulations having phytase activity that exhibit increased resistance to heat inactivation of the enzyme activity and which retain their phytase activity during prolonged periods of storage. The liquid formulations are stabilized by means of the addition of urea and/or a polyol such as sorbitol and glycerol as stabilizing agent. Also provided are feed preparations for monogastric animals and methods for the production thereof that result from the use of such stabilized aqueous liquid formulations. Additional details regarding this approach are in the public literature and/or are known to the skilled artisan. In a particular non-limiting exemplification, such publicly available literature includes EP 0626010 (WO 9316175 A1) (Barendse et al.), although references in the publicly available literature do not teach the inventive molecules of the instant application.

Enzymes encoded by original polynucleotides include, but are not limited to, hydrolases and phytases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples, such as thermostability or thermotolerance, can be used to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as *Xanthobacter, Eubacteria* and *Archaebacteria,* and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms can be used. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides can be in a vector that includes appropriate control sequences. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name—"secondary metabolites". Secondary metabolites are generally the products of complex biosynthetic pathways and are usually derived from common cellular precursors. Secondary metabolites that influence the growth or survival of other organisms are known as "bioactive" compounds and serve as key components of the chemical-defense arsenal of both micro- and macro-organisms. Humans have exploited these compounds for use as antibiotics, anti-infectives and other bioactive compounds with activity against a broad range of prokaryotic and eukaryotic pathogens. Approximately 6,000 bioactive compounds of microbial origin have been characterized, with more than 60% produced by the gram positive soil bacteria of the genus Streptomyces. (Barnes et al., Proc. Nat. Acad. Sci. U.S.A., 91, 1994).

Hybridization screening using high density filters or biopanning has proven an efficient approach to detect homologues of pathways containing genes of interest to discover novel bioactive molecules that may have no known counterparts. Once a polynucleotide of interest is enriched in a library of clones it may be desirable to screen for an activity. For example, it may be desirable to screen for the expression of small molecule ring structures or "backbones". Because the genes encoding these polycyclic structures can often be expressed in *E. coli*, the small molecule backbone can be manufactured, even if in an inactive form. Bioactivity is conferred upon transferring the molecule or pathway to an appropriate host that expresses the requisite glycosylation and methylation genes that can modify or "decorate" the structure to its active form. Thus, even if inactive ring compounds, recombinantly expressed in *E. coli* are detected to identify clones, which are then shuttled to a metabolically rich host, such as *Streptomyces* (e.g., *Streptomyces diversae* or *venezuelae*) for subsequent production of the bioactive molecule. It should be understood that *E. coli* can produce active small molecules and in certain instances it may be desirable to shuttle clones to a metabolically rich host for "decoration" of the structure, but not required. The use of high throughput robotic systems allows the screening of hundreds of thousands of clones in multiplexed arrays in microtiter dishes.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) Biochem. Biophys. Res. Commun. 229:295–8)), media, culture systems and the like. In one aspect, gene amplification using selection markers, e.g., glutamine synthetase (see, e.g., Sanders (1987) Dev. Biol. Stand. 66:55–63), in cell systems are used to overexpress the polypeptides of the invention.

Various mammalian cell culture systems can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

The enzymes and polynucleotides of the present invention can be provided in an isolated form or purified to homogeneity. The phytase polypeptide of the invention can be obtained using any of several standard methods. For example, phytase polypeptides can be produced in a standard recombinant expression system (as described herein), chemically synthesized (although somewhat limited to small phytase peptide fragments), or purified from organisms in which they are naturally expressed. Useful recombinant expression methods include mammalian hosts, microbial hosts, and plant hosts.

The recombinant expression, or over-expression, of the phytase molecules of the invention may be achieved in combination with one or more additional molecules such as, for example, other enzymes. This approach is useful for producing combination products, such as a plant or plant part that contains the instant phytase molecules as well as one or more additional molecules—the phytase molecules and the additional molecules can be used in a combination treatment. The resulting recombinantly expresssed molecules may be used in homogenized and/or purified form or alternatively in relatively unpurified form (e.g. as consumable plant parts that are useful when admixed with other foodstuffs for catalyzing the degradation of phytate).

The present invention provides a recombinant enzyme expressed in a host. The present invention provides a substantially pure phytase enzyme. Thus, an enzyme of the present invention may be a recombinant enzyme, a natural enzyme, or a synthetic enzyme, or a recombinant enzyme.

In a particular aspect, the present invention provides for the expression of phytase in transgenic plants or plant organs and methods for the production thereof. DNA expression constructs are provided for the transformation of plants with a gene encoding phytase under the control of regulatory sequences which are capable of directing the expression of phytase. These regulatory sequences include sequences capable of directing transcription in plants, either constitutively, or in stage and/or tissue specific manners.

The manner of expression depends, in part, on the use of the plant or parts thereof. The transgenic plants and plant organs provided by the present invention may be applied to a variety of industrial processes either directly, e.g. in animal feeds or alternatively, the expressed phytase may be extracted and if desired, purified before application. Alternatively, the recombinant host plant or plant part may be used directly. In a particular aspect, the present invention provides methods of catalyzing phytate-hydrolyzing reactions using seeds containing enhanced amounts of phytase. The method involves contacting transgenic, non-wild type seeds, e.g., in a ground or chewed form, with phytate-containing substrate and allowing the enzymes in the seeds to increase the rate of reaction. By directly adding the seeds to a phytate-containing substrate, the invention provides a solution to the expensive and problematic process of extracting and purifying the enzyme. In one exemplification the present invention provides methods of treatment whereby an organism lacking a sufficient supply of an enzyme is administered the enzyme in the form of seeds containing enhanced amounts of the enzyme. In one aspect, the timing of the administration of the enzyme to an organism is coordinated with the consumption of a phytate-containing foodstuff.

The expression of phytase in plants can be achieved by a variety of means. Specifically, for example, technologies are available for transforming a large number of plant species, including dicotyledonous species (e.g. tobacco, potato, tomato, Petunia, *Brassica*). Additionally, for example, strategies for the expression of foreign genes in plants are available. Additionally still, regulatory sequences from plant genes have been identified that are serviceable for the construction of chimeric genes that can be functionally expressed in plants and in plant cells (e.g. Klee et al., 1987; Clark et al., 1990; Smith et al., 1990).

The introduction of gene constructs into plants can be achieved using several technologies including transformation with *Agrobacterium tumefaciens* or *Agrobacterium rhizogenes*. Non-limiting examples of plant tissues that can be transformed thusly include protoplasts, microspores or pollen, and explants such as leaves, stems, roots, hypocotyls, and cotyls. Furthermore, DNA can be introduced directly into protoplasts and plant cells or tissues by microinjection, electroporation, particle bombardment, and direct DNA uptake.

Proteins may be produced in plants by a variety of expression systems. For instance, the use of a constitutive promoter such as the 35S promoter of Cauliflower Mosaic Virus (Guilley et al., 1982) is serviceable for the accumulation of the expressed protein in virtually all organs of the transgenic plant. Alternatively, the use of promoters that are highly tissue-specific and/or stage-specific are serviceable for this invention (Higgins, 1984; Shotwell, 1989) in order to bias expression towards desired tissues and/or towards a desired stage of development. Further details relevant to the expression in plants of the phytase molecules of the instant invention are disclosed, for example, in U.S. Pat. No. 5,770,413 (Van Ooijen et al.) and U.S. Pat. No. 5,593,963 (Van Ooijen et al.), although these reference do not teach the inventive molecules of the instant application and instead teach the use of fungal phytases.

In sum, it is relevant to this invention that a variety of means can be used to achieve the recombinant expression of phytase in a transgenic plant or plant part. Such a transgenic plants and plant parts are serviceable as sources of recombinantly expressed phytase, which can be added directly to phytate-containing sources. Alternatively, the recombinant plant-expressed phytase can be extracted away from the plant source and, if desired, purified prior to contacting the phytase substrate.

Within the context of the present invention, plants to be selected include, but are not limited to crops producing edible flowers such as cauliflower (*Brassica oleracea*), artichoke (*Cynara scolymus*), fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata*), tomato (*Lycopersicon*, e.g. *esculentum*), leafs, such as alfalfa (*Medicago*, e.g. *sativa*), cabbages (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*), roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*) and seeds, such as bean (*Phaseolus*, e.g. *vulgaris*), pea (*Pisum*, e.g. *sativum*), soybean (*Glycin*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*), rapeseed (*Brassica napus*), millet (*Panicum* L.), sunflower (*Helianthus annus*), oats (*Avena sativa*), tubers, such as kohlrabi (*Brassica*, e.g. *oleraceae*), potato (*Solanum*, e.g. *tuberosum*) and the like.

It is understood that additional plant as well as non-plant expression systems can be used within the context of this invention. The choice of the plant species is primarily determined by the intended use of the plant or parts thereof and the amenability of the plant species to transformation.

Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment (Potrykus, 1990). In addition to these so-called direct DNA transformation methods, transformation systems involving vectors are widely available, such as viral vectors (e.g. from the Cauliflower Mosaic Cirus (CaMV) and bacterial vectors (e.g. from the genus *Agrobacterium*) (Potrykus, 1990). After selection and/or screening, the protoplasts, cells or plant parts that have been transformed can be regenerated into whole plants, using methods known in the art (Horsch et al., 1985). The choice of the transformation and/or regeneration techniques is not critical for this invention.

For dicots, a binary vector system can be used (Hoekema et al., 1983; EP 0120516 Schilperoort et al.). For example, *Agrobacterium* strains can be used which contain a vir plasmid with the virulence genes and a compatible plasmid containing the gene construct to be transferred. This vector can replicate in both *E. coli* and in *Agrobacterium*, and is derived from the binary vector Bin19 (Bevan, 1984) that is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto et al., 1993). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm et al., 1990). The introduction of genetic material into aleurone protoplasts of other monocot crops such as wheat and barley has been reported (Lee et al., 1989). Wheat plants have been regenerated from embryogenic suspension culture by selecting only the aged compact and nodular embryogenic callus tissues for the establishment of the embryogenic suspension cultures (Vasil et al., 1972: Vasil et al., 1974). The combination with transformation systems for these crops enables the application of the present invention to monocots. These methods may also be applied for the transformation and regeneration of dicots.

Expression of the phytase construct involves such details as transcription of the gene by plant polymerases, translation of mRNA, etc. that are known to persons skilled in the art of recombinant DNA techniques. Only details relevant for the proper understanding of this invention are discussed below. Regulatory sequences which are known or are found to cause expression of phytase may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamine synthase gene (Tingey et al., 1987), those for seed-specific expression, such as the cruciferin A promoter from *Brassica napus* (Ryan et al., 1989), those for tuber-specific expression, such as the class-I patatin promoter from potato (Koster-Topfer et al., 1989; Wenzler et al., 1989) or those for fruit-specific expression, such as the polygalacturonase (PG) promoter from tomato (Bird et al., 1988).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, supra). The regulatory sequences may also include enhancer sequences, such as found in the 35S promoter of CaMV, and mRNA stabilizing sequences such as the leader sequence of Alfalfa Mosaic Cirus (AlMV) RNA4 (Brederode et al., 1980) or any other sequences functioning in a like manner.

The phytase should be expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

To obtain expression in the cytoplasm of the cell, the expressed enzyme should not contain a secretory signal peptide or any other target sequence. For expression in chloroplasts and mitochondria the expressed enzyme should contain specific so-called transit peptide for import into these organelles. Targeting sequences that can be attached to the enzyme of interest in order to achieve this are known (Smeekens et al., 1990; van den Broeck et al., 1985; Wolter et al., 1988). If the activity of the enzyme is desired in the vacuoles a secretory signal peptide has to be present, as well as a specific targeting sequence that directs the enzyme to these vacuoles (Tague et al., 1990). The same is true for the protein bodies in seeds. The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species may be preferred, heterologous signal sequences, i.e. those originating from other plant species or of microbial origin, may be used as well. Such signal sequences are known to those skilled in the art. Appropriate signal sequences which may be used within the context of the present invention are disclosed in Blobel et al., 1979; Von Heijne, 1986; Garcia et al., 1987; Sijmons et al., 1990; Ng et al., 1994; and Powers et al., 1996).

All parts of the relevant DNA constructs (promoters, regulatory-, secretory-, stabilizing-, targeting-, or termination sequences) of the present invention may be modified, if desired, to affect their control characteristics using methods known to those skilled in the art. It is pointed out that plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

In one aspect, the instant invention provides a method (and products thereof) of achieving a highly efficient overexpression system for phytase and other molecules. In one aspect, the invention provides a method (and products thereof) of achieving a highly efficient overexpression system for phytase and pH 2.5 acid phosphatase in *Trichoderma*. This system results in enzyme compositions that have particular utility in the animal feed industry. Additional details regarding this approach are in the public literature and/or are known to the skilled artisan. In a particular non-limiting exemplification, such publicly available literature includes EP 0659215 (WO 9403612 A1) (Nevalainen et al.), although these reference do not teach the inventive molecules of the instant application.

In another aspect, methods can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome or immediately adjacent to one another and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. Once ligated into an appropriate vector, two or more vectors containing different phytase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, In one aspect, the invention relates to a method for producing a biologically active hybrid polypeptide and screening such a polypeptide for enhanced activity by:

(1) introducing at least a first polynucleotide in operable linkage and a second polynucleotide in operable linkage, said at least first polynucleotide and second polynucleotide sharing at least one region of partial sequence homology, into a suitable host cell;

(2) growing the host cell under conditions which promote sequence reorganization resulting in a hybrid polynucleotide in operable linkage;

(3) expressing a hybrid polypeptide encoded by the hybrid polynucleotide;

(4) screening the hybrid polypeptide under conditions which promote identification of enhanced biological activity; and (5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used there may be mentioned viral particles, baculovirus, bacteriophage 1 insertion vectors or replacement vectors, phage, plasmids, phagemids, cosmids, fosmids, bacterial artificial chromosomes (BAC), viral DNA (e.g., vaccinia, adenovirus, foul pox virus, pseudorabies and derivatives of SV40), P1-based artificial chromosomes (PAC), yeast plasmids, yeast artificial chromosomes (YAC), and any other vectors specific for specific hosts of interest (such as *bacillus, Aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript® plasmids, pNH vectors, (lambda-ZAP® vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

An exemplary vector for use in the present invention contains an f-factor origin replication. The f-factor (or fertility factor) in *E. coli* is a plasmid which effects high frequency transfer of itself during conjugation and less frequent transfer of the bacterial chromosome itself. One aspect uses cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

Another type of vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al., 1989).

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers. In addition, the expression vectors can contain one or more selectable marker genes to provide a phenotypic trait for selection of transformed host cells such as dihydrofolate reductase or neomycin resistance for eukaryotic cell culture, or tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, variant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, in one aspect of the invention the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it can still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:

(a) Primers that include a poly-A head and poly-T tail which when made single-stranded provide orientation can be utilized. This is accomplished by having the first few bases of the primers made from RNA and hence easily removed RNAse H.

(b) Primers that include unique restriction cleavage sites can be utilized. Multiple sites, a battery of unique sequences, and repeated synthesis and ligation steps would be required.

(c) The inner few bases of the primer can be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:

1) The use of vectors only stably maintained when the construct is reduced in complexity;

2) The physical recovery of shortened vectors by physical procedures. In this case, the cloning vector is recovered using standard plasmid isolation procedures and size fractionated on either an agarose gel, or column with a low molecular weight cut off utilizing standard procedures;

3) The recovery of vectors containing interrupted genes which can be selected when insert size decreases; and 4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalyzing the hydrolysis of a phytate).

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, prior to or during recombination or reassortment, polynucleotides of the invention or polynucleotides generated by the method described herein can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine, see Sun and Hurley, 1992); an N-acetylated or deacetylated 4'-fluro-4-aminobiphenyl adduct capable of inhibiting DNA synthesis (see, for example, van de Poll et al., 1992); or a N-acetylated or deacetylated 4-aminobiphenyl adduct capable of inhibiting DNA synthesis (see also, van de Poll et al., 1992, pp. 751–758); trivalent chromium, a trivalent chromium salt, a polycyclic aromatic hydrocarbon ("PAH") DNA adduct capable of inhibiting DNA replication, such as 7-bromomethyl-benz[a]anthracene ("BMA"), tris(2,3-dibromopropyl)phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). An exemplary means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect, the invention is directed to a method of producing recombinant proteins having biological activity by treating a sample comprising double-stranded template polynucleotides encoding a wild type protein under conditions according to the invention which provide for the production of hybrid or re-assorted polynucleotides.

The invention also provides for the use of proprietary codon primers (containing a degenerate N,N,G/T sequence) to introduce point mutations into a polynucleotide, so as to generate a set of progeny polypeptides in which a full range of single amino acid substitutions is represented at each amino acid position (gene site saturated mutagenesis (GSSM)). The oligos used are comprised contiguously of a first homologous sequence, a degenerate N,N,G/T sequence, and optionally a second homologous sequence. The downstream progeny translational products from the use of such oligos include all possible amino acid changes at each amino acid site along the polypeptide, because the degeneracy of the N,N,G/T sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N,G/T sequence, to introduce any combination or permutation of amino acid additions, deletions, and/or substitutions.

In one aspect, it is possible to simultaneously mutagenize two or more contiguous amino acid positions using an oligo that contains contiguous N,N,G/T triplets, i.e. a degenerate $(N,N,G/T)_n$ sequence.

In another aspect, the present invention provides for the use of degenerate cassettes having less degeneracy than the N,N,G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, or an N,N,G/C triplet sequence.

It is appreciated, however, that the use of a degenerate triplet (such as N,N,G/T or an N,N,G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N,G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in one aspect, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, polynucleotides (e.g., SEQ ID NO:1) and polypeptides (e.g., SEQ ID NO:2) of the invention can be derived by saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, mutagenesis can be used to replace each of any number of bases in a polynucleotide sequence, wherein the number of bases to be mutagenized can be every integer from 15 to 100,000. Thus, instead of mutagenizing every position along a molecule, one can subject every or a discrete number of bases (can be a subset totaling from 15 to 100,000) to mutagenesis. A separate nucleotide can be used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette can be about 1–500 bases in length) in defined polynucleotide sequence to be mutagenized (wherein the sequence to be mutagenized can be from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In one aspect, a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

One aspect of the invention is an isolated nucleic acid comprising SEQ ID NO:1, sequences substantially identical thereto, sequences complementary thereto, or a fragment comprising at least 10, 15, 20, 25, 30, 35, 40, 50, 75, 100, 150, 200, 300, 400, or 500 consecutive bases of one of the sequences of SEQ ID NO:1. The isolated, nucleic acids may comprise DNA, including cDNA, genomic DNA, and synthetic DNA. The DNA may be double-stranded or single-stranded, and if single stranded may be the coding strand or non-coding (anti-sense) strand. Alternatively, the isolated nucleic acids may comprise RNA.

As discussed in more detail below, the isolated nucleic acid sequences of the invention may be used to prepare the polypeptide of SEQ ID NO:2, and sequences substantially identical thereto, or fragments comprising at least 5, 10, 15, 20, 25, 30, 35, 40, 50, 75, 100, or 150 consecutive amino acids of one of the polypeptides of SEQ ID NO:2, and sequences substantially identical thereto.

Accordingly, another aspect of the invention is an isolated nucleic acid sequence which encodes one of the polypeptides of SEQ ID NO:2, sequences substantially identical thereto, or fragments comprising at least 5, 10, 15, 20, 25, 30, 35, 40, 50, 75, 100, or 150 consecutive amino acids of one of the polypeptides of SEQ ID NO:2. The coding sequences of these nucleic acids may be identical to one of the coding sequences of SEQ ID NO:1, or a fragment thereof, or may be different coding sequences which encode one of the polypeptides of SEQ ID NO:2, and sequences substantially identical thereto, and fragments having at least 5, 10, 15, 20, 25, 30, 35, 40, 50, 75, 100, or 150 consecutive amino acids of one of the polypeptides of SEQ ID NO:2 as a result of the redundancy or degeneracy of the genetic code. The genetic code is well known to those of skill in the art and can be obtained, for example, on page 214 of B. Lewin, *Genes VI*, Oxford University Press, 1997.

The isolated nucleic acid sequence which encodes one of the polypeptides of SEQ ID NO:2, and sequences substantially identical thereto, may include, but is not limited to only a coding sequence of one of SEQ ID NO:1, and sequences substantially identical thereto, and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only coding sequence for the polypeptide as well as a polynucleotide which includes additional coding and/or non-coding sequence.

Alternatively, the nucleic acid sequences of the invention may be mutagenized using conventional techniques, such as site directed mutagenesis, or other techniques familiar to those skilled in the art, to introduce silent changes into the polynucleotide of SEQ ID NO:1, and sequences substantially identical thereto. As used herein, "silent changes" include, for example, changes that do not alter the amino acid sequence encoded by the polynucleotide. Such changes may be desirable in order to increase the level of the polypeptide produced by host cells containing a vector encoding the polypeptide by introducing codons or codon pairs that occur frequently in the host organism.

The invention also relates to polynucleotides that have nucleotide changes which result in amino acid substitutions, additions, deletions, fusions and truncations in the polypeptides of the invention (e.g., SEQ ID NO:2). Such nucleotide changes may be introduced using techniques such as site directed mutagenesis, random chemical mutagenesis, exonuclease III deletion, and other recombinant DNA techniques. Alternatively, such nucleotide changes may be naturally occurring allelic variants which are isolated by identifying nucleic acid sequences which specifically hybridize to probes comprising at least 10, 15, 20, 25, 30, 35, 40, 50, 75, 100, 150, 200, 300, 400, or 500 consecutive bases of one of the sequences of SEQ ID NO:1, and sequences substantially identical thereto, (or the sequences complementary thereto), under conditions of high, moderate, or low stringency as provided herein.

The isolated nucleic acids of SEQ ID NO:1, sequences substantially identical thereto, complementary sequences, or a fragment comprising at least 10, 15, 20, 25, 30, 35, 40, 50, 75, 100, 150, 200, 300, 400, or 500 consecutive bases of one of the foregoing sequences, may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel et al. *Current Protocols in Molecular Biology*, John Wiley 503 Sons, Inc. 1997 and Sambrook et al., *Molecular Cloning: A Laboratory Manual*, 2d Ed., Cold Spring Harbor Laboratory Press, 1989.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). Typically, the probes comprise oligonucleotides. In one aspect, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World," *PCR Methods and Applications* 1:5–16, 1991; E. Fahy et al., "Self-sustained Sequence Replication (3SR): An Isothermal Transcription-based Amplification System Alternative to PCR", *PCR Methods and Applications* 1:25–33, 1991; and Walker G. T. et al., "Strand Displacement Amplification-an Isothermal in vitro DNA Amplification Technique", *Nucleic Acid Research* 20:1691–1696, 1992). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of a sequence as set forth in SEQ ID NO:1, and sequences substantially identical thereto, may also be used in chromosome walking procedures to identify clones containing genomic sequences located adjacent to the nucleic acid sequences as set forth above. Such methods allow the isolation of genes which encode additional proteins from the host organism.

An isolated nucleic acid sequence as set forth in SEQ ID NO:1, sequences substantially identical thereto, sequences complementary thereto, or a fragment comprising at least 10, 15, 20, 25, 30, 35, 40, 50, 75, 100, 150, 200, 300,400, or 500 consecutive bases of one of the foregoing sequences may be used as probes to identify and isolate related nucleic acids. In some aspects, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO$_4$, pH 7.0, 5.0 mM Na$_2$EDTA, 0.5% SDS, 10× Denhardt's, and 0.5 mg/ml polyriboadenylic acid. Approximately 2×10$^7$ cpm (specific activity 4–9×10$^8$ cpm/ug) of $^{32}$P end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas: For probes between 14 and 70 nucleotides in length the melting temperature ($T_m$) is calculated using the formula: $T_m$=81.5+16.6 (log [Na+])+0.41(fraction G+C)−(600/N), where N is the length of the probe. If the hybridization is carried out in a solution containing formamide, the melting temperature may be calculated using the equation: $T_m$=81.5+16.6(log [Na+])+0.41(fraction G+C)−(0.63% formamide)−(600/N), where N is the length of the probe. Prehybridization may be carried out in 6×SSC, 5× Denhardt's reagent, 0.5% SDS, 100 µg denatured fragmented salmon sperm DNA or 6×SSC, 5× Denhardt's reagent, 0.5% SDS, 100 µg denatured fragmented salmon sperm DNA, 50% formamide. The formulas for SSC and Denhardt's solutions can be found, e.g., in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15–25° C. below the Tm. For shorter probes, such as oligonucleotide probes, the hybridization may be conducted at 5–10° C. below the $T_m$. Typically, for hybridizations in 6×SSC, the hybridization is conducted at approximately 68° C. Usually, for hybridizations in 50% formamide containing solutions, the hybridization is conducted at approximately 42° C. All of the foregoing hybridizations are considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below.

Nucleic acids which have hybridized to the probe can be identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1 M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

For example, the preceding methods may be used to isolate nucleic acids having a sequence with at least about 99%, at least 98%, at least 97%, at least 95%, at least 90%, or at least 80% homology to a nucleic acid sequence as set forth in SEQ ID NO:1, sequences substantially identical thereto, or fragments comprising at least about 10, 15, 20, 25, 30, 35, 40, 50, 75, 100, 150, 200, 300, 400, or 500 consecutive bases thereof, and the sequences complementary to any of the foregoing sequences. Homology may be measured using an alignment algorithm. For example, the homologous polynucleotides may have a coding sequence which is a naturally occurring allelic variant of one of the coding sequences described herein. Such allelic variants may have a substitution, deletion or addition of one or more nucleotides when compared to a nucleic acid sequence as set forth in SEQ ID NO:1, or sequences complementary thereto.

Additionally, the above procedures may be used to isolate nucleic acids which encode polypeptides having at least about 99%, at least 95%, at least 90%, at least 85%, at least 80%, or at least 70% homology to a polypeptide having a sequence as set forth in SEQ ID NO:2, sequences substantially identical thereto, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Another aspect of the invention is an isolated or purified polypeptide comprising a sequence as set forth in SEQ ID NO:1, sequences substantially identical thereto, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the α factor promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene.

After the expression libraries have been generated, the additional step of "biopanning" such libraries prior to screening by cell sorting can be included. The "biopanning" procedure refers to a process for identifying clones having a specified biological activity by screening for sequence homology in a library of clones prepared by (i) selectively isolating target DNA, from DNA derived from at least one microorganism, by use of at least one probe DNA comprising at least a portion of a DNA sequence encoding an biological having the specified biological activity; and (ii) optionally transforming a host with isolated target DNA to produce a library of clones which are screened for the specified biological activity.

The probe DNA used for selectively isolating the target DNA of interest from the DNA derived from at least one microorganism can be a full-length coding region sequence or a partial coding region sequence of DNA for an enzyme of known activity. The original DNA library can be probed using mixtures of probes comprising at least a portion of the DNA sequence encoding an enzyme having the specified enzyme activity. These probes or probe libraries can be single-stranded and the microbial DNA which is probed can be converted into single-stranded form. The probes that are suitable are those derived from DNA encoding enzymes having an activity similar or identical to the specified enzyme activity which is to be screened.

The probe DNA can be at least about 10 bases or at least 15 bases. In one aspect, the entire coding region may be employed as a probe. Conditions for the hybridization in which target DNA is selectively isolated by the use of at least one DNA probe will be designed to provide a hybridization stringency of at least about 50% sequence identity, more particularly a stringency providing for a sequence identity of at least about 70%.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Hybridization techniques for probing a microbial DNA library to isolate target DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

The probe DNA can be "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase can be selected from: (1) a glass or polymeric surface; (2) a packed column of polymeric beads; and (3) magnetic or paramagnetic particles.

Further, it is optional but desirable to perform an amplification of the target DNA that has been isolated. In this aspect the target DNA is separated from the probe DNA after isolation. It is then amplified before being used to transform hosts. The double stranded DNA selected to include as at least a portion thereof a predetermined DNA sequence can be rendered single-stranded, subjected to amplification and re-annealed to provide amplified numbers of selected double-stranded DNA. Numerous amplification methodologies are now well known in the art.

The selected DNA is then used for preparing a library for screening by transforming a suitable organism. Hosts, e.g., those specifically identified herein, are transformed by artificial introduction of the vectors containing the target DNA by inoculation under conditions conducive for such transformation. The resultant libraries of transformed clones are then screened for clones which display activity for the enzyme of interest.

Having prepared a multiplicity of clones from DNA selectively isolated from an organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be re-screened utilizing a FACS machine for such enzyme activity or for a more specific activity. Alternatively, encapsulation techniques such as gel microdroplets, may be employed to localize multiple clones in one location to be screened on a FACS machine for positive expressing clones within the group of clones which can then be broken out into individual clones to be screened again on a FACS machine to identify positive individual clones. Thus, for example, if a clone mixture has hydrolase activity, then the individual clones may be recovered and screened utilizing a FACS machine to determine which of such clones has hydrolase activity. As used herein, "small insert library" means a gene library containing clones with random small size nucleic acid inserts of up to approximately 5000 base pairs. As used herein, "large insert library" means a gene library containing clones with random large size nucleic acid inserts of approximately 5000 up to several hundred thousand base pairs or greater.

As described with respect to one of the above aspects, the invention provides a process for enzyme activity screening of clones containing selected DNA derived from a microorganism which process includes: screening a library for specified enzyme activity, said library including a plurality of clones, said clones having been prepared by recovering from genomic DNA of a microorganism selected DNA, which DNA is selected by hybridization to at least one DNA sequence which is all or a portion of a DNA sequence encoding an enzyme having the specified activity; and transforming a host with the selected DNA to produce clones which are screened for the specified enzyme activity.

In one aspect, a DNA library derived from a microorganism is subjected to a selection procedure to select therefrom DNA which hybridizes to one or more probe DNA sequences which is all or a portion of a DNA sequence encoding an enzyme having the specified enzyme activity by: (a) rendering the double-stranded genomic DNA population into a single-stranded DNA population; (b) contacting the single-stranded DNA population of (a) with the DNA probe bound to a ligand under conditions permissive of hybridization so as to produce a double-stranded complex of probe and members of the genomic DNA population which hybridize thereto; (c) contacting the double-stranded complex of (b) with a solid phase specific binding partner for said ligand so as to produce a solid phase complex; (d) separating the solid phase complex from the single-stranded DNA population of (b); (e) releasing from the probe the members of the genomic population which had bound to the solid phase bound probe; (f) forming double-stranded DNA from the members of the genomic population of (e); (g) introducing the double-stranded DNA of (f) into a suitable host to form a library containing a plurality of clones containing the selected DNA; and (h) screening the library for the specified enzyme activity.

In another aspect, the process includes a preselection to recover DNA including signal or secretion sequences. In this manner it is possible to select from the genomic DNA population by hybridization as hereinabove described only DNA which includes a signal or secretion sequence. The following paragraphs describe the protocol for this aspect of the invention, the nature and function of secretion signal sequences in general and a specific exemplary application of such sequences to an assay or selection process.

One aspect of this aspect further comprises, after (a) but before (b) above, the steps of: (ai) contacting the single-stranded DNA population of (a) with a ligand-bound oligonucleotide probe that is complementary to a secretion signal sequence unique to a given class of proteins under conditions permissive of hybridization to form a double-stranded complex; (aii) contacting the double-stranded complex of (ai) with a solid phase specific binding partner for said ligand so as to produce a solid phase complex; (aiii) separating the solid phase complex from the single-stranded DNA population of (a); (aiv) releasing the members of the genomic population which had bound to said solid phase bound probe; and (av) separating the solid phase bound probe from the members of the genomic population which had bound thereto.

The DNA which has been selected and isolated to include a signal sequence is then subjected to the selection procedure hereinabove described to select and isolate therefrom DNA which binds to one or more probe DNA sequences derived from DNA encoding an enzyme(s) having the specified enzyme activity. This and other procedures that can be used to practice the invention are described in, e.g., U.S. Pat. Nos. 6,368,798 and 6,054,267.

In vivo biopanning may be performed utilizing a FACS-based and non-optical (e.g., magnetic) based machines. Complex gene libraries are constructed with vectors which contain elements which stabilize transcribed RNA. For example, the inclusion of sequences which result in secondary structures such as hairpins which are designed to flank the transcribed regions of the RNA would serve to enhance their stability, thus increasing their half life within the cell. The probe molecules used in the biopanning process consist of oligonucleotides labeled with reporter molecules that only fluoresce upon binding of the probe to a target molecule. These probes are introduced into the recombinant cells from the library using one of several transformation methods. The probe molecules bind to the transcribed target mRNA resulting in DNA/RNA heteroduplex molecules. Binding of the probe to a target will yield a fluorescent signal which is detected and sorted by the FACS machine during the screening process.

In some aspects, the nucleic acid encoding one of the polypeptides of SEQ ID NO:2, sequences substantially identical thereto, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid encodes a fusion polypeptide in which one of the polypeptides of SEQ ID NO:2, sequences substantially identical thereto, or fragments comprising at least 5, 10, 15, 20, 25, 30, 35, 40, 50, 75, 100, or 150 consecutive amino acids thereof, is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al. *Current Protocols in Molecular Biology*, John Wiley 503 Sons, Inc. 1997 and Sambrook et al., *Molecular Cloning: A Laboratory Manual*, 2d Ed., Cold Spring Harbor Laboratory Press, 1989. Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook, et al., *Molecular Cloning: A Laboratory Manual*, Second Edition, Cold Spring Harbor, N.Y., (1989).

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS®, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The host cell may be any of the host cells familiar to those skilled in the art, including prokaryotic cells, eukaryotic cells, mammalian cells, insect cells, or plant cells. As representative examples of appropriate hosts, there may be mentioned: bacterial cells, such as *E. coli, Streptomyces, Bacillus subtilis, Salmonella typhimurium* and various species within the genera *Pseudomonas, Streptomyces*, and *Staphylococcus*, fungal cells, such as yeast, insect cells such as *Drosophila* S2 and *Spodoptera* Sf9, animal cells such as CHO, COS or Bowes melanoma, and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., *Basic Methods in Molecular Biology*, (1986)).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, *Cell*, 23:175, 1981), and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue. Additional details relating to the recombinant expression of proteins are available to those skilled in the art. For example, *Protein Expression: A Practical Approach* (Practical Approach Series by S. J. Higgins (Editor), B. D. Hames (Editor) (July 1999) Oxford University Press; ISBN: 0199636249 provides ample guidance to the those skilled in the art for the expression of proteins in a wide variety of organisms.

Alternatively, the polypeptides of SEQ ID NO:2, sequences substantially identical thereto, or fragments comprising at least 5, 10, 15, 20, 25, 30, 35, 40, 50, 75, 100, or 150 consecutive amino acids thereof, can be synthetically produced by conventional peptide synthesizers. In other aspects, fragments or portions of the polypeptides may be employed for producing the corresponding full-length polypeptide by peptide synthesis; therefore, the fragments may be employed as intermediates for producing the full-length polypeptides.

As known by those skilled in the art, the nucleic acid sequences of the invention can be optimized for expression in a variety of organisms. In one aspect, sequences of the invention are optimized for codon usage in an organism of interest, e.g., a fungus such as *S. cerevisiae* or a bacterium such as *E. coli*. Optimization of nucleic acid sequences for the purpose of codon usage is well understood in the art to refer to the selection of a particular codon favored by an organism to encode a particular amino acid. Optimized codon usage tables are known for many organisms. For example, see *Transfer RNA in Protein Synthesis* by Dolph L. Hatfield, Byeong J. Lee, Robert M. Pirtle (Editor) (July 1992) CRC Press; ISBN: 0849356989. Thus, the invention also includes nucleic acids of the invention adapted for codon usage of an organism.

Optimized expression of nucleic acid sequences of the invention also refers to directed or random mutagenesis of a nucleic acid to effect increased expression of the encoded protein. The mutagenesis of the nucleic acids of the invention can directly or indirectly provide for an increased yield of expressed protein. By way of non-limiting example, mutagenesis techniques described herein may be utilized to effect mutation of the 5' untranslated region, 3' untranslated region, or coding region of a nucleic acid, the mutation of which can result in increased stability at the RNA or protein level, thereby resulting in an increased yield of protein.

Cell-free translation systems can also be employed to produce one of the polypeptides of SEQ ID NO:2, sequences substantially identical thereto, or fragments comprising at least 5, 10, 15, 20, 25, 30, 35, 40, 50, 75, 100, or 150 consecutive amino acids thereof, using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The invention also relates to variants of the polypeptides of SEQ ID NO:2, sequences substantially identical thereto, or fragments comprising at least 5, 10, 15, 20, 25, 30, 35, 40, 50, 75, 100, and 150 consecutive amino acids thereof. The term "variant" includes derivatives or analogs of these polypeptides. In particular, the variants may differ in amino acid sequence from the polypeptides of SEQ ID NO:2, and sequences substantially identical thereto, by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described in Leung, D. W., et al., *Technique*, 1:11–15, 1989) and Caldwell, R. C. and Joyce G. F., PCR *Methods Applic.*, 2:28–33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described in Reidhaar-Olson, J. F. and Sauer, R. T., et al., *Science*, 241:53–57, 1988. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in pending U.S. patent application Ser. No. 08/677,112 filed Jul. 9, 1996, entitled, Method of "DNA Shuffling with Polynucleotides Produced by Blocking or Interrupting a Synthesis or Amplification Process".

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described in Stemmer, W. P., *PNAS*, USA, 91:10747–10751, 1994. Briefly, in such procedures a plurality of nucleic acids to be recombined are digested with DNase to generate fragments having an average size of 50–200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10–30 ng/µl in a solution of 0.2 mM of each dNTP, 2.2 mM $MgCl2$, 50 mM KCL, 10 mM Tris HCl, pH 9.0, and 0.1% Triton X-100. 2.5 units of Taq polymerase per 100 µl of reaction mixture is added and PCR is performed using the following regime: 94° C. for 60 seconds, 94° C. for 30 seconds, 50–55° C. for 30 seconds, 72° C. for 30 seconds (30–45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C., *PNAS*, USA, 89:7811–7815, 1992.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S. and Youvan, D. C., *Biotechnol. Res.*, 11:1548–1552, 1993. Random and site-directed mutagenesis are described in Arnold, F. H., *Current Opinion in Biotechnology*, 4:450–455, 1993.

In some aspects, the variants are created using shuffling procedures wherein portions of a plurality of nucleic acids which encode distinct polypeptides are fused together to create chimeric nucleic acid sequences which encode chimeric polypeptides as described in pending U.S. patent application Ser. No. 08/677,112 filed Jul. 9, 1996, entitled, "Method of DNA Shuffling with Polynucleotides Produced by Blocking or interrupting a Synthesis or Amplification Process", and pending U.S. patent application Ser. No. 08/651,568 filed May 22, 1996, entitled, "Combinatorial Enzyme Development."

The variants of the polypeptides of SEQ ID NO:2 may be variants in which one or more of the amino acid residues of the polypeptides of SEQ ID NO:2 are substituted with a conserved or non-conserved amino acid residue (e.g., a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue.

Other variants are those in which one or more of the amino acid residues of the polypeptides of SEQ ID NO:2 includes a substituent group.

Still other variants are those in which the polypeptide is associated with another compound, such as a compound to increase the half-life of the polypeptide (for example, polyethylene glycol).

Additional variants are those in which additional amino acids are fused to the polypeptide, such as a leader sequence, a secretory sequence, a proprotein sequence or a sequence which facilitates purification, enrichment, or stabilization of the polypeptide. In some aspects, the fragments, derivatives and analogs retain the same biological function or activity as the polypeptides of SEQ ID NO:2, and sequences substantially identical thereto. In other aspects, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying phytase-encoding nucleic acids to modify codon usage. In one aspect, the invention provides methods for modifying codons in a nucleic acid encoding a phytase to increase or decrease its expression in a host cell. The invention also provides nucleic acids encoding a phytase modified to increase its expression in a host cell, phytase enzymes so modified, and methods of making the modified phytase enzymes. The method comprises identifying a "non-preferred" or a "less preferred" codon in phytase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an phytase isolated from a bacterial cell are modified such that the nucleic acid is optimally expressed in a bacterial cell different from the bacteria from which the phytase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113–118; Hale (1998) Protein Expr. Purif. 12:185–188; Narum (2001) Infect. Immun. 69:7250–7253. See also Narum (2001) Infect. Immun. 69:7250–7253, describing optimizing codons in mouse systems; Outchkourov (2002) Protein Expr. Purif. 24:18–24, describing optimizing codons in yeast; Feng (2000) Biochemistry 39:15399–15409, describing optimizing codons in *E. coli*; Humphreys (2000) Protein Expr. Purif. 20:252–264, describing optimizing codon usage that affects secretion in *E. coli*.

Transgenic Non-human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study phytase activity, or, as models to screen for modulators of phytase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147–157, describing the production of recombinant proteins in the milk of transgenic dairy animals; Baguisi (1999) Nat. Biotechnol. 17:456–461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express or to be unable to express a phytase.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for phytaseactivity, to screen compounds as potential modulators of activity (e.g., potentiation or inhibition of enzyme activity), for antibodies that bind to a polypeptide of the invention, for nucleic acids that hybridize to a nucleic acid of the invention, and the like.

Immobilized Enzyme Solid Supports

The phytase enzymes, fragments thereof and nucleic acids that encode the enzymes and fragments can be affixed to a solid support. This is often economical and efficient in the use of the phytases in industrial processes. For example, a consortium or cocktail of phytase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode and any combination thereof.

For example, solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextran-agarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof.

Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. another type of solid support useful in the present invention is ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Another example of a solid support is a cell, such as a red blood cell.

Methods of Immobilization

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

Arrays, or "BioChips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a phytase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. "Polypeptide arrays" can also be used to simultaneously quantify a plurality of proteins.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171–R174; Schummer (1997) Biotechniques 23:1087–1092; Kern (1997) Biotechniques 23:120–124; Solinas-Toldo (1997) Genes, Chromosomes & Cancer 20:399–407; Bowtell (1999) Nature Genetics Supp. 21:25–32. See also published U.S. patent applications Nos. 20010018642; 20010019827; 20010016322; 20010014449; 20010014448; 20010012537; 20010008765.

Polypeptides and Peptides

The invention provides isolated or recombinant polypeptides having a sequence identity to an exemplary sequence of the invention, e.g., SEQ ID NO:2. As discussed above, the identity can be over the full length of the polypeptide, or, the identity can be over a region of at least about 50, 77, 100, 150, 200, 250, 300 or more residues (to the full length of the polypeptide). Polypeptides of the invention can also be shorter than the full length of exemplary polypeptides (e.g., SEQ ID NO:2). In alternative embodiment, the invention provides polypeptides (peptides, fragments) ranging in size between about 5 and the full length of a polypeptide, e.g., a phytase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400 or more residues, e.g., contiguous residues of the exemplary phytases of SEQ ID NO:2. Peptides of the invention can be useful as, e.g., labeling probes, antigens, toleragens, motifs, phytase active sites.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3☐13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked, or, a combination thereof.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a phytase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2- for —C(=O)—NH—), aminomethylene (CH2-NH), ethylene, olefin (CH=CH), ether (CH2-O), thioether (CH2-S), tetrazole (CN4-), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3 (2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids omithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1–12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149–2154, 1963) (See also Stewart, J. M. and Young, J. D., Solid Phase Peptide Synthesis, 2nd Ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

Another aspect of the invention is polypeptides or fragments thereof which have at least about 70%, at least about 80%, at least about 85%, at least about 90%, at least about 95%, or more than about 95% homology to one of the polypeptides of SEQ ID NO:2, sequences substantially identical thereto, or a fragment comprising at least 5, 10, 15, 20, 25, 30, 35, 40, 50, 75, 100, or 150 consecutive amino acids thereof. Homology may be determined using any of the programs described above which aligns the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO:2, sequences substantially identical thereto, or a fragment comprising at least about 5, 10, 15, 20, 25, 30, 35, 40, 50, 75, 100, or 150 consecutive amino acids thereof, may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO:2, sequences substantially identical thereto, or a fragment comprising at least about 5, 10, 15, 20, 25, 30, 35, 40, 50, 75, 100, or 150 consecutive amino acids thereof using any of the programs described herein.

Another aspect of the invention is an assay for identifying fragments or variants of SEQ ID NO:2, or sequences substantially identical thereto, which retain the enzymatic function of the polypeptides of SEQ ID NO:2 and sequences substantially identical thereto. For example the fragments or variants of the polypeptides, may be used to catalyze biochemical reactions, which indicate that said fragment or variant retains the enzymatic activity of the polypeptides in SEQ ID NO:2.

The assay for determining if fragments of variants retain the enzymatic activity of the polypeptides of SEQ ID NO:2, and sequences substantially identical thereto, includes the steps of; contacting the polypeptide fragment or variant with a substrate molecule under conditions which allow the polypeptide fragment or variant to function, and detecting either a decrease in the level of substrate or an increase in the level of the specific reaction product of the reaction between the polypeptide and substrate.

The polypeptides of SEQ ID NO:2, sequences substantially identical thereto, or fragments comprising at least 5, 10, 15, 20, 25, 30, 35, 40, 50, 75, 100, or 150 consecutive amino acids thereof, may be used in a variety of applications. For example, the polypeptides or fragments thereof may be used to catalyze biochemical reactions. In accordance with one aspect of the invention, there is provided a process for utilizing a polypeptide having SEQ ID NO:2, and sequences substantially identical thereto, or polynucleotides encoding such polypeptides for hydrolyzing haloalkanes. In such procedures, a substance containing a haloalkane compound is contacted with one of the polypeptides of SEQ ID NO:2, sequences substantially identical thereto, under conditions which facilitate the hydrolysis of the compound.

Antibodies and Antibody-based Screening Methods

The invention provides isolated or recombinant antibodies that specifically bind to a phytase of the invention. These antibodies can be used to isolate, identify or quantify the phytases of the invention or related polypeptides. These antibodies can be used to inhibit the activity of an enzyme of the invention. These antibodies can be used to isolated polypeptides related to those of the invention, e.g., related phytase enzymes.

The antibodies can be used in immunoprecipitation, staining (e.g., FACS), immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62–70; Katz (1997) Annu. Rev. Biophys. Biomol. Struct. 26:27–45.

The polypeptides can be used to generate antibodies which bind specifically to the polypeptides of the invention.

The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77–96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, polypeptides (e.g., phytases) and/or antibodies of the invention. The kits also can contain instructional material teaching the methodologies and industrial uses of the invention, as described herein.

The polypeptides of SEQ ID NO:2, sequences substantially identical thereto, or fragments comprising at least 5, 10, 15, 20, 25, 30, 35, 40, 50, 75, 100, or 150 consecutive amino acids thereof, may also be used to generate antibodies which bind specifically to the enzyme polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of a polypeptide of SEQ ID NO:2, sequences substantially identical thereto, or fragments of the foregoing sequences.

In immunoaffinity procedures, the antibody is attached to a solid support, such as a bead or other column matrix. The protein preparation is placed in contact with the antibody under conditions in which the antibody specifically binds to one of the polypeptides of SEQ ID NO:2, sequences substantially identical thereto, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of SEQ ID NO:2, and sequences substantially identical thereto, or fragments comprising at least 5, 10, 15, 20, 25, 30, 35, 40, 50, 75, 100, or 150 consecutive amino acids thereof, can be obtained by direct injection of the polypeptides into an animal or by administering the polypeptides to an animal, for example, a non-human. The antibody so obtained then binds the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunol. Today* 4:72, 1983), and the EBV-hybridoma technique (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to the polypeptides of, for example, SEQ ID NO:2, and fragments thereof. Alternatively, transgenic mice may be used to express humanized antibodies to these polypeptides or fragments.

Antibodies generated against a polypeptide of SEQ ID NO:2, sequences substantially identical thereto, or fragments comprising at least 5, 10, 15, 20, 25, 30, 35, 40, 50, 75, 100, or 150 consecutive amino acids thereof, may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87–116.

As used herein the term "nucleic acid sequence as set forth in SEQ ID NO:1" encompasses a nucleic acid sequence as set forth in SEQ ID NO:1, a sequence substantially identical thereto, fragments of any one or more of the foregoing sequences, nucleotide sequences homologous to SEQ ID NO:1, or homologous to fragments of SEQ ID NO:1, and sequences complementary to all of the preceding sequences. The fragments include portions of SEQ ID NO:1 comprising at least 10, 15, 20, 25, 30, 35, 40, 50, 75, 100, 150, 200, 300, 400, or 500 consecutive nucleotides of SEQ ID NO:1, and sequences substantially identical thereto. Homologous sequences and fragments of SEQ ID NO:1, and sequences substantially identical thereto, refer to a sequence having at least 99%, 98%, 97%, 96%, 95%, 90%, 85%, 80%, 75% or 70% homology to these sequences. Homology may be determined using any of the computer programs and parameters described herein, including FASTA version 3.0t78 with the default parameters. Homologous sequences also include RNA sequences in which uridines replace the thymines in the nucleic acid sequences as set forth in SEQ ID NO:1. The homologous sequences may be obtained using any of the procedures described herein or may result from the correction of a sequencing error. It will be appreciated that the nucleic acid sequences of the invention can be represented in the traditional single character format (See the inside back cover of Stryer, Lubert. *Biochemistry*, $3^{rd}$ edition. W.H Freeman and Co., New York.) or in any other format which records the identity of the nucleotides in a sequence.

As used herein the term "a polypeptide sequence as set forth in SEQ ID NO:2" encompasses s polypeptide sequence as set forth in SEQ ID NO:2, sequences substantially identical thereto, which are encoded by a sequence as set forth in SEQ ID NO:1, polypeptide sequences homologous to the polypeptides of SEQ ID NO:2, and sequences substantially identical thereto, or fragments of any of the preceding sequences. Homologous polypeptide sequences refer to a polypeptide sequence having at least 99%, 98%, 97%, 96%, 95%, 90%, 85%, 80%, 75% or 70% homology to one of the polypeptide sequences of the invention. Homology may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least 5, 10, 15, 20, 25, 30, 35, 40, 50, 75, 100, or 150 consecutive amino acids of the polypeptides of SEQ ID NO:2, and sequences substantially identical thereto. It will be appreciated that the polypeptides of the invention can be represented in the traditional single character format or three letter format (See the inside back cover of Starrier, Lubert. *Biochemistry*, $3^{rd}$ edition. W.H Freeman and Co., New York.) or in any other format which relates the identity of the polypeptides in a sequence.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

The isolated polynucleotide sequences, polypeptide sequence, variants and mutants thereof can be measured for retention of biological activity characteristic to the enzyme of the present invention, for example, in an assay for detecting enzymatic phytase activity (Food Chemicals Codex, $4^{th}$ Ed.). Such enzymes include truncated forms of phytase, and variants such as deletion and insertion variants of the polypeptide sequence as set forth in SEQ ID NO:2. These phytases have thermotolerance. That is, the phytase has a residual specific activity of about 90% after treatment at 70° C. for 30 minutes and about 50% after treatment at 75° C. for 30 minutes. The thermotolerance of the invention phytases is advantageous in using the enzyme as a feed additive as the feed can be molded, granulated, or pelletized at a high temperature.

For example, in one aspect, the invention provides an edible pelletized enzyme delivery matrix and method of use for delivery of phytase to an animal, for example as a nutritional supplement. The enzyme delivery matrix readily releases a phytase enzyme, such as one having the amino acid sequence of SEQ ID NO:2 or at least 30 contiguous amino acids thereof, in aqueous media, such as, for example, the digestive fluid of an animal. The invention enzyme delivery matrix is prepared from a granulate edible carrier selected from such components as grain germ that is spent of oil, hay, alfalfa, timothy, soy hull, sunflower seed meal, wheat meal, and the like, that readily disperse the recombinant enzyme contained therein into aqueous media. In use, the edible pelletized enzyme delivery matrix is administered to an animal to delivery of phytase to the animal. Suitable grain-based substrates may comprise or be derived from any suitable edible grain, such as wheat, corn, soy, sorghum, alfalfa, barley, and the like. An exemplary grain-based substrate is a corn-based substrate. The substrate may be derived from any suitable part of the grain, e.g., a grain germ, approved for animal feed use, such as corn germ that is obtained in a wet or dry milling process. The grain germ can comprise spent germ, which is grain germ from which oil has been expelled, such as by pressing or hexane or other solvent extraction. Alternatively, the grain germ is expeller extracted, that is, the oil has been removed by pressing.

The enzyme delivery matrix of the invention is in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in animal feed. Since the matrix is itself approved for use in animal feed, it can be used as a diluent for delivery of enzymes in animal feed.

The enzyme delivery matrix can be in the form of granules having a granule size ranging from about 4 to about 400 mesh (USS); or about 8 to about 80 mesh; or about 14 to about 20 mesh. If the grain germ is spent via solvent extraction, use of a lubricity agent such as corn oil may be necessary in the pelletizer, but such a lubricity agent ordinarily is not necessary if the germ is expeller extracted. In other aspects of the invention, the matrix is prepared by other compacting or compressing processes such as, for example, by extrusion of the grain-based substrate through a die and grinding of the extrudate to a suitable granule size.

The enzyme delivery matrix may further include a polysaccharide component as a cohesiveness agent to enhance the cohesiveness of the matrix granules. The cohesiveness agent is believed to provide additional hydroxyl groups, which enhance the bonding between grain proteins within the matrix granule. It is further believed that the additional hydroxyl groups so function by enhancing the hydrogen bonding of proteins to starch and to other proteins. The cohesiveness agent may be present in any amount suitable to enhance the cohesiveness of the granules of the enzyme delivery matrix. Suitable cohesiveness agents include one or more of dextrins, maltodextrins, starches, such as corn starch, flours, cellulosics, hemicellulosics, and the like. For example, the percentage of grain germ and cohesiveness agent in the matrix (not including the enzyme) is 78% corn germ meal and 20% by weight of corn starch.

Because the enzyme-releasing matrix of the invention is made from biodegradable materials, the matrix may be subject to spoilage, such as by molding. To prevent or inhibit such molding, the matrix may include a mold inhibitor, such as a propionate salt, which may be present in any amount sufficient to inhibit the molding of the enzyme-releasing matrix, thus providing a delivery matrix in a stable formulation that does not require refrigeration.

The phytase enzyme contained in the invention enzyme delivery matrix and methods is in one aspect a thermotolerant phytase, as described herein, so as to resist inactivation of the phytase during manufacture where elevated temperatures and/or steam may be employed to prepare the pelletized enzyme delivery matrix. During digestion of feed containing the invention enzyme delivery matrix, aqueous digestive fluids will cause release of the active enzyme. Other types of thermotolerant enzymes and nutritional supplements that are thermotolerant can also be incorporated in the delivery matrix for release under any type of aqueous conditions.

A coating can be applied to the invention enzyme matrix particles for many different purposes, such as to add a flavor or nutrition supplement to animal feed, to delay release of animal feed supplements and enzymes in gastric conditions, and the like. Or, the coating may be applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise a phytase enzyme encoded by SEQ ID NO:2 or at least 30 consecutive amino acids thereof. The process can include compacting or compressing the particles of enzyme-releasing matrix into granules, which can be accomplished by pelletizing. The mold inhibitor and cohesiveness agent, when used, can be added at any suitable time, and can be mixed with the grain-based substrate in the desired proportions prior to pelletizing of the grain-based substrate. Moisture content in the pellet mill feed can be in the ranges set forth above with respect to the moisture content in the finished product, and preferably is about 14–15%. Moisture can be added to the feedstock in the form of an aqueous preparation of the enzyme to bring the feedstock to this moisture content. The temperature in the pellet mill can be brought to about 82° C. with steam. The pellet mill may be operated under any conditions that impart sufficient work to the feedstock to provide pellets. The pelleting process itself is a cost-effective process for removing water from the enzyme-containing composition.

In one aspect, the pellet mill is operated with a ⅛ in. by 2 in. die at 100 lb./min. pressure at 82° C. to provide pellets, which then are crumbled in a pellet mill crumbler to provide discrete plural particles having a particle size capable of passing through an 8 mesh screen but being retained on a 20 mesh screen.

The thermotolerant phytases described herein can have high optimum temperatures and can have high heat resistance or heat tolerance. Thus, the phytases of the invention can carry out enzymatic reactions at temperatures normally considered above optimum. The phytases of the invention also can carry out enzymatic reactions after being exposed to high temperatures (thermotolerance being the ability to retain enzymatic activity at temperatures where the wild type phytase is active after previously being exposed to high temperatures, even if the high temperature can inactivate or diminish the enzyme's activity, see also definition of thermotolerance, above). The gene encoding the phytase according to the present invention (e.g., as set forth in SEQ ID NO:1) can be used in preparation of phytases (e.g. using GSSM as described herein) having characteristics different from those of the phytase of SEQ ID NO:2 (in terms of optimum pH, optimum temperature, heat resistance, stability to solvents, specific activity, affinity to substrate, secretion ability, translation rate, transcription control and the like). Furthermore, the polynucleotide of SEQ ID NO:1 may be employed for screening of variant phytases prepared by the methods described herein to determine those having a desired activity, such as improved or modified thermostability or thermotolerance. For example, U.S. Pat. No. 5,830,732, describes a screening assay for determining thermotolerance of a phytase.

An in vitro example of such a screening assay is the following assay for the detection of phytase activity: Phytase activity can be measured by incubating 150 µl of the enzyme preparation with 600 µl of 2 mM sodium phytate in 100 mM Tris HCl buffer, pH 7.5, supplemented with 1 mM $CaCl_2$ for 30 minutes at 37° C. After incubation the reaction is stopped by adding 750 µof 5% trichloroacetic acid. Phosphate released was measured against phosphate standard spectrophotometrically at 700 nm after adding 1500 µl of the color reagent (4 volumes of 1.5% ammonium molybdate in 5.5% sulfuric acid and 1 volume of 2.7% ferrous sulfate; Shimizu, 1992). One unit of enzyme activity is defined as the amount of enzyme required to liberate one pmol Pi per min under assay conditions. Specific activity can be expressed in units of enzyme activity per mg of protein. The enzyme of the present invention has enzymatic activity with respect to the hydrolysis of phytate to inositol and free phosphate.

In one aspect, the instant invention provides a method of hydrolyzing phytate comprised of contacting the phytate with one or more of the novel phytase molecules disclosed herein (e.g., SEQ ID NO:2). Accordingly, the invention provides a method for catalyzing the hydrolysis of phytate to inositol and free phosphate with release of minerals from the phytic acid complex. The method includes contacting a phytate substrate with a degrading effective amount of an enzyme of the invention, such as the enzyme shown in SEQ ID NO:2. The term "degrading effective" amount refers to the amount of enzyme which is required to degrade at least 50% of the phytate, as compared to phytate not contacted with the enzyme. 80% of the phytate can be degraded.

In another aspect, the invention provides a method for hydrolyzing phospho-mono-ester bonds in phytate. The method includes administering an effective amount of phytase molecules of the invention (e.g., SEQ ID NO:2), to yield inositol and free phosphate. An "effective" amount refers to the amount of enzyme which is required to hydrolyze at least 50% of the phospho-mono-ester bonds, as compared to phytate not contacted with the enzyme. In one aspect, at least 80% of the bonds are hydrolyzed.

In a particular aspect, when desired, the phytase molecules may be used in combination with other reagents, such as other catalysts; in order to effect chemical changes (e.g. hydrolysis) in the phytate molecules and/or in other molecules of the substrate source(s). According to this aspect, the phytase molecules and the additional reagent(s) will not inhibit each other. The phytase molecules and the additional reagent(s) can have an overall additive effect, or, alternatively, phytase molecules and the additional reagent(s) can have an overall synergistic effect.

Relevant sources of the substrate phytate molecules include foodstuffs, potential foodstuffs, byproducts of foodstuffs (both in vitro byproducts and in vivo byproducts, e.g. ex vivo reaction products and animal excremental products), precursors of foodstuffs, and any other material source of phytate.

In a non-limiting aspect, the recombinant phytase can be consumed by organisms and retains activity upon consumption. In another exemplification, transgenic approaches can be used to achieve expression of the recombinant phytase— e.g., in a controlled fashion (methods are available for controlling expression of transgenic molecules in time-specific and tissue specific manners).

In one aspect, the phytase activity in the source material (e.g. a transgenic plant source or a recombinant prokaryotic host) may be increased upon consumption; this increase in activity may occur, for example, upon conversion of a precursor phytase molecule in pro-form to a significantly more active enzyme in a more mature form, where said conversion may result, for example, from the ingestion and digestion of the phytase source. Hydrolysis of the phytate substrate may occur at any time upon the contacting of the phytase with the phytate; for example, this may occur before ingestion or after ingestion or both before and after ingestion of either the substrate or the enzyme or both. It is additionally appreciated that the phytate substrate may be contacted with—in addition to the phytase—one or more additional reagents, such as another enzyme, which may be also be applied either directly or after purification from its source material.

It is appreciated that the phytase source material(s) can be contacted directly with the phytate source material(s); e.g. upon in vitro or in vivo grinding or chewing of either or both the phytase source(s) and the phytate source(s). Alternatively the phytase enzyme may be purified away from source material(s), or the phytate substrate may be purified away from source material(s), or both the phytase enzyme and the phytate substrate may be purified away from source material(s) prior to the contacting of the phytase enzyme with the phytate substrate. It is appreciated that a combination of purified and unpurified reagents—including enzyme(s) or substrates(s) or both—may be used.

It is appreciated that more than one source material may be used as a source of phytase activity. This is serviceable as one way to achieve a timed release of reagent(s) from source material(s), where release from different reagents from their source materials occur differentially, for example as ingested source materials are digested in vivo or as source materials are processed in in vitro applications. The use of more than one source material of phytase activity is also serviceable to obtain phytase activities under a range of conditions and fluctuations thereof, that may be encountered—such as a range of pH values, temperatures, salinities, and time intervals—for example during different processing steps of an application. The use of different source materials is also serviceable in order to obtain different reagents, as exemplified by one or more forms or isomers of phytase and/or phytate and/or other materials.

It is appreciated that a single source material, such a transgenic plant species (or plant parts thereof), may be a source material of both phytase and phytate; and that enzymes and substrates may be differentially compartmentalized within said single source—e.g. secreted vs. non-secreted, differentially expressed and/or having differential abundances in different plant parts or organs or tissues or in subcellular compartments within the same plant part or organ or tissue. Purification of the phytase molecules contained therein may comprise isolating and/or further processing of one or more desirable plant parts or organs or tissues or subcellular compartments.

In a particular aspect, this invention provides a method of catalyzing in vivo and/or in vitro reactions using seeds containing enhanced amounts of enzymes. The method comprises adding transgenic, non-wild type seeds, e.g., in a ground form, to a reaction mixture and allowing the enzymes in the seeds to increase the rate of reaction. By directly adding the seeds to the reaction mixture the method provides a solution to the more expensive and cumbersome process of extracting and purifying the enzyme. Methods of treatment are also provided whereby an organism lacking a sufficient supply of an enzyme is administered the enzyme in the form of seeds from one or more plant species, e.g., transgenic plant species, containing enhanced amounts of the enzyme. Additional details regarding this approach are in the public literature and/or are known to the skilled artisan. In a particular non-limiting exemplification, such publicly available literature includes U.S. Pat. No. 5,543,576 (Van Ooijen et al.) and U.S. Pat. No. 5,714,474 (Van Ooijen et al.), although these reference do not teach the inventive molecules of the instant application and instead teach the use of fungal phytases.

In a particular non-limiting aspect, the instant phytase molecules are serviceable for generating recombinant digestive system life forms (or microbes or flora) and for the administration of said recombinant digestive system life forms to animals. Administration may be optionally performed alone or in combination with other enzymes and/or with other life forms that can provide enzymatic activity in a digestive system, where said other enzymes and said life forms may be may recombinant or otherwise. For example, administration may be performed in combination with xylanolytic bacteria.

In a non-limiting aspect, the present invention provides a method for steeping corn or sorghum kernels in warm water containing sulfur dioxide in the presence of an enzyme preparation comprising one or more phytin-degrading enzymes, e.g., in such an amount that the phytin present in the corn or sorghum is substantially degraded. The enzyme preparation may comprise phytase and/or acid phosphatase and optionally other plant material degrading enzymes. The steeping time may be 12 to 18 hours. The steeping may be interrupted by an intermediate milling step, reducing the steeping time. In one aspect, corn or sorghum kernels are steeped in warm water containing sulfur dioxide in the presence of an enzyme preparation including one or more phytin-degrading enzymes, such as phytase and acid phosphatases, to eliminate or greatly reduce phytic acid and the salts of phytic acid. Additional details regarding this approach are in the public literature and/or are known to the skilled artisan. In one exemplification, such publicly available literature includes U.S. Pat. No. 4,914,029 (Caransa et al.) and EP 0321004 (Vaara et al.), although these reference do not teach the inventive molecules of the instant application.

In a non-limiting aspect, the present invention provides a method to obtain a bread dough having desirable physical properties such as non-tackiness and elasticity and a bread product of superior quality such as a specific volume comprising adding phytase molecules to the bread dough. In one aspect, phytase molecules of the instant invention are added to a working bread dough preparation that is subsequently formed and baked. Additional details regarding this approach are in the public literature and/or are known to the skilled artisan. In one exemplification, such publicly available literature includes JP 03076529 (Hara et al.), although this reference does not teach the inventive phytase molecules of the instant application.

In a non-limiting aspect, the present invention provides a method to produce improved soybean foodstuffs. Soybeans are combined with phytase molecules of the instant invention to remove phytic acid from the soybeans, thus producing soybean foodstuffs that are improved in their supply of trace nutrients essential for consuming organisms and in its digestibility of proteins. In one aspect, in the production of soybean milk, phytase molecules of the instant invention are added to or brought into contact with soybeans in order to reduce the phytic acid content. In a non-limiting exemplification, the application process can be accelerated by agitating the soybean milk together with the enzyme under heating or by a conducting a mixing-type reaction in an agitation container using an immobilized enzyme. Additional details regarding this approach are in the public literature and/or are known to the skilled artisan. In a particular non-limiting exemplification, such publicly available literature includes JP 59166049 (Kamikubo et al.), although this reference does not teach the inventive molecules of the instant application.

In one aspect, the instant invention provides a method of producing an admixture product for drinking water or animal feed in fluid form, and which comprises using mineral mixtures and vitamin mixtures, and also novel phytase molecules of the instant invention. In a one aspect, there is achieved a correctly dosed and composed mixture of necessary nutrients for the consuming organism without any risk of precipitation and destruction of important minerals/vitamins, while at the same time optimum utilization is made of the phytin-bound phosphate in the feed. Additional details regarding this approach are in the public literature and/or are known to the skilled artisan. In one exemplification, such publicly available literature includes EP 0772978 (Bendixen et al.), although this reference does not teach the inventive molecules of the instant application.

It is appreciated that the phytase molecules of the instant invention may also be used to produce other alcoholic and non-alcoholic drinkable foodstuffs (or drinks) based on the use of molds and/or on grains and/or on other plants. These drinkable foodstuffs include liquors, wines, mixed alcoholic drinks (e.g. wine coolers, other alcoholic coffees such as Irish coffees, etc.), beers, near-beers, juices, extracts, homogenates, and purees. In one aspect, the instantly disclosed phytase molecules are used to generate transgenic versions of molds and/or grains and/or other plants serviceable for the production of such drinkable foodstuffs. In another aspect, the instantly disclosed phytase molecules are used as additional ingredients in the manufacturing process and/or in the final content of such drinkable foodstuffs. Additional details regarding this approach are in the public literature and/or are known to the skilled artisan. However—due to the novelty of the instant invention—references in the publicly available literature do not teach the inventive molecules instantly disclosed.

In another non-limiting exemplification, the present invention provides a means to obtain refined sake having a reduced amount of phytin and an increased content of inositol. Such a sake may have—through direct and/or psychogenic effects—a preventive action on hepatic disease, arteriosclerosis, and other diseases. In one aspect, a sake is produced from rice Koji by multiplying a rice Koji mold having high phytase activity as a raw material. It is appreciated that the phytase molecules of the instant invention may be used to produce a serviceable mold with enhanced activity (e.g., a transgenic mold) and/or added exogenously to augment the effects of a Koji mold. The strain is added to boiled rice and Koji is produced by a conventional procedure. In one exemplification, the prepared Koji is used, the whole rice is prepared at two stages and Sake is produced at constant Sake temperature of 15° C. to give the objective refined Sake having a reduced amount of phytin and an increased amount of inositol. Additional details regarding this approach are in the public literature and/or are known to the skilled artisan. In one exemplification, such publicly available literature includes JP 06153896 (Soga et al.) and JP 06070749 (Soga et al.), although these references do not teach the inventive molecules of the instant application.

In a non-limiting aspect, the present invention provides a method to obtain an absorbefacient capable of promoting the absorption of minerals including ingested calcium without being digested by gastric juices or intestinal juices at a low cost. In one aspect, the mineral absorbefacient contains a partial hydrolysate of phytic acid as an active ingredient. A partial hydrolysate of the phytic acid can be produced by hydrolyzing the phytic acid or its salts using novel phytase molecules of the instant invention. The treatment with the phytase molecules may occur either alone and/or in a combination treatment (to inhibit or to augment the final effect), and is followed by inhibiting the hydrolysis within a range so as not to liberate all the phosphate radicals. Additional details regarding this approach are in the public literature and/or are known to the skilled artisan. In a particular non-limiting exemplification, such publicly available literature includes JP 04270296 (Hoshino), although reference in the publicly available literature do not teach the inventive molecules of the instant application.

In a non-limiting aspect, the present invention provides a method (and products therefrom) to produce an enzyme composition having an additive or preferably a synergistic phytate hydrolyzing activity; said composition comprises novel phytase molecules of the instant invention and one or more additional reagents to achieve a composition that is serviceable for a combination treatment. In one aspect, the combination treatment of the present invention is achieved with the use of at least two phytases of different position specificity, i.e. any combinations of 1-, 2-, 3-, 4-, 5-, and 6-phytases. By combining phytases of different position specificity an additive or synergistic effect is obtained. Compositions such as food and feed or food and feed additives comprising such phytases in combination are also included in this invention as are processes for their preparation. Additional details regarding this approach are in the public literature and/or are known to the skilled artisan. In one exemplification, such publicly available literature includes WO 9830681 (Ohmann et al.), although references in the publicly available literature do not teach the use of the inventive molecules of the instant application.

In another aspect, the combination treatment of the present invention is achieved with the use of an acid phosphatase having phytate hydrolyzing activity at a pH of 2.5, in a low ratio corresponding to a pH 2.5:5.0 activity profile of from about 0.1:1.0 to 10:1, preferably of from about 0.5:1.0 to 5:1, or from about 0.8:1.0 to 3:1, or from about 0.8:1.0 to 2:1. The enzyme composition preferably displays a higher synergetic phytate hydrolyzing efficiency through thermal treatment. The enzyme composition is serviceable in the treatment of foodstuffs (drinkable and solid food, feed and fodder products) to improve phytate hydrolysis. Additional details regarding this approach are in the public literature and/or are known to the skilled artisan. In a particular non-limiting exemplification, such publicly available literature includes U.S. Pat. No. 5,554,399 (Vanderbeke et al.) and U.S. Pat. No. 5,443,979 (Vanderbeke et al.) which rather teach the use of fungal (in particular *Aspergillus*) phytases.

In a non-limiting aspect, the present invention provides a method (and products therefrom) to produce a composition comprised of the instant novel phytate-acting enzyme in combination with one or more additional enzymes that act on polysaccharides. Such polysaccharides can be selected from the group consisting of arabinans, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

In a particular aspect, the present invention provides a method (and products therefrom) to produce a composition having a synergistic phytate hydrolyzing activity comprising one or more novel phytase molecules of the instant invention, a cellulase (can also include a xylanase), optionally a protease, and optionally one or more additional reagents. In alternative aspects, such combination treatments are serviceable in the treatment of foodstuffs, wood products, such as paper products, and as cleansing solutions and solids.

In one non-limiting exemplification, the instant phytase molecules are serviceable in combination with cellulose components. It is known that cellulases of many cellulolytic bacteria are organized into discrete multi-enzyme complexes, called cellulosomes. The multiple subunits of cellulosomes are composed of numerous functional domains, which interact with each other and with the cellulosic substrate. One of these subunits comprises a distinctive new class of non-catalytic scaffolding polypeptide, which selectively integrates the various cellulase and xylanase subunits into the cohesive complex. Intelligent application of cellulosome hybrids and chimeric constructs of cellulosomal domains should enable better use of cellulosic biomass and may offer a wide range of novel applications in research, medicine and industry.

In another non-limiting exemplification, the instant phytase molecules are serviceable—either alone or in combination treatments—in areas of biopulping and biobleaching where a reduction in the use of environmentally harmful chemicals traditionally used in the pulp and paper industry is desired. Waste water treatment represents another vast application area where biological enzymes have been shown to be effective not only in color removal but also in the bioconversion of potentially noxious substances into useful bioproducts.

In another non-limiting exemplification, the instant phytase molecules are serviceable for generating life forms that can provide at least one enzymatic activity—either alone or in combination treatments—in the treatment of digestive systems of organisms. Particularly relevant organisms to be treated include non-ruminant organisms, although ruminant organisms may also benefit from such treatment. Specifically, it is appreciated that this approach may be performed alone or in combination with other biological molecules (for example, xylanases) to generate a recombinant host that expresses a plurality of biological molecules. It is also appreciated that the administration of the instant phytase molecules and/or recombinant hosts expressing the instant phytase molecules may be performed either alone or in combination with other biological molecules, and/or life forms that can provide enzymatic activities in a digestive system—where said other enzymes and said life forms may be may recombinant or otherwise. For example, administration may be performed in combination with xylanolytic bacteria For example, in addition to phytate, many organisms are also unable to adequately digest hemicelluloses. Hemicelluloses or xylans are major components (35%) of plant materials. For ruminant animals, about 50% of the dietary xylans are degraded, but only small amounts of xylans are degraded in the lower gut of non-ruminant animals and humans. In the rumen, the major xylanolytic species are *Butyrivibrio fibrisolvens* and *Bacteroides ruminicola*. In the human colon, *Bacteroides ovatus* and *Bacteroides fragilis* subspecies "a" are major xylanolytic bacteria. Xylans are chemically complex, and their degradation requires multiple enzymes. Expression of these enzymes by gut bacteria varies greatly among species. *Butyrivibrio fibrisolvens* makes extracellular xylanases but *Bacteroides* species have cell-bound xylanase activity. Biochemical characterization of xylanolytic enzymes from gut bacteria has not been done completely. A xylosidase gene has been cloned from *B. fibrosolvens* 113. The data from DNA hybridizations using a xylanase gene cloned from *B. fibrisolvens* 49 indicate this gene may be present in other *B. fibrisolvens* strains. A cloned xylanase from *Bact. ruminicola* was transferred to and highly expressed in *Bact. fragilis* and *Bact. uniformis*. Arabinosidase and xylosidase genes from *Bact. ovatus* have been cloned and both activities appear to be catalyzed by a single, bifunctional, novel enzyme.

Accordingly, it is appreciated that the present phytase molecules are serviceable for 1) transferring into a suitable host (such as *Bact. fragilis* or *Bact. uniformis*); 2) achieving adequate expression in a resultant recombinant host; and 3) administering said recombinant host to organisms to improve the ability of the treated organisms to degrade phytate. Continued research in genetic and biochemical areas will provide knowledge and insights for manipulation of digestion at the gut level and improved understanding of colonic fiber digestion.

Additional details regarding this approach are in the public literature and/or are known to the skilled artisan. In a particular non-limiting exemplification, such publicly available literature includes U.S. Pat. No. 5,624,678 (Bedford et al.), U.S. Pat. No. 5,683,911 (Bodie et al.), U.S. Pat. No. 5,720,971 (Beauchemin et al.), U.S. Pat. No. 5,759,840 (Sung et al.), U.S. Pat. No. 5,770,012 (Cooper), U.S. Pat. No. 5,786,316 (Baeck et al.), U.S. Pat. No. 5,817,500

(Hansen et al), and journal articles (Jeffries, 1996; Prade, 1996; Bayer et al., 1994; Duarte et al., 1994; Hespell and Whitehead, 1990; Wong et al, 1988), although these reference do not teach the inventive phytase molecules of the instant application, nor do they all teach the addition of phytase molecules in the production of foodstuffs, wood products, such as paper products, and as cleansing solutions and solids. In contrast, the instant invention teaches that phytase molecules—e.g., the phytase molecules of the instant invention—may be added to the reagent(s) disclosed in order to obtain preparations having an additional phytase activity. The reagent(s) and the additional phytase molecules may will not inhibit each other. The reagent(s) and the additional phytase molecules may have an overall additive effect. The reagent(s) and the additional phytase molecules may have an overall synergistic effect.

In a non-limiting aspect, the present invention provides a method (and products therefrom) for enhancement of phytate phosphorus utilization and treatment and prevention of tibial dyschondroplasia in animals, particularly poultry, by administering to animals a feed composition containing a hydroxylated vitamin $D_3$ derivative. The vitamin $D_3$ derivative can be administered to animals in feed containing reduced levels of calcium and phosphorus for enhancement of phytate phosphorus utilization. Accordingly, the vitamin $D_3$ derivative can be administered in combination with novel phytase molecules of the instant invention for further enhancement of phytate phosphorus utilization. Additional details regarding this approach are in the public literature and/or are known to the skilled artisan. In a particular non-limiting exemplification, such publicly available literature includes U.S. Pat. No. 5,516,525 (Edwards et al.) and U.S. Pat. No. 5,366,736 (Edwards et al.), U.S. Pat. No. 5,316,770 (Edwards et al.) although these reference do not teach the inventive molecules of the instant application.

In a non-limiting aspect, the present invention provides a method (and products therefrom) to obtain foodstuff that 1) comprises phytin that is easily absorbed and utilized in a form of inositol in a body of an organism; 2) that is capable of reducing phosphorus in excrementary matter; and 3) that is accordingly useful for improving environmental pollution. Said foodstuff is comprised of an admixture of a phytin-containing grain, a lactic acid-producing microorganism, and a novel phytase molecule of the instant invention. In a preferred embodiment, said foodstuff is produced by compounding a phytin-containing grain (preferably, e.g. rice bran) with an effective microbial group having an acidophilic property, producing lactic acid, without producing butyric acid, free from pathogenicity, and a phytase. Examples of an effective microbial group include e.g. *Streptomyces* sp. (ATCC 3004) belonging to the group of actinomyces and *Lactobacillus* sp. (IFO 3070) belonging to the group of lactobacilli. Further, a preferable amount of an effective microbial group to be added is 0.2 wt. % in terms of bacterial body weight based on a grain material. Furthermore, the amount of the phytase to be added is preferably 1–2 wt. % based on the phytin in the grain material. Additional details regarding this approach are in the public literature and/or are known to the skilled artisan. In a particular non-limiting exemplification, such publicly available literature includes JP 08205785 (Akahori et al.), although references in the publicly available literature do not teach the inventive molecules of the instant application.

In a non-limiting aspect, the present invention provides a method for improving the solubility of vegetable proteins. More specifically, the invention relates to methods for the solubilization of proteins in vegetable protein sources, which methods comprise treating the vegetable protein source with an effective amount of one or more phytase enzymes—including phytase molecules of the instant invention—and treating the vegetable protein source with an effective amount of one or more proteolytic enzymes. In another aspect, the invention provides animal feed additives comprising a phytase and one or more proteolytic enzymes. Additional details regarding this approach are in the public literature and/or are known to the skilled artisan. In a particular non-limiting exemplification, such publicly available literature includes EP 0756457 (WO 9528850 A1) (Nielsen and Knap), although references in the publicly available literature do not teach the inventive molecules of the instant application.

In a non-limiting aspect, the present invention provides a method of producing a plant protein preparation comprising dispersing vegetable protein source materials in water at a pH in the range of 2 to 6 and admixing phytase molecules of the instant invention therein. The acidic extract containing soluble protein is separated and dried to yield a solid protein of desirable character. One or more proteases can also be used to improve the characteristics of the protein. Additional details regarding this approach are in the public literature and/or are known to the skilled artisan. In a particular non-limiting exemplification, such publicly available literature includes U.S. Pat. No. 3,966,971 (Morehouse et al.), although references in the publicly available literature do not teach the inventive molecules of the instant application.

In a non-limiting aspect, the present invention provides a method (and products thereof) to activate inert phosphorus in soil and/or compost, to improve the utilization rate of a nitrogen compound, and to suppress propagation of pathogenic molds by adding three reagents, phytase, saponin and chitosan, to the compost. In a non-limiting embodiment the method can comprise treating the compost by 1) adding phytase-containing microorganisms in media—preferably recombinant hosts that overexpress the novel phytase molecules of the instant invention—e.g. at 100 ml media/100 kg wet compost; 2) alternatively also adding a phytase-containing plant source—such as wheat bran—e.g. at 0.2 to 1 kg/100 kg wet compost; 3) adding a saponin-containing source—such as peat, mugworts and yucca plants—e.g. at 0.5 to 3.0 g/kg; 4) adding chitosan-containing materials—such as pulverized shells of shrimps, crabs, etc.—e.g. at 100 to 300 g/kg wet compost. In another non-limiting embodiment, recombinant forms of the three reagents, phytase, saponin, and chitosan, are used. Additional details regarding this approach are in the public literature and/or are known to the skilled artisan. In a particular non-limiting exemplification, such publicly available literature includes JP 07277865 (Toya Taisuke), although references in the publicly available literature do not teach the inventive molecules of the instant application.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

In another aspect, transgenic non-human organisms are provided which contain a heterolgous sequence encoding a phytase of the invention (e.g., SEQ ID NO:2). Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a published procedure by Love et al., (*Biotechnol.*, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as is target for gene transfer has a major advantage in that in most cases the injected DNA will be incorporated into the host gene before the first cleavage (Brinster et al., *Proc. Natl. Acad. Sci.* USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles, 50% of the resulting animals will include the exogenous genetic material within one allele and 25% will include no exogenous genetic material.

In the microinjection method useful in the practice of the subject invention, the transgene is digested and purified free from any vector DNA, e.g., by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., *Proc. Natl. Acad. Sci.* USA 73:1260–1264, 1976). Efficient infection of the blastomeres is obtained by enzymatic treatment to remove the zona pellucida (Hogan, et al. (1986) in *Manipulating the Mouse Embryo*, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci.* USA 82: 6927–6931, 1985; Van der Putten, et al., *Proc. Natl. Acad. Sci.* USA 82: 6148–6152, 1985). Transfection is easily and efficiently obtained by culturing the blastomeres on a monolayer of virus-producing cells (Van der Putten, supra; Stewart, et al., *EMBO J.* 6: 383–388, 1987). Alternatively, infection can be performed at a later stage. Virus or virus-producing cells can be injected into the blastocoele (D. Jahner et al., *Nature* 298: 623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al., *Nature* 292:154–156, 1981; M. O. Bradley et al., *Nature* 309:255–258, 1984; Gossler, et al., *Proc. Natl. Acad. Sci.* USA 83:9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240:1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode phytases or polypeptides having phytase activity, and include polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one aspect, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a sequence coding for a phytase or a polypeptide having phytase activity. In one aspect, a polynucleotide having a sequence as set forth in SEQ ID NO:1 or a sequence encoding a polypeptide having a sequence as set forth in SEQ ID NO:2 is the transgene as the term is defined herein. Where appropriate, DNA sequences that encode proteins having phytase activity but differ in nucleic acid sequence due to the degeneracy of the genetic code may also be used herein, as may truncated forms, allelic variants and interspecies homologues.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood or tissue samples using transgene specific probes. PCR is particularly useful in this regard. Positive progeny (G0) are crossbred to produce offspring (G1) which are analyzed for transgene expression by Northern blot analysis of tissue samples.

Thus, the present invention includes methods for increasing the phosphorous uptake in the transgenic animal and/or decreasing the amount of politant in the manure of the transgenic organism by about 15%, about 20%, or about 20%, to about 50%.

The animals contemplated for use in the practice of the subject invention are those animals generally regarded as domesticated animals including pets (e.g., canines, felines, avian species etc.) and those useful for the processing of food stuffs, i.e., avian such as meat bred and egg laying chicken and turkey, ovine such as lamb, bovine such as beef cattle and milk cows, piscine and porcine. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

In some instances it may be advantageous to deliver and express a phytase sequence of the invention locally (e.g., within a particular tissue or cell type). For example, local expression of a phytase or digestive enzyme in the gut of an animal will assist in the digestion and uptake of, for example, phytate and phosporous, respectively. The nucleic sequence may be directly delivered to the salivary glands, tissue and cells and/or to the epithelial cells lining the gut, for example. Such delivery methods are known in the art and include electroporation, viral vectors and direct DNA uptake. Any polypeptide having phytase activity can be utilized in the methods of the invention (e.g., those specfically described under this subsection 6.3.18, as well as those described in other sections of the invention).

For example, a nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

One such delivery vehicles comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) *Circ. Res.* 71:1508–1517. A suitable adenovirus gene delivery is described in Rosenfeld et al. (1991) *Science* 252:431–434. Both retroviral and adenovirus delivery systems are described in Friedman (1989) *Science* 244:1275–1281.

A second type of nucleic acid delivery vehicle comprises liposomal transfection vesicles, including both anionic and cationic liposomal constructs. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. (1992) *Biochem. Biophys. Acta.* 1111:239–246. An exemplary material for forming liposomal vesicles is lipofectin which is composed of an equimolar mixture of dioleylphosphatidyl ethanolamine (DOPE) and dioleyloxypropyl-triethylammonium (DOTMA), as described in Felgner and Ringold (1989) *Nature* 337:387–388.

It is also possible to combine these two types of delivery systems. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. (1989) *Science* 243:375–378.

In another aspect, a digestive aid containing an enzyme either as the sole active ingredient or in combination with one or more other agents and/or enzymes is provided. The use of enzymes and other agents in digestive aids of livestock or domesticated animals not only improves the animal's health and life expectancy but also assists in increasing the health of livestock and in the production of foodstuffs from livestock.

Currently, some types of feed for livestock (e.g., certain poultry feed) are highly supplemented with numerous minerals (e.g., inorganic phosphorous), enzymes, growth factors, drugs, and other agents for delivery to the livestock. These supplements replace many of the calories and natural nutrients present in grain, for example.

By reducing or eliminating the inorganic phosphorous supplement and other supplements (e.g., trace mineral salts, growth factors, enzymes, antibiotics) from the feed itself, the feed is able to carry more nutrient and energy. Accordingly, the remaining diet would contain more usable energy. For example, grain-oilseed meal diets generally contain about 3,200 kcal metabolizable energy per kilogram of diet, and mineral salts supply no metabolizable energy. Removal of the unneeded minerals and substitution with grain therefore increase the usable energy in the diet. Thus, the invention is differentiated over commonly used phytase containing feed. For example, in one aspect, a biocompatible material is used that is resistant to digestion by the gastrointestinal tract of an organism.

In many organisms, including, for example, poultry or birds such as, for example, chickens, turkeys, geese, ducks, parrots, peacocks, ostriches, pheasants, quail, pigeons, emu, kiwi, loons, cockatiel, cockatoo, canaries, penguins, flamingoes, and dove, the digestive tract includes a gizzard which stores and uses hard biocompatible objects (e.g., rocks and shells from shell fish) to help in the digestion of seeds or other feed consumed by a bird. A typical digestive tract of this general family of organisms, includes the esophagus which contains a pouch, called a crop, where food is stored for a brief period of time. From the crop, food moves down into the true stomach, or proventriculus, where hydrochloric acid and pepsin starts the process of digestion. Next, food moves into the gizzard, which is oval shaped and thick walled with powerful muscles. The chief function of the gizzard is to grind or crush food particles—a process which is aided by the bird swallowing small amounts of fine gravel or grit. From the gizzard, food moves into the duodenum. The small intestine of birds is similar to mammals. There are two blind pouches or ceca, about 4–6 inches in length at the junction of the small and large intestine. The large intestine is short, consisting mostly of the rectum about 3–4 inches in length. The rectum empties into the cloaca and feces are excreted through the vent.

Hard, biocompatible objects consumed (or otherwise introduced) and presented in the gizzard provide a useful vector for delivery of various enzymatic, chemical, therapeutic and antibiotic agents. These hard substances have a life span of a few hours to a few days and are passed after a period of time. Accordingly, the invention provides coated, impregnated (e.g., impregnated matrix and membranes) modified dietary aids for delivery of useful digestive or therapeutic agents to an organism. Such dietary aids include objects which are typically ingested by an organism to assist in digestion within the gizzard (e.g., rocks or grit). The invention provides biocompatible objects that have coated thereon or impregnated therein agents useful as a digestive aid for an organism or for the delivery of a therapeutic or medicinal agent or chemical.

In one aspect, the invention provides a dietary aid, having a biocompatible composition designed for release of an agent that assists in digestion, wherein the biocompatible composition is designed for oral consumption and release in the digestive tract (e.g., the gizzard) of an organism. "Biocompatible" means that the substance, upon contact with a host organism (e.g., a bird), does not elicit a detrimental response sufficient to result in the rejection of the substance or to render the substance inoperable. Such inoperability may occur, for example, by formation of a fibrotic structure around the substance limiting diffusion of impregnated agents to the host organism therein or a substance which results in an increase in mortality or morbidity in the organism due to toxicity or infection. A biocompatible substance may be non-biodegradable or biodegradable. In one aspect, the biocompatible composition is resistant to degradation or digestion by the gastrointestinal tract. In another aspect, the biocompatible composition has the consistency of a rock or stone.

A non-biodegradable material useful in the invention is one that allows attachment or impregnation of a dietary agent. Such non-limiting non-biodegradable materials include, for example, thermoplastics, such as acrylic, modacrylic, polyamide, polycarbonate, polyester, polyethylene, polypropylene, polystyrene, polysulfone, polyethersulfone, and polyvinylidene fluoride. Elastomers are also useful materials and include, for example, polyamide, polyester, polyethylene, polypropylene, polystyrene, polyurethane, polyvinyl alcohol and silicone (e.g., silicone based or containing silica). The invention provides that the biocompatible composition can contain a plurality of such materials, which can be, e.g., admixed or layered to form blends, copolymers or combinations thereof.

As used herein, a "biodegradable" material means that the composition will erode or degrade in vivo to form smaller chemical species. Degradation may occur, for example, by enzymatic, chemical or physical processes. Suitable biodegradable materials contemplated for use in the invention include, but are not limited to, poly(lactide)s, poly(glycolide)s, poly(lactic acid)s, poly(glycolic acid)s, polyanhydrides, polyorthoesters, polyetheresters, polycaprolactone, polyesteramides, polycarbonate, polycyanoacrylate, polyurethanes, polyacrylate, and the like. Such materials can be admixed or layered to form blends, copolymers or combinations thereof.

It is contemplated that a number different biocompatible substances may be ingested or otherwise provided to the same organism simultaneously, or in various combinations (e.g., one material before the other). In addition, the biocompatible substance may be designed for slow passage through the digestive tract. For example, large or fatty substances tend to move more slowly through the digestive tract, accordingly, a biocompatible material having a large size to prevent rapid passing in the digestive tract can be used. Such large substances can be a combination of non-biodegradable and biodegradable substances. For example, a small non-biodegradable substance can be encompassed by a biodegradable substance such that over a period of time the biodegradable portion will be degraded allowing the non-biodegradable portion to pass through the digestive trace. In addition, it is recognized that any number of flavorings can be provided to the biocompatible substance to assist in consumption.

Any number of agents alone or in combination with other agents can be coated on the biocompatible substance including polypeptides (e.g., enzymes, antibodies, cytokines or therapeutic small molecules), and antibiotics, for example. Examples of particular useful agents are listed in Table 1 and 2, below. It is also contemplated that cells can be encapsulated into the biocompatible material of the invention and used to deliver the enzymes or therapeutics. For example, porous substances can be designed that have pores large enough for cells to grow in and through and that these porous materials can then be taken into the digestive tract. For example, the biocompatible substance can be comprised of a plurality of microfloral environments (e.g., different porosity, pH etc.) that provide support for a plurality of cell types. The cells can be genetically engineered to deliver a particular drug, enzyme or chemical to the organism. The cells can be eukaryotic or prokaryotic.

TABLE 1

| Treatment Class | Chemical | Description |
|---|---|---|
| Antibiotics | Amoxycillin and Its Combination Mastox Injection (Amoxycillin and Cloxacillin) | Treatment Against Bacterial Diseases Caused By Gram + and Gram − Bacteria |
| | Ampicillin and Its Combination Biolox Injection (Ampicillin and Cloxacillin) | Treatment Against Bacterial Diseases Caused By Gram + And Gram − Bacteria. |
| | Nitrofurazone + Urea Nefrea Bolus | Treatment Of Genital Infections |
| | Trimethoprim + Sulphamethoxazole Trizol Bolus | Treatment Of Respiratory Tract Infections, Gastro Intestinal Tract Infections, Urino-Genital Infections. |
| | Metronidazole and Furazolidone Metofur Bolus | Treatment Of Bacterial And Protozoal Diseases. |
| | Phthalylsulphathiazole, Pectin and Kaolin Pectolin Bolus Suspension | Treatment Of Bacterial And Non-Specific Diarrhoea, Bacillary Dysentery And Calf Scours. |
| Antihelmintics | Ectoparasiticide Germex Ointment (Gamma Benzene Hexachloride, Proflavin Hemisulphate and Cetrimide) | Ectoparasiticide and Antiseptic |
| | Endoparasiticides > Albendazole and Its Combination Alben (Albendazole) Suspension (Albendazole 2.5%) Plus Suspension (Albendazole 5%) Forte Bolus (Albendazole 1.5 Gm.) Tablet (Albendazole 600 Mg.) Powder (Albendazole 5%, 15%) | Prevention And Treatment Of Roundworm, Tapeworm and Fluke Infestations |
| | Alpraz (Albendazole and Praziquantel) Tablet | Prevention And Treatment Of Roundworm and Tapeworm Infestation In Canines and Felines. |
| | Oxyclozanide and Its Combination Clozan (Oxyclozanide) Bolus, Suspension | Prevention and Treatment Of Fluke Infestations |

TABLE 1-continued

| Treatment Class | Chemical | Description |
|---|---|---|
| | Tetzan (Oxyclozanide and Tetramisole Hcl) Bolus, Suspension | Prevention and Treatment Of Roundworm and Fluke Infestations |
| | Fluzan (Oxyclozanide and Levamisole Hcl) Bolus, Suspension | Prevention and Treatment Of Roundworm Infestations and Increasing Immunity |
| | Levamisole Nemasol Injection Wormnil Powder | Prevention and Treatment Of Roundworm Infestations and Increasing Immunity. |
| | Fenbendazole Fenzole Tablet (Fenbendazole 150 Mg.) Bolus (Fenbendazole 1.5 Gm.) Powder (Fenbendazole 2.5% W/W) | Prevention And Treatment of Roundworm and Tapeworm Infestations |
| Tonics | Vitamin B Complex, Amino Acids and Liver Extract Heptogen Injection | Treatment Of Anorexia, Hepatitis, Debility, Neuralgic Convulsions Emaciation and Stunted Growth. |
| | Calcium Levulinate With Vit. $B_{12}$ and Vit $D_3$ Hylactin Injection | Prevention and treatment of hypocalcaemia, supportive therapy in sick conditions (especially hypothermia) and treatment of early stages of rickets. |
| Animal Feed Supplements | Essential Minerals, Selenium and Vitamin E | Treatment Of Anoestrus Causing Infertility and Repeat Breeding In Dairy Animals and Horses. |
| | Gynolactin Bolus | |
| | Essential Minerals, Vitamin E, and Iodine Hylactin Powder | Infertility, Improper Lactation, Decreased Immunity, Stunted Growth and Debility. |
| | Essential Electrolytes With Vitamin C Electra—C Powder | Diarrhoea, Dehydration, Prior to and after Transportation, In Extreme temperatures (High Or Low) and other Conditions of stress. |
| | Pyrenox Plus (Diclofenac Sodium + Paracetamol) Bolus, Injection. | Treatment Of Mastitis, Pyrexia Post Surgical Pain and Inflammation, Prolapse Of Uterus, Lameness and Arthritis. |

TABLE 2

Therapeutic Formulations

| Product | Description |
|---|---|
| Acutrim ® (phenylpropanolamine) | Once-daily appetite suppressant |
| The Baxter ® Infusor | For controlled intravenous delivery of anti-coagulants, anitbiotics, chemotherapeutic agents, and other widely used drugs. |
| Catapres-TTS ® (clonidine transdermal therapeutic system) | Once-weekly transdermal system for the treatment of hypertension. |
| Covera HS ™ (verapamil hydrochloride) | Once-daily Controlled-Onset Extended-Release (COER-24) tablets for the treatment of hypertension and angina pectoris. |
| DynaCirc CR ® (isradipine) | Once-daily extended release tablets for the treatment of hypertension. |
| Efidac 24 ® (chlorpheniramine maleate) | Once-daily extended release tablets for the relief of allergy symptoms. |
| Estraderm ® (estradiol transdermal system) | Twice-weekly transdermal system for treating certain postmenopausal symptoms and preventing osteoporosis |

TABLE 2-continued

Therapeutic Formulations

| Product | Description |
|---|---|
| Glucotrol XL ® (glipizide) | Once-daily extended release tablets used as an adjunct to diet for the control of hyperglycemia in patients with non-insulin-dependent diabetes mellitus. |
| IVOMEC SR ® Bolus (ivermectin) | Ruminal delivery system for season-long control of major internal and external parasites in cattle. |
| Minipress XL ® (prazosin) | Once-daily extended release tablets for the treatment of hypertension. |
| NicoDerm ® CQ ™ (nicotine transdermal system) | Transdermal system used as a once-daily aid to smoking cessation for relief of nicotine withdrawal symptoms. |
| Procardia XL ® (nifedipine) | Once-daily extended release tablets for the treatment of angina and hypertension. |
| Sudafed ® 24 Hour (pseudoephedrine) | Once-daily nasal decongestant for relief of colds, sinusitis, hay fever and other respiratory allergies. |
| Transderm-Nitro ® (nitroglycerin transdermal system) | Once-daily transdermal system for the prevention of angina pectoris due to coronary artery disease. |
| Transderm Scop ® (scopolamin transdermal system) | Transdermal system for the prevention of nausea and vomiting associated with motion sickness. |
| Volmax (albuterol) | Extended release tablets for relief of bronchospasm in patients with reversible obstructive airway disease. |
| Actisite ® | (tetracycline hydrochloride) Periodontal fiber used as an adjunct to scaling and root planing for reduction of pocket depth and bleeding on probing in patients with adult periodontitis. |
| ALZET ® | Osmotic pumps for laboratory research. |
| Amphotec ® (amphotericin B cholesteryl sulfate complex for injection) | AMPHOTEC ® is a fungicidal treatment for invasive aspergillosis in patients where renal impairment or unacceptable toxicity precludes use of amphotericin B in effective doses and in patients with invasive aspergillosis where prior amphotericin B therapy has failed. |
| BiCitra ® (sodium citrate and citric acid) | Alkalinizing agent used in those conditions where long-term maintenance of alkaline urine is desirable. |
| Ditropan ® (oxybutynin chloride) | For the relief of symptoms of bladder instability associated with uninhibited neurogenic or reflex neurogenic bladder (i.e., urgency, frequency, urinary leakage, urge incontinence, dysuria). |
| Ditropan ® XL (oxybutynin chloride) | is a once-daily controlled-release tablet indicated for the treatment of overactive bladder with symptoms of urge urinary incontinence, urgency and frequency. |
| DOXIL ® (doxorubicin HCl liposome injection) | |
| Duragesic ® (fentanyl transdermal system) CII | 72-hour transdermal system for management of chronic pain in patients who require continuous opioid analgesia for pain that cannot be managed by lesser means such as acetaminophen-opioid combinations, non-steroidal analgesics, or PRN dosing with short-acting opioids. |
| Elmiron ® (pentosan polysulfate sodium) | Indicated for the relief of bladder pain or discomfort associated with interstitial cystitis. |
| ENACT AirWatch ™ | An asthma monitoring and management system. |
| Ethyol ® (amifostine) | Indicated to reduce the cumulative renal toxicity associated with repeated administration of cisplatin in patients with advanced ovarian cancer or non-small cell lung cancer. Indicated to reduce the incidence of moderate to severe xerostomia in patients undergoing postoperative radiation treatment for head and neck cancer, where the radiation port includes a substantial portion of the parotid glands. |
| Mycelex ® Troche (clotrimazole) | For the local treatment of oropharyngeal candidiasis. Also indicated prophylactically to reduce the incidence of oropharyngeal candidiasis in patients immunocompromised by conditions that include chemotherapy, radiotherapy, or steroid therapy utilized in the treatment of leukemia, solid tumors, or renal transplantation. |

TABLE 2-continued

Therapeutic Formulations

| Product | Description |
|---|---|
| Neutra-Phos ® (potassium and sodium phosphate) | a dietary/nutritional supplement |
| PolyCitra ®-K Oral Solution and PolyCitra ®-K Crystals (potassium citrate and citric acid) | Alkalinizing agent useful in those conditions where long-term maintenance of an alkaline urine is desirable, such as in patents with uric acid and cystine calculi of the urinary tract, especially when the administration of sodium salts is undesirable or contraindicated |
| PolyCitra ®-K Syrup and LC (tricitrates) | Alkalinizing agent useful in those conditions where long-term maintenance of an alkaline urine is desirable, such as in patients with uric acid and cystine calculi of the urinary tract. |
| Progestasert ® (progesterone) | intrauterine Progesterone Contraceptive System |
| Testoderm ® Testoderm ® with Adhesive and Testoderm ® TTS CIII | Testosterone Transdermal System The Testoderm ® products are indicated for replacement therapy in males for conditions associated with a deficiency or absence of endogenous testosterone: (1) Primary hypogonadism (congenital or acquired) or (2) Hypogonadotropic hypogonadism (congenital or acquired). |
| Viadur ™ (leuprolide acetate implant) | Once-yearly implant for the palliative treatment of prostate cancer |

Certain agents can be designed to become active or inactivated under certain conditions (e.g., at certain pH's, in the presence of an activating agent etc.). In addition, it may be advantageous to use pro-enzymes in the compositions of the invention. For example, a pro-enzymes can be activated by a protease (e.g., a salivary protease that is present in the digestive tract or is artificially introduced into the digestive tract of an organism). It is contemplated that the agents delivered by the biocompatible compositions of the invention are activated or inactivated by the addition of an activating agent which may be ingested by, or otherwise delivered to, the organism. Another mechanism for control of the agent in the digestive tract is an environment sensitive agent that is activated in the proper digestive compartment. For example, an agent may be inactive at low pH but active at neutral pH. Accordingly, the agent would be inactive in the gut but active in the intestinal tract. Alternatively, the agent can become active in response to the presence of a microorganism specific factor (e.g., microorganisms present in the intestine).

Accordingly, the potential benefits of the present invention include, for example, (1) reduction in or possible elimination of the need for mineral supplements (e.g., inorganic phosphorous supplements), enzymes, or therapeutic drugs for animal (including fish) from the daily feed or grain thereby increasing the amount of calories and nutrients present in the feed, and (2) increased health and growth of domestic and non-domestic animals including, for example, poultry, porcine, bovine, equine, canine, and feline animals.

A large number of enzymes can be used in the methods and compositions of the present invention in addition to the phytases of the invention. These enzymes include enzymes necessary for proper digestion of consumed foods, or for proper metabolism, activation or derivation of chemicals, prodrugs or other agents or compounds delivered to the animal via the digestive tract. Examples of enzymes that can be delivered or incorporated into the compositions of the invention, include, for example, feed enhancing enzymes selected from the group consisting of α-galactosidases, β-galactosidases, in particular lactases, phytases, β-glucanases, in particular endo-β-1,4-glucanases and endo-β-1,3 (4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phytases and cutinases. Phytases in addition to the phytases having an amino acid sequence as set forth in SEQ ID NO:2 can be used in the methods and compositions of the invention.

In one aspect, the enzyme used in the compositions (e.g., a dietary aid) of the present invention is a phytase enzyme which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of above 50° C.

A "feed" and a "food," respectively, means any natural or artificial diet, meal or the like or components of such meals intended or suitable for being eaten, taken in, digested, by an animal and a human being, respectively. "Dietary Aid," as used herein, denotes, for example, a composition containing agents that provide a therapeutic or digestive agent to an animal or organism. A "dietary aid," typically is not a source of caloric intake for an organism, in other words, a dietary aid typically is not a source of energy for the organism, but rather is a composition which is taken in addition to typical "feed" or "food".

In various aspects of the invention, feed composition are provided that comprise a recombinant phytase protein having at least thirty contiguous amino acids of a protein having an amino acid sequence of SEQ ID NO:2; and a phytate-containing foodstuff. As will be known to those skilled in the art, such compositions may be prepared in a number of ways, including but not limited to, in pellet form with or without polymer coated additives, in granulate form, and by spray drying. By way of non-limiting example, teachings in the art directed to the preparation of feed include International Publication Nos. WO0070034 A1, WO0100042 A1, WO0104279 A1, WO0125411 A1, WO0125412 A1, and EP 1073342A.

An agent or enzyme (e.g., a phytase) may exert its effect in vitro or in vivo, i.e. before intake or in the stomach or gizzard of the organism, respectively. Also a combined action is possible.

Although any enzyme may be incorporated into a dietary aid, reference is made herein to phytase as an exemplification of the methods and compositions of the invention. A dietary aid of the invention includes an enzyme (e.g., a phytase). Generally, a dietary aid containing a phytase composition is liquid or dry.

Liquid compositions need not contain anything more than the enzyme (e.g. a phytase), preferably in a highly purified form. Usually, however, a stabilizer such as glycerol, sorbitol or mono propylene glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a biocompatible composition for slow release. Preferably the enzyme is added to a dietary aid composition that is a biocompatible material (e.g., biodegradable or non-biodegradable) and includes the addition of recombinant cells into, for example, porous microbeads.

Dry compositions may be spray dried compositions, in which case the composition need not contain anything more than the enzyme in a dry form. Usually, however, dry compositions are so-called granulates which may readily be mixed with a food or feed components, or more preferably, form a component of a pre-mix. The particle size of the enzyme granulates preferably is compatible with that of the other components of the mixture. This provides a safe and convenient means of incorporating enzymes into animal feed. Preferably the granulates are biocompatible and more preferably they biocompatible granulates are non-biodegradable.

Agglomeration granulates coated by an enzyme can be prepared using agglomeration technique in a high shear mixer. Absorption granulates are prepared by having cores of a carrier material to absorb/be coated by the enzyme. Preferably the carrier material is a biocompatible non-biodegradable material that simulates the role of stones or grit in the gizzard of an animal. Typical filler materials used in agglomeration techniques include salts, such as disodium sulphate. Other fillers are kaolin, talc, magnesium aluminum silicate and cellulose fibers. Optionally, binders such as dextrins are also included in agglomeration granulates. The carrier materials can be any biocompatible material including biodegradable and non-biodegradable materials (e.g., rocks, stones, ceramics, various polymers). Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, the dietary aid compositions (e.g., phytase dietary aid compositions) may contain other substituents such as coloring agents, aroma compounds, stabilizers, vitamins, minerals, other feed or food enhancing enzymes etc. A typical additive usually comprises one or more compounds such as vitamins, minerals or feed enhancing enzymes and suitable carriers and/or excipients.

In one aspect, the dietary aid compositions of the invention additionally comprise an effective amount of one or more feed enhancing enzymes, in particular feed enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phytases and cutinases.

The animal dietary aid of the invention is supplemented to the mono-gastric animal before or simultaneously with the diet. In one aspect, the dietary aid of the invention is supplemented to the mono-gastric animal simultaneously with the diet. In another aspect, the dietary aid is added to the diet in the form of a granulate or a stabilized liquid.

An effective amount of an enzyme in a dietary aid of the invention is from about 10–20,000; from about 10 to 15,000, from about 10 to 10,000, from about 100 to 5,000, or from about 100 to about 2,000 FYT/kg dietary aid.

Non-limiting examples of other specific uses of the phytase of the invention is in soy processing and in the manufacture of inositol or derivatives thereof.

The invention also relates to a method for reducing phytate levels in animal manure, wherein the animal is fed a dietary aid containing an effective amount of the phytase of the invention. As stated in the beginning of the present application one important effect thereof is to reduce the phosphate pollution of the environment.

In another aspect, the dietary aid is a magnetic carrier. For example, a magnetic carrier containing an enzyme (e.g., a phytase) distributed in, on or through a magnetic carrier (e.g., a porous magnetic bead), can be distributed over an area high in phytate and collected by magnets after a period of time. Such distribution and recollection of beads reduces additional pollution and allows for reuse of the beads. In addition, use of such magnetic beads in vivo allows for the localization of the dietary aid to a point in the digestive tract where, for example, phytase activity can be carried out. For example, a dietary aid of the invention containing digestive enzymes (e.g., a phytase) can be localized to the gizzard of the animal by juxtapositioning a magnet next to the gizzard of the animal after the animal consumes a dietary aid of magnetic carriers. The magnet can be removed after a period of time allowing the dietary aid to pass through the digestive tract. In addition, the magnetic carriers are suitable for removal from the organism after sacrificing or to aid in collection.

When the dietary aid is a porous particle, such particles are typically impregnated by a substance with which it is desired to release slowly to form a slow release particle. Such slow release particles may be prepared not only by impregnating the porous particles with the substance it is desired to release, but also by first dissolving the desired substance in the first dispersion phase. In this case, slow release particles prepared by the method in which the substance to be released is first dissolved in the first dispersion phase are also within the scope and spirit of the invention. The porous hollow particles may, for example, be impregnated by a slow release substance such as a medicine, agricultural chemical or enzyme. In particular, when porous hollow particles impregnated by an enzyme are made of a biodegradable polymers, the particles themselves may be used as an agricultural chemical or fertilizer, and they have no adverse effect on the environment. In one aspect the porous particles are magnetic in nature.

The porous hollow particles may be used as a bioreactor support, in particular an enzyme support. Therefore, it is advantageous to prepare the dietary aid utilizing a method of a slow release, for instance by encapsulating the enzyme of agent in a microvesicle, such as a liposome, from which the dose is released over the course of several days, preferably between about 3 to 20 days. Alternatively, the agent (e.g., an enzyme) can be formulated for slow release, such as incorporation into a slow release polymer from which the dosage of agent (e.g., enzyme) is slowly released over the course of several days, for example from 2 to 30 days and can range up to the life of the animal.

As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. Some preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

Also within the scope of the invention is the use of a phytase of the invention during the preparation of food or feed preparations or additives, i.e., the phytase exerts its phytase activity during the manufacture only and is not active in the final food or feed product. This aspect is relevant for instance in dough making and baking. Accordingly, phytase or recombinant yeast expressing phytase can be impregnated in, on or through a magnetic carriers, distributed in the dough or food medium, and retrieved by magnets.

The dietary aid of the invention may be administered alone to animals in an biocompatible (e.g., a biodegradable or non-biodegradable) carrier or in combination with other digestion additive agents. The dietary aid of the invention thereof can be readily administered as a top dressing or by mixing them directly into animal feed or provided separate from the feed, by separate oral dosage, by injection or by transdermal means or in combination with other growth related edible compounds, the proportions of each of the compounds in the combination being dependent upon the particular organism or problem being addressed and the degree of response desired. It should be understood that the specific dietary dosage administered in any given case will be adjusted in accordance with the specific compounds being administered, the problem to be treated, the condition of the subject and the other relevant facts that may modify the activity of the effective ingredient or the response of the subject, as is well known by those skilled in the art. In general, either a single daily dose or divided daily dosages may be employed, as is well known in the art.

If administered separately from the animal feed, forms of the dietary aid can be prepared by combining them with non-toxic pharmaceutically acceptable edible carriers to make either immediate release or slow release formulations, as is well known in the art. Such edible carriers may be either solid or liquid such as, for example, corn starch, lactose, sucrose, soy flakes, peanut oil, olive oil, sesame oil and propylene glycol. If a solid carrier is used the dosage form of the compounds may be tablets, capsules, powders, troches or lozenges or top dressing as micro-dispersible forms. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances. A process for preparing a granulate edible carrier at high temperature for release of enzyme when ingested is described in copending U.S. patent application Ser. No. 09/910,579, filed Jul. 20, 2001.

Thus, a significant advantages of the invention include for example, 1) ease of manufacture of the active ingredient loaded biocompatible compositions; 2) versatility as it relates to the class of polymers and/or active ingredients which may be utilized; 3) higher yields and loading efficiencies; and 4) the provision of sustained release formulations that release active, intact active agents in vivo, thus providing for controlled release of an active agent over an extended period of time. In addition, another advantage is due to the local delivery of the agent with in the digestive tract (e.g., the gizzard) of the organism. As used herein the phrase "contained within" denotes a method for formulating an agent into a composition useful for controlled release, over an extended period of time of the agent.

In the sustained-release or slow release compositions of the invention, an effective amount of an agent (e.g., an enzyme or antibiotic) will be utilized. As used herein, sustained release or slow release refers to the gradual release of an agent from a biocompatible material, over an extended period of time. The sustained release can be continuous or discontinuous, linear or non-linear, and this can be accomplished using one or more biodegradable or non-biodegradable compositions, drug loadings, selection of excipients, or other modifications. However, it is to be recognized that it may be desirable to provide for a "fast" release composition, that provides for rapid release once consumed by the organism. It is also to be understood that "release" does not necessarily mean that the agent is released from the biocompatible carrier. Rather in one aspect, the slow release encompasses slow activation or continual activation of an agent present on the biocompatible composition. For example, a phytase need not be released from the biocompatible composition to be effective. In this aspect, the phytase is immobilized on the biocompatible composition.

The animal feed may be any protein-containing organic meal normally employed to meet the dietary requirements of animals. Many of such protein-containing meals are typically primarily composed of corn, soybean meal or a corn/soybean meal mix. For example, typical commercially available products fed to fowl include Egg Maker Complete, a poultry feed product of Land O'Lakes AG Services, as well as Country Game and Turkey Grower a product of Agway, Inc. (see also The Emu Farmer's Handbook by Phillip Minnaar and Maria Minnaar). Both of these commercially available products are typical examples of animal feeds with which the present dietary aid and/or the enzyme phytase may be incorporated to reduce or eliminate the amount of supplemental phosphorus, zinc, manganese and iron intake required in such compositions.

The present invention is applicable to the diet of numerous animals, which herein is defined as including mammals (including humans), fowl and fish. In particular, the diet may be employed with commercially significant mammals such as pigs, cattle, sheep, goats, laboratory rodents (rats, mice, hamsters and gerbils), fur-bearing animals such as mink and fox, and zoo animals such as monkeys and apes, as well as domestic mammals such as cats and dogs. Typical commercially significant avian species include chickens, turkeys, ducks, geese, pheasants, emu, ostrich, loons, kiwi, doves, parrots, cockatiel, cockatoo, canaries, penguins, flamingoes, and quail. Commercially farmed fish such as trout would also benefit from the dietary aids disclosed herein. Other fish that can benefit include, for example, fish (especially in an aquarium or aquaculture environment, e.g., tropical fish), goldfish and other ornamental carp, catfish, trout, salmon, shark, ray, flounder, sole, tilapia, medaka, guppy, molly, platyfish, swordtail, zebrafish, and loach.

Measuring Metabolic Parameters

The methods of the invention involve whole cell evolution, or whole cell engineering, of a cell to develop a new cell strain having a new phenotype by modifying the genetic composition of the cell, where the genetic composition is modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line."

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available.

Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript or generating new transcripts in a cell. mRNA transcript, or message can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR;

quantitative real time RT-PCR, or "real-time kinetic RT-PCR" (see, e.g., Kreuzer (2001) Br. J. Haematol. 114: 313–318; Xia (2001) Transplantation 72:907–914).

In one aspect of the invention, the engineered phenotype is generated by knocking out expression of a homologous gene. The gene's coding sequence or one or more transcriptional control elements can be knocked out, e.g., promoters enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element.

As discussed below in detail, one or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide or generating new polypeptides in a cell. Polypeptides, peptides and amino acids can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Biosynthetically directed fractional $^{13}$C labeling of proteinogenic amino acids can be monitored by feeding a mixture of uniformly $^{13}$C-labeled and unlabeled carbon source compounds into a bioreaction network. Analysis of the resulting labeling pattern enables both a comprehensive characterization of the network topology and the determination of metabolic flux ratios of the amino acids; see, e.g., Szyperski (1999) Metab. Eng. 1:189–197.

The following examples are intended to illustrate, but not to limit, the invention. While the procedures described in the examples are typical of those that can be used to carry out certain aspects of the invention, other procedures known to those skilled in the art can also be used.

EXAMPLE 1

Figure 8A:
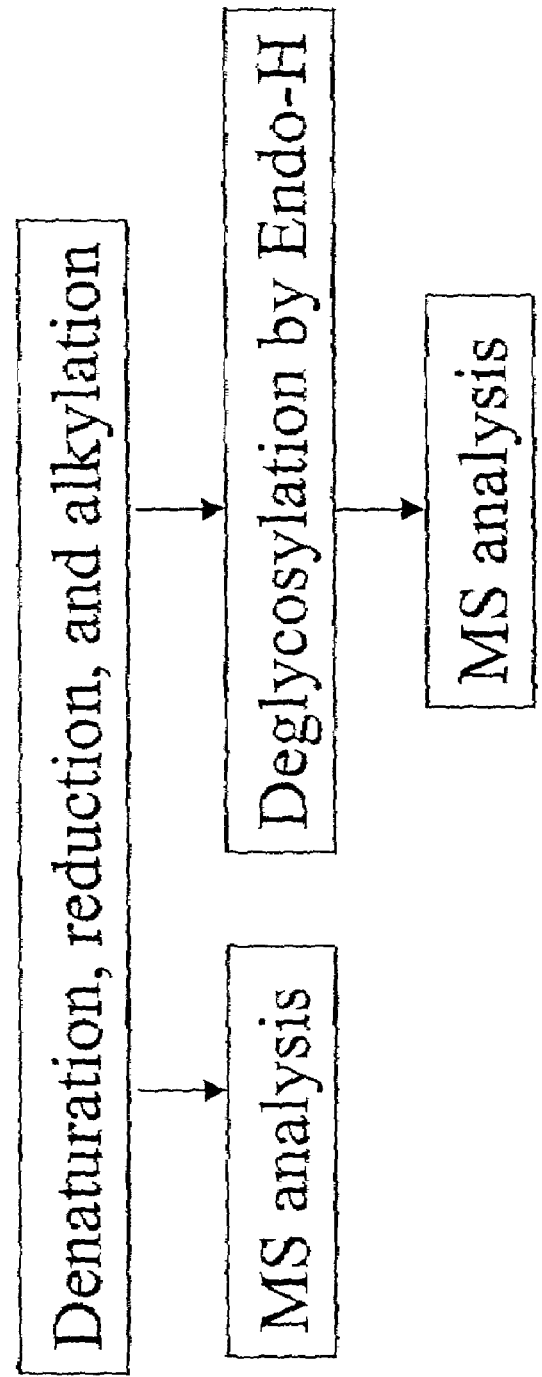
FIG. 8A presents a schematic depicting the steps for maximum peptide mapping.
Figure 8B:
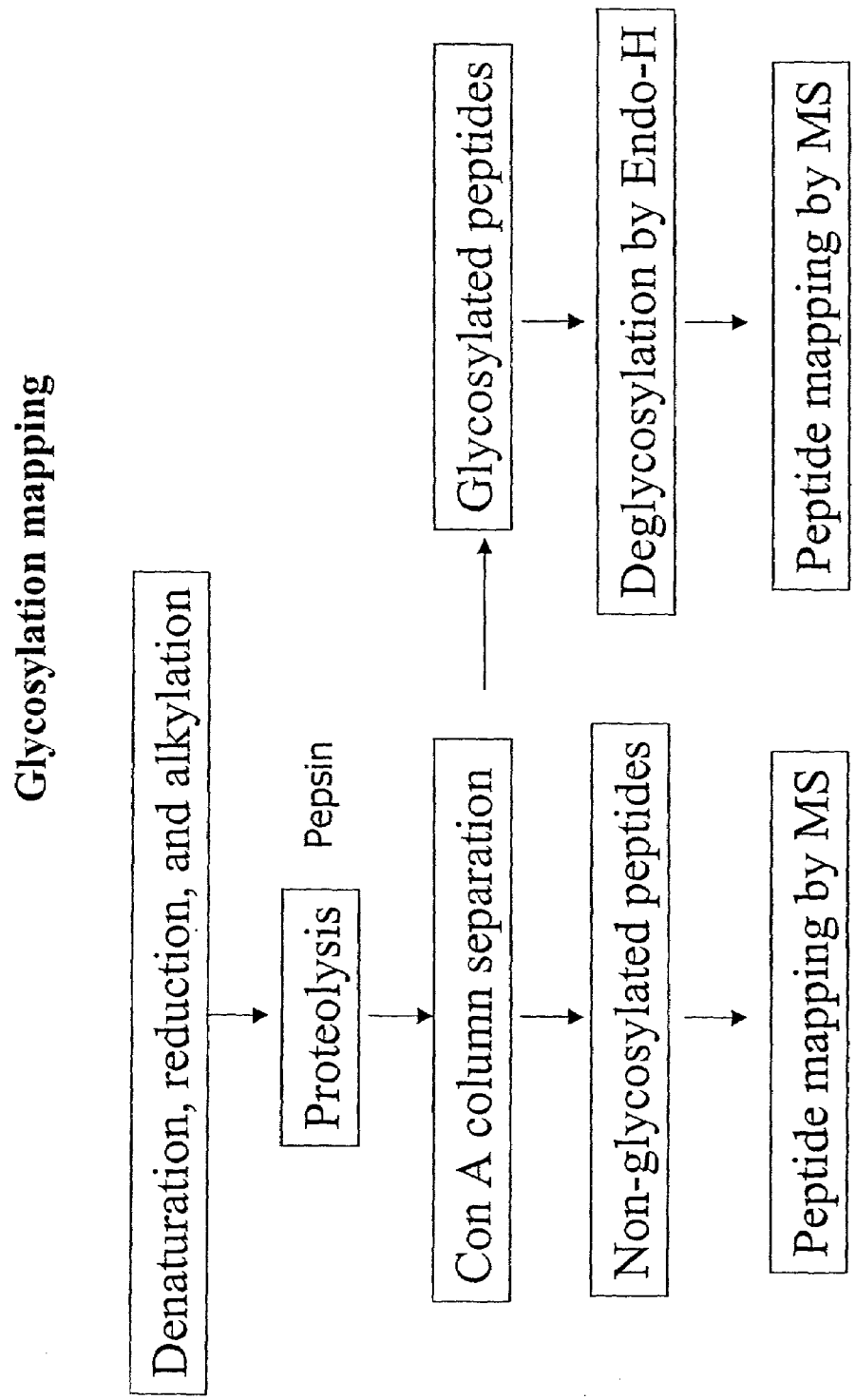
FIG. 8B presents a schematic depicting the steps for glycosylation peptide mapping.

The wild type phytase appA gene from *E. coli* (strain K12) (SEQ ID NO:3) (FIG. 13), which encodes a wild type phytase (SEQ ID NO:4) (FIG. 14), was used to prepare a GSSM-modified polynucleotide. The modified polynucleotide having a sequence as set forth in SEQ ID NO:1 (FIG. 1A) encodes a non-glycosylated phytase (SEQ ID NO:2) (FIG. 1B). Specifically GSSM was employed to find single point mutations that enhanced the thermotolerance of the *E. coli* K12 appA. Eight variant polynucleotides that contained point mutations that enhanced thermotolerance were identified. These eight mutations were combined into a single protein as shown in FIGS. 8A and 8B.

Figure 3:
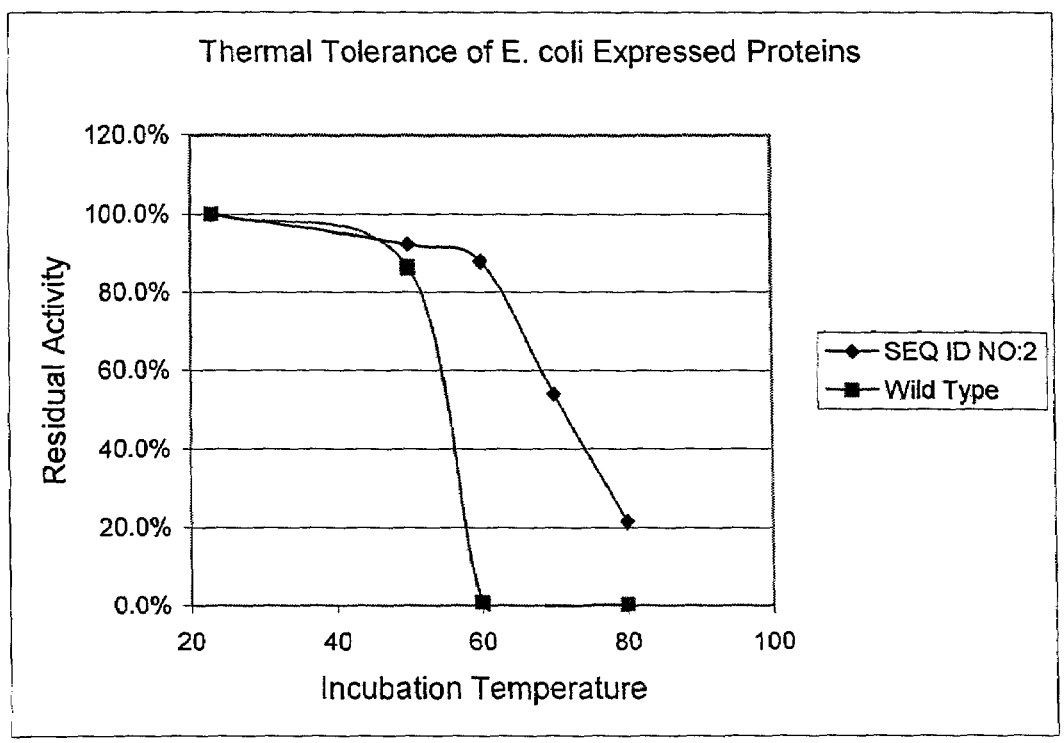
FIG. 3 shows a graph with the results of a thermal tolerance assay between SEQ ID NO:4 (wild type phytase) and SEQ ID NO:2 (modified phytase). The graph shows residual phytase activity in a simulated gastric intestinal fluid (SGF) with pepsin. The percent residual activities (based on initial rates) of the in vitro digested invention recombinant phytase (SEQ ID NO:2) expressed in various expression hosts were plotted verses time. The phytase was expressed in E. coli (non-glycosylated), as well as in S. pombe and P. pastoris (glycosylated).

The wild type and mutagenized polynucleotides were expressed in *E. coli* and purified to homogeneity. In the thermal tolerance assay, 100 µL of 0.01 mg/mL of protein in 100 mM MOPS/pH 7.0 was heated to 37° C., 50° C., 60° C., 70° C., 80° C. or 90° C. in an RJ research thermocycler. Upon completion of the 5 minutes at the incubation temperature, the samples were cooled to 4° C. and incubated on ice. An activity assay was run using 40 uL of the enzyme solution in 1.5 mL of 100 mM NaOAc/4 mM phytate/pH 4.5 at 37° C. Aliquots of 60 uL were withdrawn at 2 minute intervals and added to 60 uL of the color developer/Stop solution of the TNO assay, which is known in the art as the industry standard for detecting phosphate in a solution, as described in A. J. Engelen et al. ("Related Articles Simple and rapid determination of phytase activity," *J. AOAC Int.* 1994 May–Jun 77(3):760–4). Clearly, the modified enzyme, SEQ ID NO:2, containing 8 amino acid changes as compared to the wild type appA enzyme of *E. coli*, is tolerant to temperatures greater than the wild type enzyme. (see FIG. 3).

EXAMPLE 2

Stability of Phytase Enzyme in Simulated Digestibility Conditions

Figure 4:
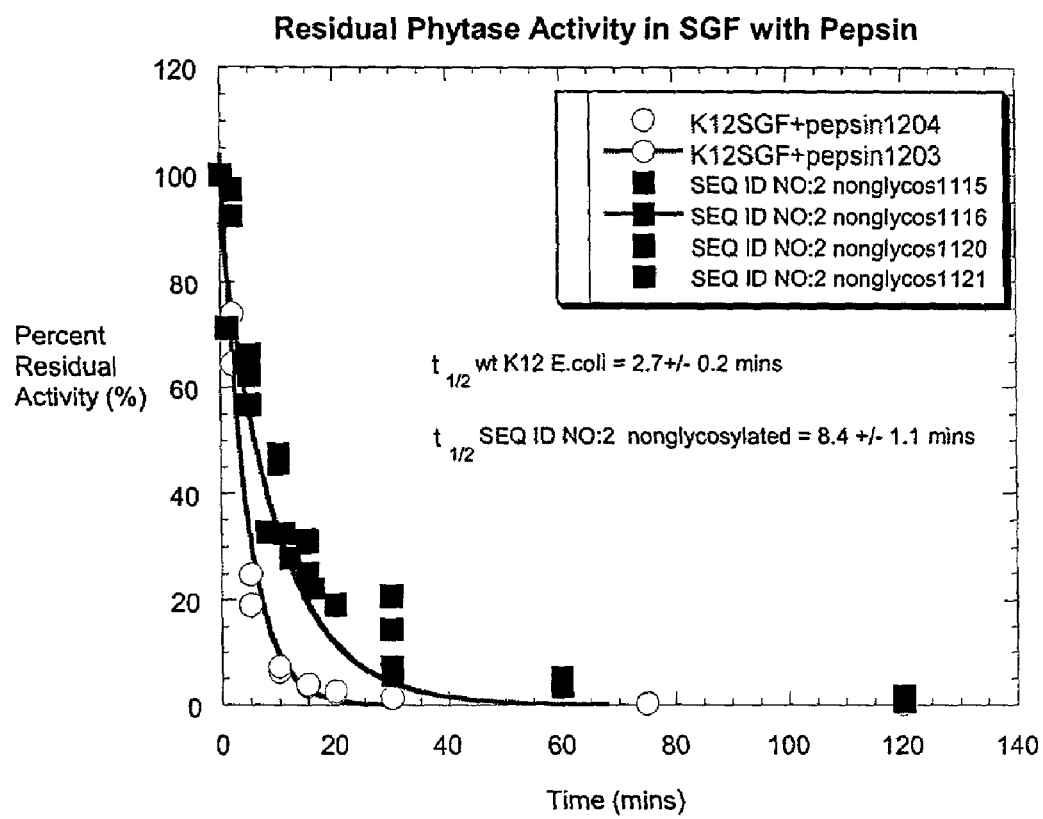
FIG. 4 shows a graph showing the percent residual activity of the K12SGF phytase and the SEQ ID NO:2 phytase (non-glycosylated) under simulated digestibility conditions using pepsin as a simulated gastric intestinal fluid.

The present example shows the effect of a simulated gastric intestinal fluid on digestion of glycosylated and non-glycosylated phytase of SEQ ID NO:2. The percent residual activities (based on initial rates) of the in vitro digested *E. coli* K12 and the non-glycosylated phytase of SEQ ID NO:2 were plotted verses time. A standard concentration of simulated gastric intestinal fluid (SGIF) containing 2 mg/ml NaCl, 6 M HCl and 3.2 mg/mL pepsin was prepared as described. The pH of the solution was about 1.4 and was not adjusted. The in vitro digestibility assay was performed by adding 1:4 (vol:vol) of phytase to digestion solution and immediately incubating at 37° C. to initiate the digestion reaction. Aliquots of the digestion reaction mixture were removed at various time intervals and assayed for residual phytase activity using the TNO assay. Each of the assays was performed at least twice. An exponential curve with the equation y=Ae−kt was fit to the data. The half lives of the proteins were determined using the equation t½=ln 2/k. The half-life of the *E. coli* K12 phytase was only 2.7±0.2 minutes while the non-glycosylated phytase of SEQ ID NO:2 had a half-life of 8.4±1.1 minutes. Therefore, the mutations in the wildtype *E. coli* K12 phytase enhanced the stability of the enzyme under simulated in vitro digestibility conditions. See FIG. 4.

EXAMPLE 3

Glycosylation Stabilizes Phytase to Pepsin Digestion

Experiments were conducted to evaluate the effect of glycosylation on the half life of phytase enzyme activity exposed to pepsin, used as a simulated intestinal gastric fluid since pepsin is one of the major components of intestinal gastric fluid. Results of studies examining the half life of phytase exposed to pepsin are presented in FIG. 5. These results indicated that glycosylated forms of phytase have longer half-life than un-glycosylated forms of the enzyme.

Computer analysis provides a means of predicting putative amino acid residues that are post-translationally modified by glycosylation. The prediction of glycosylated sites of phytase was done using the Post-translational Modification Prediction program on the world wide web at address expasy.ch. The glycosylated peptide identification was mapped by PeptideMass program in the same website. Predicted glycosylation sites for phytase are presented in FIG. 6.

Studies were then undertaken to determine the type of glycosylation on phytase expressed in *Pichia pastoris* and *S. cerevisiae*. After protein purification from the respective organisms, putative O-glycosylated chains were removed from the protein by addition of 1 mU of O-glycosidase (Roche Molecular Biochemicals, Germany) to 50 µg of phytase in a buffer containing 20 mM Tris, pH 7.5 followed by incubation at 37° C. overnight. N-glycosylated chains were removed by adding 50 mU of Endoglycosidase H (Roche Molecular Biochemicals, Germany) to 50 µg of phytase in a buffer containing 50 mM sodium phosphate, pH 6.5 and incubated at 37° C. overnight. After digestion, 1 µg of the protein was analyzed on a 12% Tris-Glycine Gel (Invitrogen, San Diego, Calif.). The results are summarized in FIG. 7 in table format.

The proteins were then analyzed by mass spectral analysis for maximum peptide mapping (FIG. 8A) and glycosylation mapping (FIG. 8B) (data not shown). For this experiment, all proteins need to be denatured, reduced and alkylated. Briefly, equal volume of 8 M urea (Sigma, MI) was added to phytase solution and incubated at 37° C. for 30 min. To reduce the protein, freshly made DTT (10 mg/mL) (Sigma, MI) was added to this mixture at a final concentration of 0.04 mg/mL followed by an incubation at 37° C. for 30 minutes. Next, 20 mg/mL of Iodoacetamide (Sigma, MI) was added to the reduced protein mixture at a final concentration of 20 µg/mL and incubated at 37° C. for 30 min for alkylation.

After the phytase protein was denatured, reduced and alkylated, the protein was then dialyzed into a buffer containing 34 mM NaCl and 0.08 N HCl. Pepsin (5–20 mg/mL) was added to digest phytase at 37° C. overnight. The complete digestion of the protein can be analyzed by SDS-PAGE.

Phytase fragments digested by pepsin were loaded on a Con A column (Pharmacia Biotech, Piscataway, N.J.) in a buffer containing 20 mM Tris, pH 7.4, 0.5 M NaCl, 1 mM $CaCl_2$, 1 mM $MnCl_2$, and 1 mM $MgCl_2$. The column was washed extensively with the same buffer. The glycosylated peptides were eluted using 20 mM Tris buffer pH 7.5 containing 0.5 M D-Methylmannoside.

For MALDI mass spectral analysis, two types of matrices were used in these experiments for either peptides or protein analysis. 3,5-Dimethoxy-4-hydroxycinnamic acid (10 mg/ml) dissolved in 49.9% water, 50% methanol, and 0.1% TFA was used for protein analysis. Alpha-Cyano-4-hydroxycinnamic acid (10 mg/ml) dissolved in 50% methanol, 49.9% ethanol and 0.1% TFA was used for peptide analysis. To apply on a steel probe tip, 1 µL of sample was mixed well with 1 µL of matrix solution. The samples mixed with matrix were air dried on the probe and analyzed on a Voyager-DE STR instrument (PE Biosystems, Foster City, Calif.).

Glycosylation sites for phytase from *S. cerevisiae* and *P. pastoris* are presented in FIGS. 9A and 9B. The results of these studies are summarized in FIG. 10.

EXAMPLE 4

Expression Host Comparisons

Figure 11:
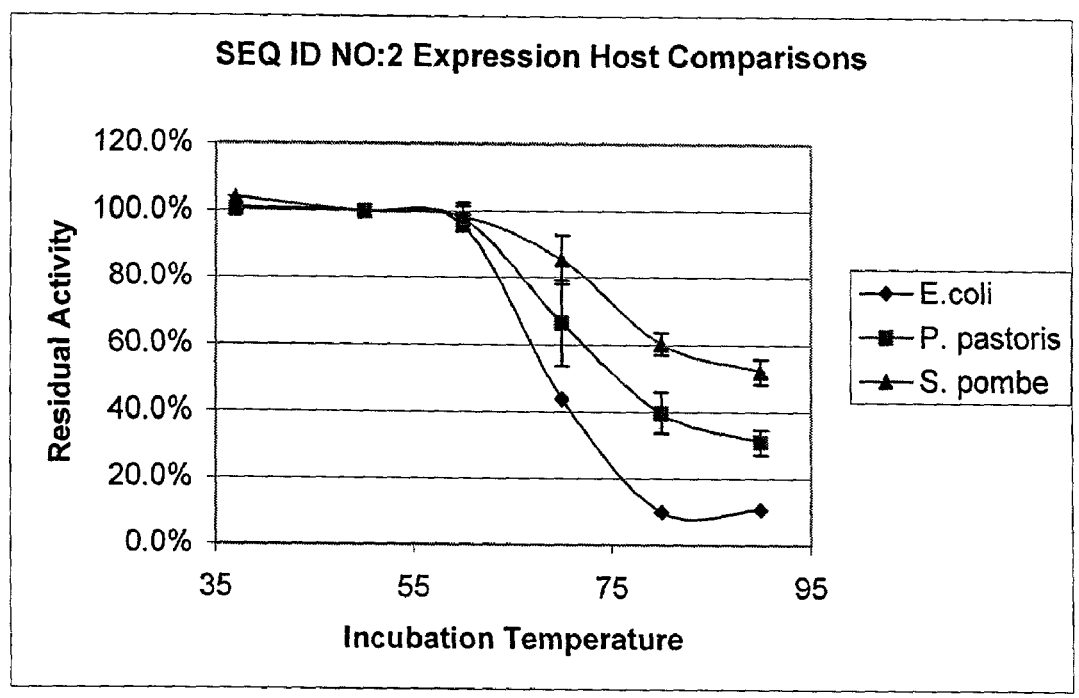
FIG. 11 shows a graph with results of a thermal tolerance assay for expression of modified phytase (SEQ ID NO:2) in various host cells.

The (GSSM™) DNA construct from SEQ ID NO:1 was inserted into *E. coli*, *P. pastoris*, and *S. pombe* for expression. The expressed proteins were purified to homogeneity. In the thermal tolerance assay, 100 uL of 0.01 mg/mL of protein in 100 mM MOPS, pH 7.0 was heated to the indicated incubation temperature as shown in FIG. 11 for 5 minutes in an RJ research thermocycler. Upon completion of the 5 minutes at the incubation temperature, the samples were cooled to 4° C. and incubated on ice. An activity assay was run using 40 uL of the enzyme solution in 1.46 mL of 100 mM NaOAc/4 mM phytate/pH 4.5 at 37° C. Aliquots of 60 uL were withdrawn at 2 minute intervals and added to 60 uL of the color developer/Stop solution of the TNO assay. (See FIG. 11).

EXAMPLE 5

Figure 12:
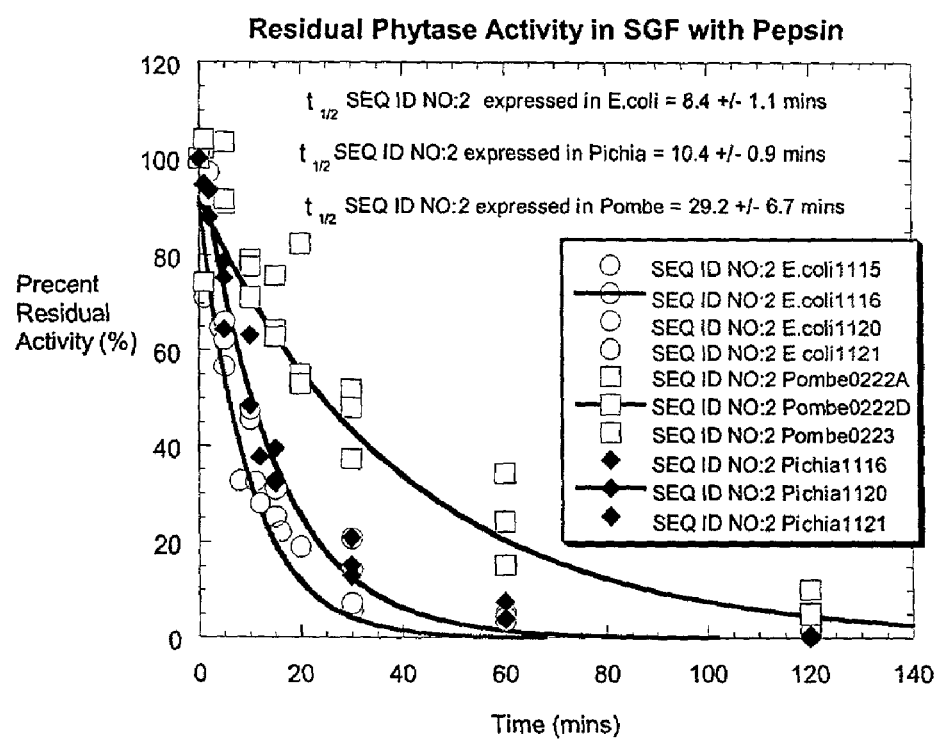
FIG. 12 is a graph showing residual activity of SEQ ID NO:2 phytase after exposure to in vitro digestibility assay using a simulated gastric intestinal fluid (SGF) with pepsin. The percent residual activities (based on initial rates) are shown for expression in E. coli (non-glycosylated), as well as P. pastoris and S. pombe (glycosylated).

The percent residual activities (based on initial rates) of the in vitro digested recombinant phytase (SEQ ID NO:2) expressed in *E. coli* (non-glycosylated), as well as in *S. pombe* and *P. pastoris* (glycosylated) were plotted verses time. A standard concentration of simulated gastric fluid containing 2 mg/ml NaCl, 6 M HCl and 3.2 mg/mL pepsin was prepared as described in the S.O.P. The pH of the solution was about 1.4 and was not adjusted. The in vitro digestibility assay was performed by adding 1:4 (vol:vol) of phytase to digestion solution and immediately incubating at 37° C. to initiate the digestion reaction. Aliquots of the digestion reaction mixture were removed at various time intervals and assayed for residual phytase activity using the TNO assay. Each of the assays was performed in triplicate. An exponential curve with the equation $y=Ae^{-kt}$ was fit to the data. The half lives of the proteins were determined using the equation $t_{1/2}=\ln 2/k$. The half-life of the non-glycosylated phytase of SEQ ID NO:2 expressed in *E. coli* was 8.4±1.1 minutes while the glycosylated phytase expressed in *S. pombe* had a half-life of 10.4±0.9 minutes and the same phytase expressed in *P. pastoris* had a half-life of 29.2±6.7 mins. Therefore, the glycosylation of the SEQ ID NO:2 phytase enhanced the stability of the enzyme under simulated in vitro digestibility conditions. (see FIG. 12)

EXAMPLE 5

To test the thermal tolerance of the invention the GSSM modified phytase (SEQ ID NO:2) when expressed in *E. coli*, *P. pastoris* and *S. pombe*, samples were heated to 37° C., 50° C., 60° C., 70° C. 80° C. and 90° C. for 5 minutes and then subjected to specific activity assay. The wild type K12 phytase (SEQ ID NO:3) expressed in *E. coli* was used as the control. The specific activity range at 37° C. as measured in units per milligram of enzyme was measured at pH 4.5 according to the TNO protocol described above. Table 3 below summarizes the results of the thermal tolerance/specific activity testing.

TABLE 3

Thermal Tolerance versus Specific Activity of
SEQ ID NO:2 phytase) expressed in E. coli and yeast Specific Activity Range at 37° C.
(Units per milligram protein)

| | | SEQ ID NO: 2 Phytase Expressed in | | |
|---|---|---|---|---|
| Temperature Range | Wild type K12 Phytase | E. coli | Pichia pastoris | Schizosaccharomyces pombe |
| 37° C.–50° C. | 1000–1200 | 1200 | 1200 | 1200 |
| 50° C.–70° C. | 0–1000 | 525–1200 | 750–1200 | 1000–1200 |
| 70° C.–90° C. | 0 | 100–500 | 350–750 | 610–1000 |

The results of these tests show that the glycosylated phytase enzymes obtained by expression in P. pastoris and S. pombe display superior tolerance to exposure to temperatures above 37° C. as compared to that of the wild type enzyme and further enhanced thermal tolerance as compared to the GSSM-modified, but non-glycosylated phytase. Moreover, expression of the enzyme in S. pombe conferred the greatest thermal tolerance, with retention of at least half (610-100 units per milligram protein) of the specific enzyme activity after exposure to temperatures from 70° C. to 90° C. By contrast, the wild type enzyme retained zero specific activity in this temperature range, and even the E. coli-expressed (non-glycosylated) GSSM modified phytase (SEQ ID NO:2) retained only 100–500 units of enzyme activity per milligram of enzyme after exposure to temperature in the range from 70° C. to 90° C. for 5 minutes. Therefore, the glycosylation of the phytase of SEQ ID NO:2 further enhanced the thermal tolerance and specific activity of the enzyme after exposure to elevated temperature.

LITERATURE CITED (The teachings of all references cited in this application were hereby incorporated by reference in their entirety unless otherwise indicated.)

Association of Official Analytical Chemists: Official Methods of Analysis. Association of Official Analytical Chemists, Washington, D.C., 1970.

Ausubel F M, et al. Current Protocols in Molecular Biology. Greene Publishing Assoc., Media, Pa. ©1987, ©1989, ©1992.

Barnes W M: PCR amplification of up to 35-kb DNA with high fidelity and high yield from lambda bacteriophage templates. *Proceedings of the National Academy of Sciences, USA* 91(6):2216–2220, 1994.

Bayer E A, Morag E, Lamed R: The cellulosome—a treasure-trove for biotechnology. *Trends Biotechnol* 12(9): 379–86, (September) 1994.

Bevan M: Binary *Agrobacterium* vectors for plant transformation. *Nucleic Acids Research* 12(22):8711–21, 1984.

Bird et al. *Plant Mol Biol* 11:651, 1988.

Blobel G, Walter P, Chang C N, Goldman B M, Erickson A H, Lingappa V R: Translocation of proteins across membranes: the signal hypothesis and beyond. *Symp Soc Exp Biol* 33:9–36, 1979.

Brederode F T, Koper-Zawrthoff E C, Bol J F: Complete nucleotide sequence of alfalfa mosaic virus RNA 4. *Nucleic Acids Research* 8(10):2213–23, 1980.

Clark W G, Register J C 3d, Nejidat A, Eichholtz D A, Sanders P R, Fraley R T, Beachy R N: Tissue-specific expression of the TMV coat protein in transgenic tobacco plants affects the level of coat protein-mediated virus protection. *Virology* 179(2):640–7, (December) 1990.

Cole, et al.: Monoclonal Antibodies and Cancer Therapy. A. R. Liss, New York. ©1985.

Coligan J E, et al.: Current Protocols in Immunology. J. Wiley and Sons, New York. ©1996.

Coruzzi G, Broglie R, Edwards C, Chua N H: Tissue-specific and light-regulated expression of a pea nuclear gene encoding the small subunit of ribulose-1,5-bisphosphalte carboxylase. *EMBO J* 3 (8):1671–9, 1984.

Cosgrove D J: Inositol phosphate phosphatases of microbiological origin. Inositol phosphate intermediates in the dephosphorylation of the hexaphosphates of myo-inositol, scyllo-inositol, and D-chiro-inositol by a bacterial (*Pseudomonas* sp.) phytase. *Aust J Biol Sci* 23(6):1207–1220, 1970.

Dassa E, Cahu M, Desjoyaux-Cherel B, Boquet P L: The acid phosphatase with optimum pH of 2.5 of *Escherichia coli*. Physiological and Biochemical study. *J Biol Chem* 257(12):6669–76, (Jun. 25) 1982.

Davis L G, et al. Basic Methods in Molecular Biology. Elsevier, N.Y., ©1986.

Duarte J C, Costa-Ferreira M: *Aspergilli* and lignocellulosics: enzymology and biotechnological applications. *FEMS Microbiol Rev* 13(2–3):377–86, (March) 1994.

Food Chemicals Codex, 4th Edition. Committee on Food Chemicals Codex, Food and Nutrition Board, Institute of Medicine, National Academy of Sciences. Published: National Academy Press, Washington, D.C., ©1996.

Garcia P D, Ghrayeb J, Inouye M, Walter P: Wild type and mutant signal peptides of *Escherichia coli* outer membrane lipoprotein interact with equal efficiency with mammalian signal recognition particle. *J Biol Chem* 262(20): 9463–8, (Jul. 15) 1987.

Gluzman Y: SV40-transformed simian cells support the replication of early SV40 mutants. *Cell* 23(1):175–182, 1981.

Goeddel D V, Shepard H M, Yelverton E, Leung D, Crea R, Sloma A, Pestka S: Synthesis of human fibroblast interferon by *E. coli*. *Nucleic Acids Research* 8(18):4057–4074, 1980.

Gordon-Kamm W J, Spencer T M, Mangano M L, Adams T R, Daines R J, Start W G, O'Brien J V, Chambers S A, Adams Jr. W R, Willets N G, Rice T B, Mackey C J, Krueger R W, Kausch A P, Lemaux P G. *Plant Cell* 2:603, 1990.

Graf E: Phytic Acid: Chemistry and Applications. Pilatus Press, Minneapolis. 1986.

Greiner R, Haller E, Konietzny U, Jany K D: Purification and characterization of a phytase from *Klebsiella terrigena*. *Arch Biochem Biophys* 341(2):201–6, (May 15) 1997.

Greiner R, Konietzny U: Construction of a bioreactor to produce special breakdown products of phytate. *J Biotechnol* 48(1–2):153–9, (Jul. 18) 1996.

Greiner R, Konietzny U, Jany K D: Purification and characterization of two phytases from *Escherichia coli*. *Arch Biochem Biophys* 303(1):107–13, (May 15) 1993.

Guilley H, Dudley R K, Jonard G, Balazs E, Richards K E: Transcription of Cauliflower mosaic virus DNA: detection of promoter sequences, and characterization of transcripts. *Cell* 30(3):763–73, 1982.

Hespell R B, Whitehead T R: Physiology and genetics of xylan degradation by gastrointestinal tract bacteria. *J Dairy Sci* 73(10):3013–22, (October) 1990.

Hoekema A, Hirsch P R, Hooykaas P J J, Schilperoort R A. *Nature* 303:179, 1983.

Horsch R B, Fry J E, Hoffmann N L, Eichholtz D, Rogers S G, Fraley R T. *Science* 227:1229, 1985.

Igarashi M, Hollander V P: Acid phosphatase from rat liver. Purification, crystallization, and properties. *J Biol Chem* 243(23):6084–9, (Dec. 10) 1968.

International Union of Biochemistry and Molecular Biology, Nomenclature Committee: Enzyme nomenclature 1992: recommendations of the Nomenclature Committee of the International Union of Biochemistry and Molecular Biology on the nomenclature and classification of enzymes/ prepared for NC-IUBMB by Edwin C. Webb. Academic Press, c1992.

Jeffries T W: Biochemistry and genetics of microbial xylanases. *Curr Opin Biotechnol* 7(3):337–42, (June) 1996.

Jermutus L, Tessier M, Pasamontes L, van Loon APGM, Lehmann M: Structure-based chimeric enzymes as an alternative to directed enzyme evolution: phytase as a test case. J. Biotechnology 85:15–24, 2001.

Klee H J, Muskopf Y M, Gasser C S: Cloning of an *Arabidopsis thaliana* gene encoding 5-enolpyruvylshikimate-3-phosphate synthase: sequence analysis and manipulation to obtain glyphosate-tolerant plants. *Mol Gen Genet* 210(3):437–42, (December) 1987.

Kohler G, Milstein C: Continuous cultures of fused cells secreting antibody of predefined specificity. *Nature* 256 (5517):495–497, 1975.

Koster-Topfer M, Frommer W B, Rocha-Sosa M, Rosahl S, Schell J, Willmitzer L: A class II patatin promoter is under developmental control in both transgenic potato and tobacco plants. *Mol Gen Genet* 219(3):390–6, (November) 1989.

Kozbor. *Immunology Today* 4:72, 1983.

Lee B, et al.: Transient gene expression in aleurone protoplasts isolated from developing caryopses of barley and wheat. *Plant Mol Biol* 13(1):21–9, 1989.

Lehmann M, Lopez-Ulibarri R, Loch C, Viarouge C, Wyss M and van Loon, APGM. *Protein Science* 9:1866–1872, 2000.

National Research Council: Nutrient Requirements of Poultry (9th Revised ed.). National Academy Press, Washington, D.C., 1994.

Nayini N R, et al.: *Lebensmittel Wissenschaft und Technologie* 17:24–26, 1984.

NCBI, National Library of Medicine. National Institutes of Health: BLAST Sequence Similarity Searching (web site=website address ncbi.nlm.nih.gov).

Nelson T S, Shieh T R, Wodzinski R J, Wwere J H: Effect of supplemental rhytase on the utilization of phytate phosphorus by chicks. *J Nutr* 101(10):1289–1293, 1971.

Ng D T, Walter P: Protein translocation across the endoplasmic reticulum. *Curr Opin Cell Biol* 6(4):510–6, (August), 1994.

Potrykus I: Gene transfer methods for plants and cell cultures. *Ciba Found Symp* 154:198–208; discussion 208–12, 1990.

Powar V K, et al.: Purification and properties of phytate-specific phosphatase from *Bacillus subtilis*. *J Bacteriol* 151(3):1102–1108, 1982.

Powers T, et al.: The nascent polypeptide-associated complex modulates interactions between the signal recognition particle and the ribosome. *Curr Biol* 6(3):331–8, (Mar. 1), 1996.

Prade R A: Xylanases: from biology to biotechnology. *Biotechnol Genet Eng Rev;* 13:101–31, 1996.

Ryan A J, et al.: Genomic sequence of a 12S seed storage protein from oilseed rape (*Brassica napus* c.v. *jet neuf*). *Nucl Acids Res* 17(9):3584, 1989.

Saiki R K, Gelfand D H, Stoffel S, Scharf S J, Higuchi R, Horn G T, Mullis K B, Erlich H A: Primer-directed enzymatic amplification of DNA with a thermostable DNA polymerase. *Science* 239(4839):487–491, 1988.

Sambrook J, Fritsch E F, Maniatis T: Molecular Cloning: A Laboratory Manual, Cold Spring Habor Press, Cold Spring Habor, N.Y., ©1989.

SAS: Statistics In: SAS User's Guide (1984 ed.). SAS Institute, Cwerey, N.C., 1984.

Schoner F J, Hope P P, Schwarz G, Wiesche H: Comparative effects of microbial phytase and inorganic phosphorus on performance and retention of phosphorus, calcium, and crude ash in broilers. *J Anim Physiol Anim Nutr* 66:248, 1991.

Schoner F J, Hope P P, Schwarz G, Wiesche H: Effects of microbial phytase and inorganic phosphate in broiler chicken: Performance and mineral retention at various calcium levels. *J Anim Physiol Anim Nutr* 69:235, 1993.

Shieh T R, et al.: Regulation of the formation of acid phosphatases by inorganic phosphate in *Aspergillus ficuum*. *J Bacteriol* 100(3):1161–5, (December) 1969.

Shimamoto K, Miyazaki C, Hashimoto H, Izawa T, Itoh K, Terada R, Inagaki Y, Iida S: Trans-activation and stable integration of the maize transposable element Ds cotransfected with the Ac transposase gene in transgenic rice plants. *Mol Gen Genet* 239(3):354–60, (June) 1993.

Shimizu M: Bioscience, Biotechnology, and Biochemistry 56:1266–1269, 1992.

Sijmons P C, Dekker B M, Schrammeijer B, Verwoerd T C, van den Elzen P J, Hoekema A: Production of correctly processed human serum albumin in transgenic plants. *Biotechnology (N Y)* 8(3):217–21, 1990.

Simons P C, Versteegh H A, Jongbloed A W, Kemme P A, Slump P, Bos K D), Wolters M G, Beudeker R F, Verschoor G J: Improvement of phosphorus availability by microbial phytase in broilers and pigs. *Br J Nutr* 64(2):525–540, 1990.

Smeekens S, Weisbeek P, Robinson C: Protein transport into and within chloroplasts. *Trends Biochem Sci* 15(2):73–6, 1990.

Smith A G, et al.: Identification and characterization of stamen- and tapetun-specific genes from tomato. *Mol Gen Genet* 222(1):9–16, (June)1990.

Tague B W, et al.: A short domain of the plant vacuolar protein phytohemagglutinin targets invertase to the yeast vacuole. *Plant Cell* 2(6):533–46, (June) 1990.

Tingey S V, et al.: Glutamine synthetase genes of pea encode distinct polypeptides which were differentially expressed in leaves, roots and nodules. *EMBO J* 6(1):1–9, 1987.

Tomschy A, et al. Optimization of the catalytic properties of *Aspergillus Fumigatus* phytase based on the three-dimensional structure. *Protein Science* 9:1304–1311, 2000.

Ullah A H: Production, rapid purification and catalytic characterization of extracellular phytase from *Aspergillus ficuum*. *Prep Biochem* 18(4):443–458, 1988.

Ullah A H, Gibson D M: Extracellular phytase (E.C. 3.1.3.8) from *Aspergillus ficuum* NRRL 3135: purification and characterization. *Prep Biochem* 17(1):63–91, 1987

Van den Broeck G, et al.: Targeting of a foreign protein to chloroplasts by fusion to the transit peptide from the small subunit of ribulose 1,5-bisphosphate carboxylase. *Nature* 313(6001):358–63, 1985.

Vasil I K, Vasil V: Totipotency and embryogenesis in plant cell and tissue cultures. *In Vitro* 8(3):117–27, (November–December) 1972.

Vasil V, Vasil I K: Regeneration of tobacco and petunia plants from protoplasts and culture of corn protoplasts. *In Vitro* 10:83–96, (July–August) 1974.

Von Heijne G: Towards a comparative anatomy of N-terminal topogenic protein sequences. *J Mol Biol* 189(1): 239–42, 1986.

*Walter P, Blobel G. *Biochem Soc Symp* 47:183, 1986.

Wenzler H, et al.: Sucrose-regulated expression of a chimeric potato tuber gene in leaves of transgenic tobacco plants. *Plant Mol Biol* 13(4):347–54, 1989.

Wolter F P, et al. rbcS genes in *Solanum tuberosum*: conservation of transit peptide and exon shuffling during evolution. *Proc Natl Acad Sci USA* 85(3):846–50, (February) 1988.

Wong K K, et al.: Multiplicity of beta-1,4-xylanase in microorganisms: functions and applications. *Microbiol Rev* 52(3):305–17, (September) 1988.

Wyss M, et al. Biochemical Characterization of Fungal Phytases (myo-inositol Hexakisphosphate Phosphohydrolases): Catalytic Properties. *Applied and Environmental Microbiology* February 1999: 367–373.

Yamada K, et al.: Agricultural and Biological Chemistry 32:1275–1282, 1968.

U.S. Pat. No. 3,297,548; Filed Jul. 28, 1964; Issued Jan. 10, 1967. Wwere J H, Bluff L, Shieh T K: Preparation of acid phytase.

U.S. Pat. No. 4,946,778; Filed Jan. 19, 1989; Issued Aug. 7, 1990. Ladner R C, Bird R E, Hardman K: Single polypeptide chain binding molecules.

U.S. Pat. No. 5,830,732, Filed Jul. 3, 1995, Issued Nov. 3, 1998. Mochizuki D, Tokuda J, Shimada M and Tawaki S. Phytase.

EPO 120,516; Filed Feb. 21, 1984; Issued Oct. 3, 1984. Schilperoort R A, et al.: A process of the incorporation of foreign DNA into the genome of dicotyledonous plants; *Agrobacterium tumefaciens* bacteria and a process for the production thereof; plants and plant cells with modified genetic properties; a process for the preparation.

EPO 321,004; Filed Oct. 28, 1988; Issued Jan. 22, 1992. Vaara T, et al., A process for steeping cereals with a new enzyme preparation.

IPN WO 91/05053; Filed Sep. 27, 1990; Issued Apr. 18, 1991. VanGorcom R, et al.: Cloning and expression of microbial phytase.

Plant Cell Culture Protocols (Methods in Molecular Biology (Cloth), 111) by Robert D. Hall (Editor) (March 1999) Humana Press; ISBN: 0896035492

Plant Molecular Biology: Essential Techniques by P. Jones (Editor), J. M. Sutton (Editor), Mark Sutton (Contributor) (Sep. 25, 1997) John Wiley & Son Ltd; ISBN: 0471972681

Plant Biochemistry and Molecular Biology by Hans-Walter Heldt (April 1998) Oxford University Press; ISBN: 019850179X Biochemistry and Molecular Biology of Plants by Bob B. Buchanan (Editor), Wilhelm Gruissem (Editor), Russell L. Jones (July 2000) Amer Society of Plant; ISBN: 0943088372

Monoclonal Antibodies: A Manual of Techniques by Heddy Zola (September 1987) CRC Press; ISBN: 0849364760

Immunochemistry in Practice by Robin Thorpe (Contributor), Alan P. Johnstone 3rd ed (Jan. 15, 1996) Blackwell Science Inc; ISBN: 0865426333

What is claimed is:

1. An isolated or recombinant polypeptide comprising (a) a polypeptide having a phytase activity and an amino acid sequence having at least 98.5% sequence identity to a sequence as set forth in SEQ ID NO:2, or (b) a polypeptide having a phytase activity encoded by a nucleic acid comprising a sequence having at least 98.5% sequence identity to SEQ ID NO:1.

2. The isolated or recombinant polypeptide of claim 1, wherein the phytase is thermotolerant.

3. The isolated or recombinant polypeptide of claim 1, wherein the phytase is thermostable.

4. The isolated or recombinant polypeptide of claim 1, wherein the nucleic acid encoding the polypeptide has at least 99% sequence identity to SEQ ID NO:1.

5. The isolated or recombinant polypeptide of claim 4, wherein the nucleic acid encoding the polypeptide has at least 99.5% sequence identity to SEQ ID NO:1.

6. The isolated or recombinant polypeptide of claim 1, wherein the amino acid sequence has a sequence as set forth in SEQ ID NO:2.

7. An isolated or recombinant polypeptide, wherein the polypeptide has a phytase activity, lacks a signal sequence, and comprises (a) a polypeptide having a phytase activity and an amino acid sequence having at least 98.5% sequence identity to a sequence as set forth in SEQ ID NO:2, or (b) a polypeptide having a phytase activity encoded by a nucleic acid comprising a sequence having at least 98.5% sequence identity to SEQ ID NO:1.

8. The isolated or recombinant polypeptide of claim 3, wherein the phytase activity is thermostable when heated to a temperature in the range from about 37° C. to about 50° C., about 50° C. to about 70° C. or about 70° C. to about 90° C.

9. The isolated or recombinant polypeptide of claim 8, wherein the phytase has a specific activity at about 37° C. in the range from about 100 to about 1000 units per milligram of protein.

10. The isolated or recombinant polypeptide of claim 9, wherein the phytase has a specific activity from about 500 to about 750 units per milligram of protein.

11. The isolated or recombinant polypeptide of claim 3, wherein the phytase has a specific activity at 37° C. in the range from about 500 to about 1200 units per milligram of protein.

12. The isolated or recombinant polypeptide of claim 11, wherein the phytase has a specific activity at 37° C. in the range from about 750 to about 1000 units per milligram of protein.

13. The isolated or recombinant polypeptide of claim 2, wherein the phytase is thermotolerant after being heated to an elevated temperature in the range from about 37° C. to about 90° C.

14. The isolated or recombinant polypeptide of claim 13, wherein the phytase is thermotolerant after being heated to a temperature in the range from about 37° C. to about 70° C.

15. The isolated or recombinant polypeptide of claim 13, wherein the phytase retains at least half of its specific activity at 37° C. after being heated to the elevated temperature.

16. The isolated or recombinant polypeptide of claim 13, wherein the phytase retains specific activity at 37° C. in the range from about 500 to about 1200 units per milligram of protein after being heated to the elevated temperature.

17. The isolated or recombinant polypeptide of claim 1, wherein the polypeptide comprises at least one glycosylation site.

18. The isolated or recombinant polypeptide of claim 17, wherein the at least one glycosylation site is an N-linked glycosylation site.

19. The isolated or recombinant polypeptide of claim 1, wherein phytase is glycosylated after being expressed in *P. pastoris* or *S. pombe*.

20. The isolated or recombinant polypeptide of claim 1, wherein the polypeptide retains a phytase activity at a pH of about pH 5.

21. The isolated or recombinant polypeptide of claim 1, wherein the polypeptide retains a phytase activity at a pH of about pH 4.5.

22. A protein preparation comprising a polypeptide as set forth in claim 1, wherein the protein preparation comprises a liquid, a solid or a gel.

23. A heterodimer or fusion protein comprising a polypeptide as set forth in claim 1 and a heterologous polypeptide.

24. The heterodimer or fusion protein of claim 23, wherein the heterologous polypeptide comprises an epitope.

25. The heterodimer or fusion protein of claim 23, wherein the heterologous polypeptide comprises a tag.

26. An immobilized polypeptide having a phytase activity, wherein the immobilized polypeptide comprises a polypeptide having a sequence as set forth in claim 1 or a heterodimer or fusion protein as set forth in claim 23.

27. The immobilized polypeptide of claim 26, wherein the phytase is immobilized on a cell, a metal, a resin, a polymer, a ceramic, a glass, a microelectrode, a graphitic particle, a bead, a gel, a plate, an array or a capillary tube.

28. An array comprising an immobilized polypeptide as set forth in claim 1 or claim 23.

29. A food supplement for an animal comprising a polypeptide as set forth in claim 1 having a phytase activity.

30. The food supplement of claim 29, wherein the polypeptide is glycosylated.

31. An enzyme delivery matrix comprising a polypeptide as set forth in claim 1 having a phytase activity.

32. The enzyme delivery matrix of claim 31, wherein the delivery matrix is in the form of a pellet, a pill, a tablet, a liquid, a gel, a capsule, a syrup, an emulsion, a lozenge, a dressing or a liposome.

33. The enzyme delivery matrix of claim 31, wherein the polypeptide is glycosylated.

34. The enzyme delivery matrix of claim 31, wherein the phytase is thermotolerant.

35. The enzyme delivery matrix of claim 31, wherein the phytase is thermostable.

36. An edible pellet comprising a granulate edible carrier and a polypeptide having phytase activity comprising a polypeptide as set forth in claim 1.

37. A feed composition comprising a polypeptide having a sequence as set forth in claim 1, and an edible carrier.

38. The feed composition of claim 37, wherein the phytase protein is a recombinant phytase protein.

39. The feed composition of claim 38, wherein the phytase protein is glycosylated.

40. The feed composition of claim 39 wherein the phytase protein is thermotolerant or thermostable.

41. The feed composition of claim 38, wherein the feed composition is manufactured in pellet, pill or tablet form.

42. The feed composition of claim 38, wherein the feed composition is produced using polymer coated additives.

43. The feed composition of claim 38, wherein the feed composition is manufactured in granulate form.

44. The feed composition of claim 38, wherein the feed composition is produced by spray drying.

45. An organic meal comprising a polypeptide as set forth in claim 1 having a phytase activity.

46. An isolated or recombinant polypeptide comprising (a) a polypeptide having an enzymatic activity and an amino acid sequence having at least 98.5% sequence identity to a sequence as set forth in SEQ ID NO:2, or (b) a polypeptide having an enzymatic activity and encoded by a nucleic acid comprising a sequence having at least 98.5% sequence identity to SEQ ID NO:1, wherein said enzymatic activity comprises catalyzing the hydrolysis of phytate (myo-inositol-hexaphosphate), or the reverse reaction.

47. The isolated or recombinant polypeptide of claim 46, wherein the sequence identity to the polypeptide of SEQ ID NO:2 is at least 99%.

48. The isolated or recombinant polypeptide of claim 47, wherein the sequence identity to the polypeptide of SEQ ID NO:2 is at least 99.5%.

49. The enzyme delivery matrix of claim 31, wherein the enzyme delivery matrix is an edible enzyme delivery matrix.

50. The isolated or recombinant polypeptide of claim 46, wherein the sequence identity to the nucleic acid of SEQ ID NO:1 is at least 99%.

51. The isolated or recombinant polypeptide of claim 50, wherein the sequence identity to the nucleic acid of SEQ ID NO:1 is at least 99.5%.

52. The organic meal of claim 45, wherein the organic meal comprises corn, soybean or a corn and soybean meal mix.

53. The isolated or recombinant polypeptide of claim 1, wherein the sequence identity to the polypeptide of SEQ ID NO:2 is at least 99%.

54. The isolated or recombinant polypeptide of claim 53, wherein the sequence identity to the polypeptide of SEQ ID NO:2 is at least 99.5%.

* * * * *

UNITED STATES PATENT AND TRADEMARK OFFICE
CERTIFICATE OF CORRECTION

| | |
|---|---|
| PATENT NO. | : 7,078,035 B2 |
| APPLICATION NO. | : 10/156660 |
| DATED | : July 18, 2006 |
| INVENTOR(S) | : Short et al. |

Page 1 of 1

It is certified that error appears in the above-identified patent and that said Letters Patent is hereby corrected as shown below:

Title page, item (75) Inventors:

"Jay M. Short, Del Mar, CA (US); Kevin A. Gray, San Diego, CA (US); Nelson R. Barton, San Diego, CA (US); James B. Garrett, San Diego, CA (US); Eileen O'Donoghue, San Diego, CA (US)"

should be changed to

--Jay M. Short, Del Mar, CA (US); Kevin A. Gray, San Diego, CA (US); Nelson R. Barton, San Diego, CA (US); James B. Garrett, San Diego, CA (US); Eileen O'Donoghue, San Diego, CA (US); Dan E. Robertson, Belmont, MA (US)--

Signed and Sealed this

Fourteenth Day of October, 2008

JON W. DUDAS
*Director of the United States Patent and Trademark Office*

UNITED STATES PATENT AND TRADEMARK OFFICE
Certificate

Patent No. 7,078,035 B2                        Patented: July 18, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jay M. Short, Del Mar, CA (US); Kevin A. Gray, San Diego, CA (US); Nelson R. Barton, San Diego, CA (US); James B. Garrett, San Diego, CA (US); Eileen O'Donoghue, San Diego, CA (US); and Dan E. Robertson, Belmont, MA (US).

Signed and Sealed this Twenty-eighth Day of October 2008.

*NASHAAT T. NASHED, Ph. D*
*Supervisory Patent Examiner*
*Art Unit 1652*

SEQUENCE LISTING

```
<160> NUMBER OF SEQ ID NOS: 4

<210> SEQ ID NO 1
<211> LENGTH: 1308
<212> TYPE: DNA
<213> ORGANISM: Artificial Sequence
<220> FEATURE:
<223> OTHER INFORMATION: modified phytase enzyme
<220> FEATURE:
<221> NAME/KEY: CDS
<222> LOCATION: (1)...(1308)

<400> SEQUENCE: 1 atg aaa gcg atc tta atc cca ttt tta tct ctt ctg att ccg tta acc      48
Met Lys Ala Ile Leu Ile Pro Phe Leu Ser Leu Leu Ile Pro Leu Thr
1               5                   10                  15 ccg caa tct gca ttc gct cag agt gag ccg gag ctg aag ctg gaa agt      96
Pro Gln Ser Ala Phe Ala Gln Ser Glu Pro Glu Leu Lys Leu Glu Ser
            20                  25                  30 gtg gtg att gtc agt cgt cat ggt gtg cgt gct cca acc aag gcc acg     144
Val Val Ile Val Ser Arg His Gly Val Arg Ala Pro Thr Lys Ala Thr
        35                  40                  45 caa ctg atg cag gat gtc acc cca gac gca tgg cca acc tgg ccg gta     192
Gln Leu Met Gln Asp Val Thr Pro Asp Ala Trp Pro Thr Trp Pro Val
    50                  55                  60 aaa ctg ggt gag ctg aca ccg cgc ggt ggt gag cta atc gcc tat ctc     240
Lys Leu Gly Glu Leu Thr Pro Arg Gly Gly Glu Leu Ile Ala Tyr Leu
65                  70                  75                  80 gga cat tac tgg cgt cag cgt ctg gta gcc gac gga ttg ctg cct aaa     288
```

-continued

```
                Gly His Tyr Trp Arg Gln Arg Leu Val Ala Asp Gly Leu Leu Pro Lys
                             85                  90                  95 tgt ggc tgc ccg cag tct ggt cag gtc gcg att att gct gat gtc gac        336
Cys Gly Cys Pro Gln Ser Gly Gln Val Ala Ile Ile Ala Asp Val Asp
                100                 105                 110 gag cgt acc cgt aaa aca ggc gaa gcc ttc gcc gcc ggg ctg gca cct        384
Glu Arg Thr Arg Lys Thr Gly Glu Ala Phe Ala Ala Gly Leu Ala Pro
            115                 120                 125 gac tgt gca ata acc gta cat acc cag gca gat acg tcc agt ccc gat        432
Asp Cys Ala Ile Thr Val His Thr Gln Ala Asp Thr Ser Ser Pro Asp
        130                 135                 140 ccg tta ttt aat cct cta aaa act ggc gtt tgc caa ctg gat aac gcg        480
Pro Leu Phe Asn Pro Leu Lys Thr Gly Val Cys Gln Leu Asp Asn Ala
145                 150                 155                 160 aac gtg act gac gcg atc ctc gag agg gca gga ggg tca att gct gac        528
Asn Val Thr Asp Ala Ile Leu Glu Arg Ala Gly Gly Ser Ile Ala Asp
                165                 170                 175 ttt acc ggg cat tat caa acg gcg ttt cgc gaa ctg gaa cgg gtg ctt        576
Phe Thr Gly His Tyr Gln Thr Ala Phe Arg Glu Leu Glu Arg Val Leu
            180                 185                 190 aat ttt ccg caa tca aac ttg tgc ctt aaa cgt gag aaa cag gac gaa        624
Asn Phe Pro Gln Ser Asn Leu Cys Leu Lys Arg Glu Lys Gln Asp Glu
        195                 200                 205 agc tgt tca tta acg cag gca tta cca tcg gaa ctc aag gtg agc gcc        672
Ser Cys Ser Leu Thr Gln Ala Leu Pro Ser Glu Leu Lys Val Ser Ala
    210                 215                 220 gac tgt gtc tca tta acc ggt gcg gta agc ctc gca tca atg ctg acg        720
Asp Cys Val Ser Leu Thr Gly Ala Val Ser Leu Ala Ser Met Leu Thr
225                 230                 235                 240 gag ata ttt ctc ctg caa caa gca cag gga atg ccg gag ccg ggg tgg        768
Glu Ile Phe Leu Leu Gln Gln Ala Gln Gly Met Pro Glu Pro Gly Trp
                245                 250                 255 gga agg atc acc gat tca cac cag tgg aac acc ttg cta agt ttg cat        816
Gly Arg Ile Thr Asp Ser His Gln Trp Asn Thr Leu Leu Ser Leu His
            260                 265                 270 aac gcg caa ttt gat ttg cta caa cgc acg cca gag gtt gcc cgc agc        864
Asn Ala Gln Phe Asp Leu Leu Gln Arg Thr Pro Glu Val Ala Arg Ser
        275                 280                 285 cgc gcc acc ccg tta tta gat ttg atc aag aca gcg ttg acg ccc cat        912
Arg Ala Thr Pro Leu Leu Asp Leu Ile Lys Thr Ala Leu Thr Pro His
    290                 295                 300 cca ccg caa aaa cag gcg tat ggt gtg aca tta ccc act tca gtg ctg        960
Pro Pro Gln Lys Gln Ala Tyr Gly Val Thr Leu Pro Thr Ser Val Leu
305                 310                 315                 320 ttt atc gcc gga cac gat act aat ctg gca aat ctc ggc ggc gca ctg       1008
Phe Ile Ala Gly His Asp Thr Asn Leu Ala Asn Leu Gly Gly Ala Leu
                325                 330                 335 gag ctc aac tgg acg ctt ccc ggt cag ccg gat aac acg ccg cca ggt       1056
Glu Leu Asn Trp Thr Leu Pro Gly Gln Pro Asp Asn Thr Pro Pro Gly
            340                 345                 350 ggt gaa ctg gtg ttt gaa cgc tgg cgt cgg cta agc gat aac agc cag       1104
Gly Glu Leu Val Phe Glu Arg Trp Arg Arg Leu Ser Asp Asn Ser Gln
        355                 360                 365 tgg att cag gtt tcg ctg gtc ttc cag act tta cag cag atg cgt gat       1152
Trp Ile Gln Val Ser Leu Val Phe Gln Thr Leu Gln Gln Met Arg Asp
    370                 375                 380 aaa acg ccg ctg tca tta aat acg ccg ccc gga gag gtg aaa ctg acc       1200
Lys Thr Pro Leu Ser Leu Asn Thr Pro Pro Gly Glu Val Lys Leu Thr
385                 390                 395                 400
```

-continued

```
ctg gca gga tgt gaa gag cga aat gcg cag ggc atg tgt tcg ttg gca      1248
Leu Ala Gly Cys Glu Glu Arg Asn Ala Gln Gly Met Cys Ser Leu Ala
            405                 410                 415 ggt ttt acg caa atc gtg aat gaa gca cgc ata ccg gcg tgc agt ttg      1296
Gly Phe Thr Gln Ile Val Asn Glu Ala Arg Ile Pro Ala Cys Ser Leu
        420                 425                 430 aga tct cat cta                                                       1308
Arg Ser His Leu
        435
```

<210> SEQ ID NO 2
<211> LENGTH: 436
<212> TYPE: PRT
<213> ORGANISM: Artificial Sequence
<220> FEATURE:
<223> OTHER INFORMATION: modified phytase enzyme

<400> SEQUENCE: 2

```
Met Lys Ala Ile Leu Ile Pro Phe Leu Ser Leu Leu Ile Pro Leu Thr
 1               5                  10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Glu Leu Thr Pro Arg Gly Gly Glu Leu Ile Ala Tyr Leu
65                  70                  75                  80

Gly His Tyr Trp Arg Gln Arg Leu Val Ala Asp Gly Leu Leu Pro Lys
                85                  90                  95

Cys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Glu Arg Ala Gly Gly Ser Ile Ala Asp
                165                 170                 175

Phe Thr Gly His Tyr Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Cys Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Asp Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300
```

```
Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
    370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430

Arg Ser His Leu
        435

<210> SEQ ID NO 3
<211> LENGTH: 1901
<212> TYPE: DNA
<213> ORGANISM: Escherichia coli
<220> FEATURE:
<221> NAME/KEY: CDS
<222> LOCATION: (188)...(1483)
<220> FEATURE:
<221> NAME/KEY: misc_feature
<222> LOCATION: 403
<223> OTHER INFORMATION: n = A,T,C or G

<400> SEQUENCE: 3
taaggagcag aaacaatgtg gtatttactt tggttcgtcg gcattttgtt gatgtgttcg      60
ctctccaccc ttgtgttggt atggctggac ccgcgtctga aaagttaacg aacgtaggcc     120
tgatgcggcg cattagcatc gcatcaggca atcaataatg tcagatatga aaagcggaaa     180 catatcg atg aaa gcg atc tta atc cca ttt tta tct ctt ctg att ccg       229
        Met Lys Ala Ile Leu Ile Pro Phe Leu Ser Leu Leu Ile Pro
          1               5                  10 tta acc ccg caa tct gca ttc gct cag agt gag ccg gag ctg aag ctg       277
Leu Thr Pro Gln Ser Ala Phe Ala Gln Ser Glu Pro Glu Leu Lys Leu
 15              20                  25                  30 gaa agt gtg gtg att gtc agt cgt cat ggt gtg cgt gct cca acc aag       325
Glu Ser Val Val Ile Val Ser Arg His Gly Val Arg Ala Pro Thr Lys
                 35                  40                  45 gcc acg caa ctg atg cag gat gtc acc cca gac gca tgg cca acc tgg       373
Ala Thr Gln Leu Met Gln Asp Val Thr Pro Asp Ala Trp Pro Thr Trp
             50                  55                  60 ccg gta aaa ctg ggt tgg ctg aca ccg cgn ggt ggt gag cta atc gcc       421
Pro Val Lys Leu Gly Trp Leu Thr Pro Arg Gly Gly Glu Leu Ile Ala
         65                  70                  75 tat ctc gga cat tac caa cgc cag cgt ctg gta gcc gac gga ttg ctg       469
Tyr Leu Gly His Tyr Gln Arg Gln Arg Leu Val Ala Asp Gly Leu Leu
     80                  85                  90 gcg aaa aag ggc tgc ccg cag tct ggt cag gtc gcg att att gct gat       517
Ala Lys Lys Gly Cys Pro Gln Ser Gly Gln Val Ala Ile Ile Ala Asp
 95                 100                 105                 110 gtc gac gag cgt acc cgt aaa aca ggc gaa gcc ttc gcc gcg ggg ctg       565
Val Asp Glu Arg Thr Arg Lys Thr Gly Glu Ala Phe Ala Ala Gly Leu
                115                 120                 125
```

-continued

| | | |
|---|---|---|
| gca cct gac tgt gca ata acc gta cat acc cag gca gat acg tcc agt<br>Ala Pro Asp Cys Ala Ile Thr Val His Thr Gln Ala Asp Thr Ser Ser<br>130                                   135                             140 | | 613 |
| ccc gat ccg tta ttt aat cct cta aaa act ggc gtt tgc caa ctg gat<br>Pro Asp Pro Leu Phe Asn Pro Leu Lys Thr Gly Val Cys Gln Leu Asp<br>       145                              150                          155 | | 661 |
| aac gcg aac gtg act gac gcg atc ctc agc agg gca gga ggg tca att<br>Asn Ala Asn Val Thr Asp Ala Ile Leu Ser Arg Ala Gly Gly Ser Ile<br>160                                 165                           170 | | 709 |
| gct gac ttt acc ggg cat cgg caa acg gcg ttt cgc gaa ctg gaa cgg<br>Ala Asp Phe Thr Gly His Arg Gln Thr Ala Phe Arg Glu Leu Glu Arg<br>175                                 180                           185                     190 | | 757 |
| gtg ctt aat ttt ccg caa tca aac ttg tgc ctt aaa cgt gag aaa cag<br>Val Leu Asn Phe Pro Gln Ser Asn Leu Cys Leu Lys Arg Glu Lys Gln<br>                   195                           200                          205 | | 805 |
| gac gaa agc tgt tca tta acg cag gca tta cca tcg gaa ctc aag gtg<br>Asp Glu Ser Cys Ser Leu Thr Gln Ala Leu Pro Ser Glu Leu Lys Val<br>               210                           215                          220 | | 853 |
| agc gcc gac aat gtc tca tta acc ggt gcg gta agc ctc gca tca atg<br>Ser Ala Asp Asn Val Ser Leu Thr Gly Ala Val Ser Leu Ala Ser Met<br>           225                           230                           235 | | 901 |
| ctg acg gag ata ttt ctc ctg caa caa gca cag gga atg ccg gag ccg<br>Leu Thr Glu Ile Phe Leu Leu Gln Gln Ala Gln Gly Met Pro Glu Pro<br>240                                 245                           250 | | 949 |
| ggg tgg gga agg atc acc gat tca cac cag tgg aac acc ttg cta agt<br>Gly Trp Gly Arg Ile Thr Asp Ser His Gln Trp Asn Thr Leu Leu Ser<br>255                                 260                           265                     270 | | 997 |
| ttg cat aac gcg caa ttt tat ttg cta caa cgc acg cca gag gtt gcc<br>Leu His Asn Ala Gln Phe Tyr Leu Leu Gln Arg Thr Pro Glu Val Ala<br>                   275                           280                          285 | | 1045 |
| cgc agc cgc gcc acc ccg tta tta gat ttg atc aag aca gcg ttg acg<br>Arg Ser Arg Ala Thr Pro Leu Leu Asp Leu Ile Lys Thr Ala Leu Thr<br>               290                           295                          300 | | 1093 |
| ccc cat cca ccg caa aaa cag gcg tat ggt gtg aca tta ccc act tca<br>Pro His Pro Pro Gln Lys Gln Ala Tyr Gly Val Thr Leu Pro Thr Ser<br>          305                           310                           315 | | 1141 |
| gtg ctg ttt atc gcc gga cac gat act aat ctg gca aat ctc ggc ggc<br>Val Leu Phe Ile Ala Gly His Asp Thr Asn Leu Ala Asn Leu Gly Gly<br>320                                 325                           330 | | 1189 |
| gca ctg gag ctc aac tgg acg ctt ccc ggt cag ccg gat aac acg ccg<br>Ala Leu Glu Leu Asn Trp Thr Leu Pro Gly Gln Pro Asp Asn Thr Pro<br>335                                 340                           345                     350 | | 1237 |
| cca ggt ggt gaa ctg gtg ttt gaa cgc tgg cgt cgg cta agc gat aac<br>Pro Gly Gly Glu Leu Val Phe Glu Arg Trp Arg Arg Leu Ser Asp Asn<br>                   355                           360                          365 | | 1285 |
| agc cag tgg att cag gtt tcg ctg gtc ttc cag act tta cag cag atg<br>Ser Gln Trp Ile Gln Val Ser Leu Val Phe Gln Thr Leu Gln Gln Met<br>               370                           375                          380 | | 1333 |
| cgt gat aaa acg ccg ctg tca tta aat acg ccg ccc gga gag gtg aaa<br>Arg Asp Lys Thr Pro Leu Ser Leu Asn Thr Pro Pro Gly Glu Val Lys<br>          385                           390                           395 | | 1381 |
| ctg acc ctg gca gga tgt gaa gag cga aat gcg cag ggc atg tgt tcg<br>Leu Thr Leu Ala Gly Cys Glu Glu Arg Asn Ala Gln Gly Met Cys Ser<br>400                                 405                           410 | | 1429 |
| ttg gca ggt ttt acg caa atc gtg aat gaa gca cgc ata ccg gcg tgc<br>Leu Ala Gly Phe Thr Gln Ile Val Asn Glu Ala Arg Ile Pro Ala Cys<br>415                                 420                           425                     430 | | 1477 |
| agt ttg taatgcataa aaaagagcat tcagttacct gaatgctctg aggctgatga<br>Ser Leu | | 1533 |

```
caaacgaaga actgtctaat gcgtagaccg gaaaaggcgt tcacgccgca tccggccact   1593
ttcagttttc ctctttctcg gagtaactat aaccgtaata gttatagccg taactgtaag   1653
cggtgctggc gcgtttaatc acaccattga ggatagcgcc tttaatattg acgcctgcct   1713
gttccagacg ctgcattgac aaactcacct ctttggcggt gttcaagcca aaacgcgcaa   1773
ccagcaggct ggtgccaaca gaacgcccca cgaccgcggc atcactcacc gccagcatcg   1833
gcggcgtatc gacaatcacc agatcgtaat ggtcgttcgc ccattccagt aattgacgca   1893
tccgatcg                                                           1901

<210> SEQ ID NO 4
<211> LENGTH: 432
<212> TYPE: PRT
<213> ORGANISM: Escherichia coli

<400> SEQUENCE: 4

Met Lys Ala Ile Leu Ile Pro Phe Leu Ser Leu Leu Ile Pro Leu Thr
  1               5                  10                  15

Pro Gln Ser Ala Phe Ala Gln Ser Glu Pro Glu Leu Lys Leu Glu Ser
                 20                  25                  30

Val Val Ile Val Ser Arg His Gly Val Arg Ala Pro Thr Lys Ala Thr
             35                  40                  45

Gln Leu Met Gln Asp Val Thr Pro Asp Ala Trp Pro Thr Trp Pro Val
         50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Ser Gly Gln Val Ala Ile Ile Ala Asp Val Asp
                100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
        130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300
```

```
Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```